US008591395B2

(12) United States Patent  
Ortiz et al.

(10) Patent No.: US 8,591,395 B2  
(45) Date of Patent: Nov. 26, 2013

(54) GASTRIC RESTRICTION DEVICE DATA HANDLING DEVICES AND METHODS

(75) Inventors: Mark S. Ortiz, Milford, OH (US); David N. Plescia, Cincinnati, OH (US); Daniel F. Dlugos, Jr., Middletown, OH (US); David C. Yates, West Chester, OH (US); Kevin Doll, Mason, OH (US)

(73) Assignee: Ethicon Endo-Surgery, Inc., Cincinnati, OH (US)

( * ) Notice: Subject to any disclaimer, the term of this patent is extended or adjusted under 35 U.S.C. 154(b) by 975 days.

(21) Appl. No.: 12/020,888

(22) Filed: Jan. 28, 2008

(65) Prior Publication Data

US 2009/0192415 A1    Jul. 30, 2009

(51) Int. Cl.  
  *A61F 2/00*  (2006.01)
(52) U.S. Cl.  
  USPC .......................................................... 600/37
(58) Field of Classification Search  
  USPC ........ 600/37, 593, 29–31, 485, 507; 606/151; 128/897–899; 607/60, 61, 2, 42  
  See application file for complete search history.

(56) References Cited

U.S. PATENT DOCUMENTS

| | | |
|---|---|---|
| RE3,036 E | 7/1868 | Shunk |
| RE3,037 E | 7/1868 | Tucker |
| RE3,115 E | 9/1868 | Lewis |
| RE3,187 E | 11/1868 | Winchester |
| RE3,322 E | 3/1869 | Murch |
| 236,373 A | 1/1881 | Spilman |
| 322,388 A | 7/1885 | Lord |
| 400,401 A | 3/1889 | Gutzkow |
| D23,637 S | 9/1894 | Casad et al. |
| D24,900 S | 11/1895 | Clemecet |
| D25,318 S | 3/1896 | Perky |
| D27,151 S | 6/1897 | Moulten |
| D29,715 S | 11/1898 | Wheeler |
| D29,745 S | 11/1898 | Bunker |

(Continued)

FOREIGN PATENT DOCUMENTS

| | | |
|---|---|---|
| CA | 1059035 | 7/1979 |
| CA | 1119469 | 3/1982 |

(Continued)

OTHER PUBLICATIONS

"Application Specific Integrated Circuits (ASICs)", Honeywell product information from website http://www.honeywell.com/sites/portal?smap=aerospace&page=Radiation-Hardened-Electronics3&theme=T18&catID=CE06BEF88-65F8-6A1E-4ED1-6A1EC1B7AE7A&id=HA0E380D3-C27B-9EBF-AAC8-9FAF8851256D&sel=1&sel4=1; 1 page.

(Continued)

*Primary Examiner* — Christine Matthews  
*Assistant Examiner* — Shannon McBride

(57) ABSTRACT

Methods and devices are provided for handling data in an implantable restriction system. In general, the methods and devices allow collection, analysis, storage, and transmission of pressure measurements. Pressure measurement data can be compressed before storing it. Additionally, not all pressure data need be recorded or retained, such as data substantially equaling a resting or nominal pressure of an implantable restriction device indicative of little to no pressure variation and data indicative of isolated, non-recurring events. Any pressure measurement data that is recorded can be transmitted to an external device using power telemetrically provided by the external device.

20 Claims, 15 Drawing Sheets

(56) References Cited

U.S. PATENT DOCUMENTS

| | | |
|---|---|---|
| D29,885 S | 12/1898 | Hughel et al. |
| D30,690 S | 5/1899 | Schwedtmann |
| D30,966 S | 6/1899 | Howe |
| D31,230 S | 7/1899 | Hogan |
| 689,758 A | 12/1901 | Shaw |
| 724,913 A | 4/1903 | Montgomery |
| 899,477 A | 9/1908 | Williams |
| 926,197 A | 6/1909 | Kim |
| 953,875 A | 4/1910 | Waring |
| 991,192 A | 5/1911 | Batttenfeld |
| 1,087,988 A | 2/1914 | Sheldon |
| 1,210,701 A | 1/1917 | Ryden |
| 1,219,296 A | 3/1917 | Hahn |
| 1,224,355 A | 5/1917 | Brown |
| 1,263,914 A | 4/1918 | Martin |
| 1,310,290 A | 7/1919 | Piechowicz |
| 1,384,873 A | 7/1921 | Strickland |
| 1,421,507 A | 7/1922 | Lindberg |
| 1,551,525 A | 8/1925 | Hamer |
| 1,560,973 A | 11/1925 | Cheron |
| 1,620,633 A | 3/1927 | Colvin |
| 1,623,403 A | 4/1927 | Friel |
| 1,689,085 A | 10/1928 | Russell et al. |
| 1,764,071 A | 6/1930 | Foulke |
| 1,782,704 A | 11/1930 | Woodruff |
| 1,807,107 A | 5/1931 | Sternberch |
| 1,865,446 A | 7/1932 | Sears |
| 1,882,338 A | 10/1932 | Reed et al. |
| 1,924,781 A | 8/1933 | Gaiser |
| 2,027,875 A | 1/1936 | Odend'hal |
| 2,063,430 A | 12/1936 | Graser |
| 2,099,160 A | 11/1937 | Charch |
| 2,105,127 A | 1/1938 | Petrone |
| 2,106,192 A | 1/1938 | Saville |
| 2,143,429 A | 1/1939 | Auble |
| 2,166,603 A | 7/1939 | Menzer |
| 2,168,427 A | 8/1939 | McConkey |
| 2,174,525 A | 10/1939 | Padernal |
| 2,177,564 A | 10/1939 | Havill |
| 2,178,463 A | 10/1939 | Bahnson |
| 2,180,599 A | 11/1939 | Menasco |
| 2,203,460 A | 6/1940 | Fieber |
| 2,206,038 A | 7/1940 | Ford |
| 2,216,374 A | 10/1940 | Martin |
| 2,223,699 A | 12/1940 | Norgren |
| 2,225,145 A | 12/1940 | Baumbach |
| 2,225,880 A | 12/1940 | Montelius |
| 2,261,060 A | 10/1941 | Giesler |
| 2,261,355 A | 11/1941 | Flynn |
| 2,295,539 A | 9/1942 | Beach |
| 2,303,108 A | 11/1942 | Blackburn |
| 2,303,502 A | 12/1942 | Rous |
| 2,318,819 A | 5/1943 | Verson |
| 2,327,407 A | 8/1943 | Edyvean |
| 2,327,615 A | 8/1943 | Ankarlo |
| 2,354,571 A | 7/1944 | Blain |
| 2,426,392 A | 8/1947 | Fennema |
| 2,426,817 A | 9/1947 | Charlton et al. |
| 2,440,260 A | 4/1948 | Gall |
| 2,442,573 A | 6/1948 | Stafford |
| 2,453,217 A | 11/1948 | Gregg et al. |
| 2,455,859 A | 12/1948 | Foley |
| 2,477,922 A | 8/1949 | Emery et al. |
| 2,478,876 A | 8/1949 | Nelson |
| 2,482,392 A | 9/1949 | Whitaker |
| 2,494,881 A | 1/1950 | Kost |
| 2,509,210 A | 5/1950 | Clark |
| 2,509,673 A | 5/1950 | Church |
| 2,511,765 A | 6/1950 | Bradbury |
| 2,520,056 A | 8/1950 | Pozun |
| 2,521,976 A | 9/1950 | Hays |
| 2,533,924 A | 12/1950 | Foley |
| 2,538,259 A | 1/1951 | Merriman |
| 2,581,479 A | 1/1952 | Grashman |
| 2,600,324 A | 6/1952 | Rappaport |
| 2,606,003 A | 8/1952 | McNeill |
| 2,615,940 A | 10/1952 | Williams |
| 2,632,447 A | 3/1953 | Dobes |
| 2,639,342 A | 5/1953 | Cope |
| 2,640,119 A | 5/1953 | Bradford, Jr. |
| 2,641,742 A | 6/1953 | Wolfe |
| 2,651,304 A | 9/1953 | Browner |
| 2,665,577 A | 1/1954 | Sanowskis |
| 2,673,999 A | 4/1954 | Shey |
| 2,676,609 A | 4/1954 | Pfarrer |
| 2,684,118 A | 7/1954 | Osmun |
| 2,689,611 A | 9/1954 | Martinson |
| 2,697,435 A | 12/1954 | Ray |
| 2,723,323 A | 11/1955 | Niemi |
| 2,734,992 A | 2/1956 | Elliot et al. |
| 2,740,007 A | 3/1956 | Amelang |
| 2,740,853 A | 4/1956 | Hatman, Jr. |
| 2,742,323 A | 4/1956 | Shey |
| 2,747,332 A | 5/1956 | Morehouse |
| 2,753,876 A | 7/1956 | Kurt |
| 2,756,883 A | 7/1956 | Schreck |
| 2,756,983 A | 7/1956 | Furcini |
| 2,761,603 A | 9/1956 | Fairchild |
| 2,773,312 A | 12/1956 | Peck |
| 2,783,728 A | 3/1957 | Hoffmann |
| 2,787,875 A | 4/1957 | Johnson |
| 2,793,379 A | 5/1957 | Moore |
| 2,795,460 A | 6/1957 | Bletcher |
| 2,804,514 A | 8/1957 | Peters |
| 2,822,113 A | 2/1958 | Joiner, Jr. |
| 2,831,478 A | 4/1958 | Uddenberg et al. |
| 2,864,393 A | 12/1958 | Drake |
| 2,865,541 A | 12/1958 | Hicks |
| 2,870,024 A | 1/1959 | Martin |
| 2,883,995 A | 4/1959 | Bialous et al. |
| 2,886,355 A | 5/1959 | Wurzel |
| 2,895,215 A | 7/1959 | Neher et al. |
| 2,899,493 A | 8/1959 | Levine |
| 2,902,861 A | 9/1959 | Frost et al. |
| 2,923,531 A | 2/1960 | Bauer et al. |
| 2,924,263 A | 2/1960 | Landis |
| 2,924,432 A | 2/1960 | Arps et al. |
| 2,930,170 A | 3/1960 | Holsman et al. |
| 2,938,592 A | 5/1960 | Charske et al. |
| 2,941,338 A | 6/1960 | Santschi |
| 2,943,682 A | 7/1960 | Ingram, Jr. et al. |
| 2,958,781 A | 11/1960 | Marchal et al. |
| 2,961,479 A | 11/1960 | Bertling |
| 2,976,355 A | 3/1961 | Levine |
| 2,976,686 A | 3/1961 | Stelzer |
| 2,977,876 A | 4/1961 | Meyers |
| 2,986,715 A | 5/1961 | Church et al. |
| 2,989,019 A | 6/1961 | Van Sciver, II |
| 3,010,692 A | 11/1961 | Jentoft |
| 3,013,234 A | 12/1961 | Bourns |
| 3,018,791 A | 1/1962 | Knox |
| 3,034,356 A | 5/1962 | Bieganski |
| 3,040,800 A | 6/1962 | Hartley |
| 3,054,618 A | 9/1962 | Abrams et al. |
| 3,060,262 A | 10/1962 | Hoer |
| 3,070,373 A | 12/1962 | Mathews et al. |
| 3,082,414 A | 3/1963 | Papaminas |
| 3,085,577 A | 4/1963 | Berman et al. |
| 3,096,410 A | 7/1963 | Anderson |
| 3,099,262 A | 7/1963 | Bigliano |
| 3,125,028 A | 3/1964 | Rohde |
| 3,126,029 A | 3/1964 | Englesson |
| 3,129,072 A | 4/1964 | Cook et al. |
| 3,135,914 A | 6/1964 | Callan et al. |
| 3,144,017 A | 8/1964 | Muth |
| 3,151,258 A | 9/1964 | Sonderegger et al. |
| 3,153,460 A | 10/1964 | Raskin |
| 3,161,051 A | 12/1964 | Perry, Jr. |
| 3,167,044 A | 1/1965 | Henrickson |
| 3,171,549 A | 3/1965 | Orloff |
| 3,172,700 A | 3/1965 | Haas |
| 3,173,269 A | 3/1965 | Imbertson |
| 3,182,494 A | 5/1965 | Beatty et al. |
| 3,187,181 A | 6/1965 | Keller |

(56) References Cited

U.S. PATENT DOCUMENTS

| | | |
|---|---|---|
| 3,187,745 A | 6/1965 | Baum et al. |
| 3,190,388 A | 6/1965 | Moser et al. |
| 3,205,547 A | 9/1965 | Riekse |
| 3,208,255 A | 9/1965 | Burk |
| 3,209,570 A | 10/1965 | Hills |
| 3,221,468 A | 12/1965 | Casey |
| 3,228,703 A | 1/1966 | Wilson |
| 3,229,684 A | 1/1966 | Nagumo et al. |
| 3,236,088 A | 2/1966 | Moller |
| 3,238,624 A | 3/1966 | McCabe |
| 3,240,510 A | 3/1966 | Spouge |
| 3,245,642 A | 4/1966 | Dicke |
| 3,255,568 A | 6/1966 | Martin et al. |
| 3,260,091 A | 7/1966 | Shaw, Jr. |
| 3,265,822 A | 8/1966 | Moulten |
| 3,266,487 A | 8/1966 | Watkins et al. |
| 3,273,447 A | 9/1966 | Frank |
| 3,283,352 A | 11/1966 | Hu |
| 3,290,919 A | 12/1966 | Malinak et al. |
| 3,292,493 A | 12/1966 | Franklin |
| 3,292,888 A | 12/1966 | Fischer |
| 3,294,988 A | 12/1966 | Packard |
| 3,299,603 A | 1/1967 | Shaw |
| 3,299,882 A | 1/1967 | Masino |
| 3,301,514 A | 1/1967 | Sugaya |
| 3,302,457 A | 2/1967 | Mayes |
| 3,306,384 A | 2/1967 | Ross |
| 3,313,314 A | 4/1967 | Burke et al. |
| 3,316,935 A | 5/1967 | Kaiser et al. |
| 3,320,750 A | 5/1967 | Haise et al. |
| 3,321,035 A | 5/1967 | Tarpley |
| 3,332,788 A | 7/1967 | Barnby |
| 3,334,510 A | 8/1967 | Hallesy |
| 3,339,401 A | 9/1967 | Peters |
| 3,340,868 A | 9/1967 | Darling |
| 3,347,162 A | 10/1967 | Braznell |
| 3,350,944 A | 11/1967 | De Michele |
| 3,353,364 A | 11/1967 | Blanding et al. |
| 3,353,481 A | 11/1967 | Antonucci |
| 3,356,334 A | 12/1967 | Scaramucci |
| 3,356,510 A | 12/1967 | Barnby |
| 3,357,218 A | 12/1967 | Mitchell |
| 3,357,461 A | 12/1967 | Friendship |
| 3,359,741 A | 12/1967 | Nelson |
| 3,361,300 A | 1/1968 | Kaplan |
| 3,364,929 A | 1/1968 | Ide et al. |
| 3,365,684 A | 1/1968 | Stemke |
| 3,378,456 A | 4/1968 | Roberts |
| 3,380,445 A | 4/1968 | Frasier |
| 3,380,649 A | 4/1968 | Roberts |
| 3,385,022 A | 5/1968 | Anderson |
| 3,389,355 A | 6/1968 | Schroeder, Jr. |
| 3,393,612 A | 7/1968 | Gorgens et al. |
| 3,396,561 A | 8/1968 | Day |
| 3,399,667 A | 9/1968 | Nishimoto et al. |
| 3,400,734 A | 9/1968 | Rosenberg |
| 3,403,237 A | 9/1968 | Wysong |
| 3,409,924 A | 11/1968 | Slama |
| 3,411,347 A | 11/1968 | Wirth et al. |
| 3,417,476 A | 12/1968 | Martens |
| 3,420,325 A | 1/1969 | McAlister et al. |
| 3,422,324 A | 1/1969 | Webb |
| 3,426,165 A | 2/1969 | Beaman |
| 3,438,391 A | 4/1969 | Yocum |
| 3,443,608 A | 5/1969 | Copping et al. |
| 3,445,335 A | 5/1969 | Gluntz |
| 3,447,281 A | 6/1969 | Bufford et al. |
| 3,450,153 A | 6/1969 | Hildebrandt et al. |
| 3,453,546 A | 7/1969 | Fryer |
| 3,453,848 A | 7/1969 | Williamson |
| 3,456,134 A | 7/1969 | Ko |
| 3,457,909 A | 7/1969 | Laird |
| 3,460,557 A | 8/1969 | Gallant |
| 3,463,338 A | 8/1969 | Schneider |
| 3,469,818 A | 9/1969 | Cowan |
| 3,470,725 A | 10/1969 | Brown et al. |
| 3,472,230 A | 10/1969 | Fogarty |
| 3,478,344 A | 11/1969 | Schwitzgebel et al. |
| 3,482,449 A | 12/1969 | Werner |
| 3,482,816 A | 12/1969 | Arnold |
| 3,487,959 A | 1/1970 | Pearne et al. |
| 3,491,842 A | 1/1970 | Delacour et al. |
| 3,492,638 A | 1/1970 | Lane |
| 3,502,829 A | 3/1970 | Reynolds |
| 3,503,116 A | 3/1970 | Strack |
| 3,504,664 A | 4/1970 | Haddad |
| 3,505,808 A | 4/1970 | Eschle |
| 3,509,754 A | 5/1970 | Massingill, et al. |
| 3,512,517 A | 5/1970 | Kadish et al. |
| 3,514,919 A | 6/1970 | Ashton et al. |
| 3,516,220 A | 6/1970 | Buford et al. |
| 3,517,553 A | 6/1970 | Williams et al. |
| 3,527,226 A | 9/1970 | Hakin et al. |
| 3,529,908 A | 9/1970 | Smith |
| 3,530,449 A | 9/1970 | Anderson |
| 3,533,403 A | 10/1970 | Woodson |
| 3,534,728 A | 10/1970 | Barrows |
| 3,534,872 A | 10/1970 | Roth et al. |
| 3,535,914 A | 10/1970 | Veith et al. |
| 3,539,009 A | 11/1970 | Kudlaty |
| 3,543,744 A | 12/1970 | LePar |
| 3,545,275 A | 12/1970 | Harrison et al. |
| 3,550,583 A | 12/1970 | Chiku |
| 3,550,847 A | 12/1970 | Scott |
| 3,563,094 A | 2/1971 | Rieschel |
| 3,563,245 A | 2/1971 | McLean et al. |
| 3,566,083 A | 2/1971 | McMillin |
| 3,566,875 A | 3/1971 | Stoehr |
| 3,568,367 A | 3/1971 | Myers |
| 3,568,636 A | 3/1971 | Lockwood |
| 3,576,554 A | 4/1971 | Temps, Jr. et al. |
| 3,580,082 A | 5/1971 | Strack |
| 3,581,402 A | 6/1971 | London et al. |
| 3,583,387 A | 6/1971 | Garner et al. |
| 3,587,204 A | 6/1971 | George |
| 3,590,809 A | 7/1971 | London |
| 3,590,818 A | 7/1971 | Lemole |
| 3,590,992 A | 7/1971 | Soderstrom |
| 3,592,183 A | 7/1971 | Watkins et al. |
| 3,594,519 A | 7/1971 | Schmidlin |
| 3,602,885 A | 8/1971 | Grajeda |
| 3,610,016 A | 10/1971 | Bultman |
| 3,610,851 A | 10/1971 | Krupski |
| 3,611,811 A | 10/1971 | Lissau |
| 3,614,926 A | 10/1971 | Brechtel |
| 3,614,955 A | 10/1971 | Mirowski et al. |
| 3,619,742 A | 11/1971 | Rud, Jr. |
| 3,623,371 A | 11/1971 | Jullien-Davin |
| 3,624,854 A | 12/1971 | Strong |
| 3,630,242 A | 12/1971 | Schieser et al. |
| 3,631,847 A | 1/1972 | Hobbs, II |
| 3,633,881 A | 1/1972 | Yurdin |
| 3,635,061 A | 1/1972 | Rydell et al. |
| 3,635,074 A | 1/1972 | Moos et al. |
| 3,638,496 A | 2/1972 | King |
| 3,644,883 A | 2/1972 | Borman et al. |
| 3,648,687 A | 3/1972 | Ramsey, III |
| 3,651,289 A | 3/1972 | Nagashima |
| 3,651,405 A | 3/1972 | Whitney et al. |
| 3,653,671 A | 4/1972 | Shipes |
| 3,659,615 A | 5/1972 | Enger |
| 3,677,685 A | 7/1972 | Aoki |
| 3,686,958 A | 8/1972 | Porter et al. |
| 3,688,568 A | 9/1972 | Karper et al. |
| 3,701,392 A | 10/1972 | Wirth et al. |
| 3,702,677 A | 11/1972 | Heffington |
| 3,703,099 A | 11/1972 | Rouse et al. |
| 3,712,138 A | 1/1973 | Alinari et al. |
| 3,713,124 A | 1/1973 | Durland et al. |
| 3,719,524 A | 3/1973 | Ripley et al. |
| 3,721,412 A | 3/1973 | Kindorf |
| 3,723,247 A | 3/1973 | Leine et al. |
| 3,724,000 A | 4/1973 | Eakman |
| 3,727,463 A | 4/1973 | Intraub |

(56) References Cited

U.S. PATENT DOCUMENTS

| | | |
|---|---|---|
| 3,727,616 A | 4/1973 | Lenzkes |
| 3,730,174 A | 5/1973 | Madison |
| 3,730,560 A | 5/1973 | Abildgaard et al. |
| 3,731,679 A | 5/1973 | Wilhelmson et al. |
| 3,731,681 A | 5/1973 | Blackshear et al. |
| 3,732,731 A | 5/1973 | Fussell, Jr. |
| 3,735,040 A | 5/1973 | Punt et al. |
| 3,736,930 A | 6/1973 | Georgi |
| 3,738,356 A | 6/1973 | Workman |
| 3,740,921 A | 6/1973 | Meyer et al. |
| 3,746,111 A | 7/1973 | Berthiaume et al. |
| 3,748,678 A | 7/1973 | Ballou |
| 3,749,098 A | 7/1973 | De Bennetot et al. |
| 3,749,422 A | 7/1973 | Abildgaard et al. |
| 3,749,423 A | 7/1973 | Abildgaard et al. |
| 3,750,194 A | 8/1973 | Summers |
| 3,757,770 A | 9/1973 | Brayshaw et al. |
| 3,759,095 A | 9/1973 | Short, Jr. et al. |
| 3,760,638 A | 9/1973 | Lawson et al. |
| 3,763,960 A | 10/1973 | John et al. |
| 3,765,142 A | 10/1973 | Lindquist et al. |
| 3,765,494 A | 10/1973 | Kielman, Jr. |
| 3,769,156 A | 10/1973 | Brecy et al. |
| 3,769,830 A | 11/1973 | Porter et al. |
| 3,774,243 A | 11/1973 | Ng et al. |
| 3,776,333 A | 12/1973 | Mathauser |
| 3,778,051 A | 12/1973 | Allen et al. |
| 3,780,578 A | 12/1973 | Sellman et al. |
| 3,781,902 A | 12/1973 | Shim et al. |
| 3,783,585 A | 1/1974 | Hoyland et al. |
| 3,789,667 A | 2/1974 | Porter et al. |
| 3,796,095 A | 3/1974 | Fussell, Jr. |
| 3,807,219 A | 4/1974 | Wallskog |
| 3,811,429 A | 5/1974 | Fletcher et al. |
| 3,815,722 A | 6/1974 | Sessoms |
| 3,818,765 A | 6/1974 | Eriksen et al. |
| 3,820,400 A | 6/1974 | Russo |
| 3,820,795 A | 6/1974 | Taylor |
| 3,823,610 A | 7/1974 | Fussell, Jr. |
| 3,825,065 A | 7/1974 | Lloyd et al. |
| 3,825,963 A | 7/1974 | Abildgaard et al. |
| 3,825,964 A | 7/1974 | Groswith, III et al. |
| 3,828,672 A | 8/1974 | Gazzola et al. |
| 3,828,766 A | 8/1974 | Krasnow |
| 3,831,588 A | 8/1974 | Rindner |
| 3,831,942 A | 8/1974 | Del Mar |
| 3,833,238 A | 9/1974 | Liard et al. |
| 3,834,167 A | 9/1974 | Tabor |
| 3,834,739 A | 9/1974 | Abildgaard et al. |
| 3,835,523 A | 9/1974 | Stansfield et al. |
| 3,839,708 A | 10/1974 | Bredesen et al. |
| 3,842,483 A | 10/1974 | Cramer |
| 3,842,668 A | 10/1974 | Lippke et al. |
| 3,845,664 A | 11/1974 | Perry, Jr. |
| 3,845,751 A | 11/1974 | Runstetler |
| 3,845,757 A | 11/1974 | Weyer |
| 3,847,434 A | 11/1974 | Weman et al. |
| 3,850,208 A | 11/1974 | Hamilton |
| 3,853,117 A | 12/1974 | Murr |
| 3,854,469 A | 12/1974 | Giori et al. |
| 3,855,902 A | 12/1974 | Kirst et al. |
| 3,857,399 A | 12/1974 | Zacouto et al. |
| 3,857,452 A | 12/1974 | Hartman |
| 3,857,745 A | 12/1974 | Grausch et al. |
| 3,858,581 A | 1/1975 | Kamen |
| 3,863,622 A | 2/1975 | Buuck |
| 3,863,933 A | 2/1975 | Tredway |
| 3,867,950 A | 2/1975 | Fischell |
| 3,868,008 A | 2/1975 | Brumbaugh |
| 3,868,679 A | 2/1975 | Arneson |
| 3,871,599 A | 3/1975 | Takada et al. |
| 3,872,285 A | 3/1975 | Shum et al. |
| 3,874,388 A | 4/1975 | King et al. |
| 3,876,980 A | 4/1975 | Haemmig et al. |
| 3,878,908 A | 4/1975 | Andersson et al. |
| 3,881,528 A | 5/1975 | Mackenzie |
| 3,893,111 A | 7/1975 | Cotter |
| 3,893,451 A | 7/1975 | Durand et al. |
| 3,895,681 A | 7/1975 | Griffin et al. |
| 3,899,862 A | 8/1975 | Muys et al. |
| 3,904,234 A | 9/1975 | Hill et al. |
| 3,908,334 A | 9/1975 | Rychiger |
| 3,908,461 A | 9/1975 | Turpen |
| 3,908,721 A | 9/1975 | McGahey et al. |
| 3,910,087 A | 10/1975 | Jones |
| 3,912,168 A | 10/1975 | Mullins et al. |
| 3,912,304 A | 10/1975 | Abildgaard et al. |
| 3,918,286 A | 11/1975 | Whitehead |
| 3,918,291 A | 11/1975 | Pauly et al. |
| 3,920,965 A | 11/1975 | Sohrwardy et al. |
| 3,921,682 A | 11/1975 | McGahey et al. |
| 3,922,951 A | 12/1975 | Linsinger |
| 3,923,060 A | 12/1975 | Ellinwood, Jr. |
| 3,924,635 A | 12/1975 | Hakim |
| 3,928,980 A | 12/1975 | Ganzinotti |
| 3,929,175 A | 12/1975 | Coone |
| 3,930,682 A | 1/1976 | Booth |
| 3,930,852 A | 1/1976 | Tanaka et al. |
| 3,936,028 A | 2/1976 | Norton et al. |
| 3,940,122 A | 2/1976 | Janzen et al. |
| 3,940,630 A | 2/1976 | Bergonz |
| 3,942,299 A | 3/1976 | Bory et al. |
| 3,942,382 A | 3/1976 | Hok et al. |
| 3,942,516 A | 3/1976 | Glynn et al. |
| 3,942,536 A | 3/1976 | Mirowski et al. |
| 3,943,915 A | 3/1976 | Severson |
| 3,945,704 A | 3/1976 | Kraus et al. |
| 3,946,613 A | 3/1976 | Silver |
| 3,946,615 A | 3/1976 | Hluchan |
| 3,946,724 A | 3/1976 | La Balme et al. |
| 3,948,141 A | 4/1976 | Shinjo et al. |
| 3,949,388 A | 4/1976 | Fuller |
| 3,953,289 A | 4/1976 | Costes |
| 3,954,271 A | 5/1976 | Tredway, Sr. |
| 3,958,558 A | 5/1976 | Dunphy et al. |
| 3,961,425 A | 6/1976 | Swanson et al. |
| 3,961,646 A | 6/1976 | Schon et al. |
| 3,962,895 A | 6/1976 | Rydell et al. |
| 3,962,921 A | 6/1976 | Lips |
| 3,963,019 A | 6/1976 | Quandt |
| 3,964,485 A | 6/1976 | Neumeier |
| 3,964,770 A | 6/1976 | Abildgaard et al. |
| 3,967,737 A | 7/1976 | Peralta et al. |
| 3,968,473 A | 7/1976 | Patton et al. |
| 3,968,694 A | 7/1976 | Clark |
| 3,972,320 A | 8/1976 | Kalman |
| 3,973,753 A | 8/1976 | Wheeler |
| 3,973,858 A | 8/1976 | Poisson et al. |
| 3,974,655 A | 8/1976 | Halpern et al. |
| 3,974,865 A | 8/1976 | Fenton et al. |
| 3,977,391 A | 8/1976 | Fleischmann |
| 3,980,871 A | 9/1976 | Lindstrom et al. |
| 3,982,571 A | 9/1976 | Fenton et al. |
| 3,983,948 A | 10/1976 | Jeter |
| 3,985,133 A | 10/1976 | Jenkins et al. |
| 3,987,860 A | 10/1976 | Jabsen |
| 3,989,005 A | 11/1976 | Bowler, Jr. et al. |
| 3,991,749 A | 11/1976 | Zent |
| 3,992,948 A | 11/1976 | D'Antonio et al. |
| 3,993,149 A | 11/1976 | Harvey |
| 3,996,927 A | 12/1976 | Frank |
| 3,996,962 A | 12/1976 | Sutherland |
| 4,003,141 A | 1/1977 | Le Roy |
| 4,005,282 A | 1/1977 | Jennings |
| 4,005,593 A | 2/1977 | Goldberg |
| 4,006,735 A | 2/1977 | Hittman et al. |
| 4,009,375 A | 2/1977 | White et al. |
| 4,009,591 A | 3/1977 | Hester |
| 4,010,449 A | 3/1977 | Faggin et al. |
| 4,014,319 A | 3/1977 | Favre et al. |
| 4,014,321 A | 3/1977 | March |
| 4,016,764 A | 4/1977 | Rice |
| 4,017,329 A | 4/1977 | Larson |
| 4,018,134 A | 4/1977 | Linsinger et al. |

(56) References Cited

U.S. PATENT DOCUMENTS

| | | |
|---|---|---|
| 4,022,190 A | 5/1977 | Meyer |
| 4,024,864 A | 5/1977 | Davies et al. |
| 4,025,912 A | 5/1977 | Rice |
| 4,026,276 A | 5/1977 | Chubbuck |
| 4,027,661 A | 6/1977 | Lyon et al. |
| 4,031,899 A | 6/1977 | Renirie et al. |
| 4,036,775 A | 7/1977 | Trautvetter et al. |
| 4,039,069 A | 8/1977 | Kwan et al. |
| 4,041,954 A | 8/1977 | Ohara et al. |
| 4,042,504 A | 8/1977 | Drori et al. |
| 4,045,345 A | 8/1977 | Drori et al. |
| 4,047,851 A | 9/1977 | Bender |
| 4,048,494 A | 9/1977 | Liesting et al. |
| 4,048,879 A | 9/1977 | Cox |
| 4,049,004 A | 9/1977 | Walters |
| 4,051,338 A | 9/1977 | Harris, III |
| 4,052,991 A | 10/1977 | Zacouto et al. |
| 4,055,074 A | 10/1977 | Thimons et al. |
| 4,055,175 A | 10/1977 | Clemens et al. |
| 4,056,854 A | 11/1977 | Boretos et al. |
| 4,058,007 A | 11/1977 | Exner et al. |
| 4,062,351 A | 12/1977 | Hastwell et al. |
| 4,062,354 A | 12/1977 | Taylor et al. |
| 4,062,360 A | 12/1977 | Bentley |
| 4,063,439 A | 12/1977 | Besson et al. |
| 4,064,882 A | 12/1977 | Johnson et al. |
| 4,070,239 A | 1/1978 | Bevilacqua |
| 4,072,047 A | 2/1978 | Reismuller et al. |
| 4,073,292 A | 2/1978 | Edelman |
| 4,075,099 A | 2/1978 | Pelton et al. |
| 4,075,602 A | 2/1978 | Clothier |
| 4,077,072 A | 3/1978 | Dezura et al. |
| 4,077,394 A | 3/1978 | McCurdy |
| 4,077,405 A | 3/1978 | Haerten et al. |
| 4,077,882 A | 3/1978 | Gangemi |
| 4,078,620 A | 3/1978 | Westlake et al. |
| 4,080,653 A | 3/1978 | Barnes, Jr. et al. |
| 4,084,752 A | 4/1978 | Hagiwara et al. |
| 4,086,488 A | 4/1978 | Hill |
| 4,087,568 A | 5/1978 | Fay et al. |
| 4,088,417 A | 5/1978 | Kosmowski |
| 4,089,329 A | 5/1978 | Couvillon, Jr. et al. |
| 4,090,802 A | 5/1978 | Bilz et al. |
| 4,092,719 A | 5/1978 | Salmon et al. |
| 4,092,925 A | 6/1978 | Fromson |
| 4,096,866 A | 6/1978 | Fischell |
| 4,098,293 A | 7/1978 | Kramer et al. |
| 4,103,496 A | 8/1978 | Colamussi et al. |
| 4,106,370 A | 8/1978 | Kraus et al. |
| 4,107,689 A | 8/1978 | Jellinek |
| 4,107,995 A | 8/1978 | Ligman et al. |
| 4,108,148 A | 8/1978 | Cannon, III |
| 4,108,575 A | 8/1978 | Schal et al. |
| 4,109,148 A | 8/1978 | Jaulmes et al. |
| 4,109,518 A | 8/1978 | Dooley et al. |
| 4,109,644 A | 8/1978 | Kojima |
| 4,111,056 A | 9/1978 | Mastromatteo |
| 4,111,629 A | 9/1978 | Nussbaumer |
| 4,114,424 A | 9/1978 | Johnson |
| 4,114,606 A | 9/1978 | Seylar |
| 4,120,097 A | 10/1978 | Jeter |
| 4,120,134 A | 10/1978 | Scholle |
| 4,121,635 A | 10/1978 | Hansel |
| 4,123,310 A | 10/1978 | Varon et al. |
| 4,124,023 A | 11/1978 | Fleischmann et al. |
| 4,127,110 A | 11/1978 | Bullara |
| 4,130,169 A | 12/1978 | Denison |
| 4,131,596 A | 12/1978 | Allen |
| 4,133,355 A | 1/1979 | Mayer |
| 4,133,367 A | 1/1979 | Abell |
| 4,140,131 A | 2/1979 | Dutcher et al. |
| 4,141,348 A | 2/1979 | Hittman |
| 4,141,349 A | 2/1979 | Ory et al. |
| 4,143,661 A | 3/1979 | LaForge et al. |
| 4,146,029 A | 3/1979 | Ellinwood, Jr. |
| 4,147,161 A | 4/1979 | Ikebe et al. |
| 4,148,096 A | 4/1979 | Haas et al. |
| 4,149,423 A | 4/1979 | Frosch et al. |
| 4,151,823 A | 5/1979 | Grosse et al. |
| 4,153,085 A | 5/1979 | Adams |
| 4,156,422 A | 5/1979 | Hildebrandt et al. |
| 4,160,448 A | 7/1979 | Jackson |
| 4,160,971 A | 7/1979 | Jones et al. |
| 4,166,469 A | 9/1979 | Littleford |
| 4,167,304 A | 9/1979 | Gelbke |
| 4,167,952 A | 9/1979 | Reinicke |
| 4,168,567 A | 9/1979 | Leguy et al. |
| 4,170,280 A | 10/1979 | Schwarz |
| 4,171,218 A | 10/1979 | Hoshino et al. |
| 4,183,124 A | 1/1980 | Hoffman |
| 4,183,247 A | 1/1980 | Allen et al. |
| 4,185,641 A | 1/1980 | Minior et al. |
| 4,186,287 A | 1/1980 | Scott |
| 4,186,749 A | 2/1980 | Fryer |
| 4,186,751 A | 2/1980 | Fleischmann |
| 4,190,057 A | 2/1980 | Hill et al. |
| 4,191,004 A | 3/1980 | Gmuer et al. |
| 4,191,187 A | 3/1980 | Wright et al. |
| 4,192,192 A | 3/1980 | Schnell |
| 4,193,397 A | 3/1980 | Tucker et al. |
| 4,204,547 A | 5/1980 | Allocca |
| 4,206,755 A | 6/1980 | Klein et al. |
| 4,206,761 A | 6/1980 | Cosman |
| 4,206,762 A | 6/1980 | Cosman |
| 4,207,903 A | 6/1980 | O'Neill |
| 4,212,074 A | 7/1980 | Kuno et al. |
| 4,217,221 A | 8/1980 | Masso |
| 4,217,588 A | 8/1980 | Freeny, Jr. |
| 4,220,189 A | 9/1980 | Marquez |
| 4,221,219 A | 9/1980 | Tucker |
| 4,221,523 A | 9/1980 | Eberle |
| 4,223,837 A | 9/1980 | Gubbiotti et al. |
| 4,226,124 A | 10/1980 | Kersten et al. |
| 4,226,229 A | 10/1980 | Eckhart et al. |
| 4,227,533 A | 10/1980 | Godfrey |
| 4,231,376 A | 11/1980 | Lyon et al. |
| 4,232,682 A | 11/1980 | Veth |
| 4,237,900 A | 12/1980 | Schulman et al. |
| 4,241,247 A | 12/1980 | Byrne et al. |
| 4,241,870 A | 12/1980 | Marcus |
| 4,245,593 A | 1/1981 | Stein |
| 4,246,877 A | 1/1981 | Kennedy |
| 4,247,850 A | 1/1981 | Marcus |
| 4,248,238 A | 2/1981 | Joseph et al. |
| 4,248,241 A | 2/1981 | Tacchi |
| 4,256,094 A | 3/1981 | Kapp et al. |
| 4,256,118 A | 3/1981 | Nagel et al. |
| 4,262,343 A | 4/1981 | Claycomb |
| 4,262,632 A | 4/1981 | Hanton et al. |
| 4,265,241 A | 5/1981 | Portner et al. |
| 4,265,252 A | 5/1981 | Chubbuck et al. |
| 4,271,018 A | 6/1981 | Drori |
| 4,273,070 A | 6/1981 | Hoefelmayr et al. |
| 4,274,444 A | 6/1981 | Ruyak |
| 4,275,600 A | 6/1981 | Turner et al. |
| 4,275,913 A | 6/1981 | Marcus |
| 4,278,540 A | 7/1981 | Drori et al. |
| 4,280,036 A | 7/1981 | Fukatsu et al. |
| 4,280,775 A | 7/1981 | Wood |
| 4,281,666 A | 8/1981 | Cosman |
| 4,281,667 A | 8/1981 | Cosman |
| 4,284,073 A | 8/1981 | Krause et al. |
| 4,285,770 A | 8/1981 | Chi et al. |
| 4,291,699 A | 9/1981 | Geddes et al. |
| 4,295,963 A | 10/1981 | Drori et al. |
| 4,297,927 A | 11/1981 | Kuroda et al. |
| 4,303,075 A | 12/1981 | Heilman et al. |
| 4,305,402 A | 12/1981 | Katims |
| 4,312,374 A | 1/1982 | Drori |
| 4,314,480 A | 2/1982 | Becker |
| 4,316,693 A | 2/1982 | Baxter et al. |
| 4,325,387 A | 4/1982 | Helfer |
| 4,327,804 A | 5/1982 | Reed |
| 4,328,654 A | 5/1982 | Van Ginkel et al. |

(56) References Cited

U.S. PATENT DOCUMENTS

| | | |
|---|---|---|
| 4,332,254 A | 6/1982 | Lundquist |
| 4,339,831 A | 7/1982 | Johnson |
| 4,342,218 A | 8/1982 | Fox |
| 4,342,308 A | 8/1982 | Trick |
| 4,346,604 A | 8/1982 | Snook et al. |
| 4,347,851 A | 9/1982 | Jundanian |
| 4,350,647 A | 9/1982 | de la Cruz |
| 4,350,970 A | 9/1982 | von Tomkewitsch et al. |
| 4,351,037 A | 9/1982 | Scherbatskoy |
| 4,351,116 A | 9/1982 | Scott, Jr. |
| 4,356,486 A | 10/1982 | Mount |
| 4,360,010 A | 11/1982 | Finney |
| 4,360,277 A | 11/1982 | Daniel et al. |
| 4,361,153 A | 11/1982 | Slocum et al. |
| 4,363,236 A | 12/1982 | Meyers |
| 4,364,276 A | 12/1982 | Shimazoe et al. |
| 4,365,425 A | 12/1982 | Gotchel |
| 4,368,937 A | 1/1983 | Palombo et al. |
| 4,369,013 A | 1/1983 | Abildgaard et al. |
| 4,373,527 A | 2/1983 | Fischell |
| 4,376,523 A | 3/1983 | Goyen et al. |
| 4,378,809 A | 4/1983 | Cosman |
| 4,380,427 A | 4/1983 | Hehl et al. |
| 4,385,636 A | 5/1983 | Cosman |
| 4,386,422 A | 5/1983 | Mumby et al. |
| 4,387,907 A | 6/1983 | Hiestand et al. |
| 4,392,368 A | 7/1983 | Folkesson et al. |
| 4,393,899 A | 7/1983 | Tsuji et al. |
| 4,393,951 A | 7/1983 | Horst-Rudolf et al. |
| 4,395,232 A | 7/1983 | Koch |
| 4,395,258 A | 7/1983 | Wang et al. |
| 4,395,916 A | 8/1983 | Martin |
| 4,398,983 A | 8/1983 | Suzuki et al. |
| 4,399,705 A | 8/1983 | Weiger et al. |
| 4,399,707 A | 8/1983 | Wamstad |
| 4,399,809 A | 8/1983 | Baro et al. |
| 4,399,821 A | 8/1983 | Bowers |
| 4,403,984 A | 9/1983 | Ash et al. |
| 4,404,968 A | 9/1983 | Evans, Sr. |
| 4,404,974 A | 9/1983 | Titus |
| 4,405,318 A | 9/1983 | Whitney et al. |
| 4,407,125 A | 10/1983 | Parsons et al. |
| 4,407,271 A | 10/1983 | Schiff |
| 4,407,296 A | 10/1983 | Anderson |
| 4,407,326 A | 10/1983 | Wilhelm |
| 4,408,597 A | 10/1983 | Tenney, Jr. |
| 4,408,615 A | 10/1983 | Grossman |
| 4,415,071 A | 11/1983 | Butler et al. |
| 4,416,282 A | 11/1983 | Saulson et al. |
| 4,418,899 A | 12/1983 | Zimmermann et al. |
| 4,419,393 A | 12/1983 | Hanson et al. |
| 4,421,505 A | 12/1983 | Schwartz |
| 4,424,720 A | 1/1984 | Bucchianeri |
| 4,428,228 A | 1/1984 | Banzhaf et al. |
| 4,428,365 A | 1/1984 | Hakky et al. |
| 4,430,899 A | 2/1984 | Wessel et al. |
| 4,431,009 A | 2/1984 | Marino, Jr. et al. |
| 4,431,365 A | 2/1984 | Sturtz, Jr. |
| 4,432,363 A | 2/1984 | Kakegawa et al. |
| 4,435,173 A | 3/1984 | Siposs et al. |
| 4,439,186 A | 3/1984 | Kuhl et al. |
| 4,441,491 A | 4/1984 | Evans, Sr. |
| 4,441,501 A | 4/1984 | Parent |
| 4,444,194 A | 4/1984 | Burcham |
| 4,444,498 A | 4/1984 | Heinemann |
| 4,445,385 A | 5/1984 | Endo |
| 4,446,711 A | 5/1984 | Valente |
| 4,447,224 A | 5/1984 | DeCant, Jr. et al. |
| 4,449,493 A | 5/1984 | Kopec et al. |
| 4,450,811 A | 5/1984 | Ichikawa et al. |
| 4,451,033 A | 5/1984 | Nestegard |
| 4,453,537 A | 6/1984 | Spitzer |
| 4,453,578 A | 6/1984 | Wilder |
| 4,460,835 A | 7/1984 | Masuoka et al. |
| 4,464,170 A | 8/1984 | Clemens et al. |
| 4,465,015 A | 8/1984 | Osta et al. |
| 4,465,474 A | 8/1984 | Mardorf et al. |
| 4,466,290 A | 8/1984 | Frick |
| 4,468,172 A | 8/1984 | Dixon et al. |
| 4,468,762 A | 8/1984 | Jurgens et al. |
| 4,469,365 A | 9/1984 | Marcus et al. |
| 4,471,182 A | 9/1984 | Wielgos et al. |
| 4,471,786 A | 9/1984 | Inagaki et al. |
| 4,473,067 A | 9/1984 | Schiff |
| 4,473,078 A | 9/1984 | Angel |
| 4,476,721 A | 10/1984 | Hochreuther et al. |
| 4,478,213 A | 10/1984 | Redding |
| 4,478,538 A | 10/1984 | Kakino et al. |
| 4,483,196 A | 11/1984 | Kurtz et al. |
| 4,484,135 A | 11/1984 | Ishihara et al. |
| 4,485,813 A | 12/1984 | Anderson et al. |
| 4,489,916 A | 12/1984 | Stevens |
| 4,492,632 A | 1/1985 | Mattson |
| 4,494,411 A | 1/1985 | Koschke et al. |
| 4,494,950 A | 1/1985 | Fischell |
| 4,497,176 A | 2/1985 | Rubin et al. |
| 4,497,201 A | 2/1985 | Allen et al. |
| 4,499,394 A | 2/1985 | Koal |
| 4,499,691 A | 2/1985 | Karazim et al. |
| 4,499,750 A | 2/1985 | Gerber et al. |
| 4,503,678 A | 3/1985 | Wimbush |
| 4,511,974 A | 4/1985 | Nakane et al. |
| 4,513,295 A | 4/1985 | Jones et al. |
| 4,515,004 A | 5/1985 | Jaenson |
| 4,515,750 A | 5/1985 | Pardini et al. |
| 4,516,866 A | 5/1985 | Yamauchi et al. |
| 4,518,637 A | 5/1985 | Takeda et al. |
| 4,519,401 A | 5/1985 | Ko et al. |
| 4,520,443 A | 5/1985 | Yuki et al. |
| 4,522,213 A | 6/1985 | Wallroth et al. |
| 4,527,568 A | 7/1985 | Rickards et al. |
| 4,529,401 A | 7/1985 | Leslie et al. |
| 4,531,526 A | 7/1985 | Genest |
| 4,531,936 A | 7/1985 | Gordon |
| 4,536,000 A | 8/1985 | Rohm et al. |
| 4,537,005 A | 8/1985 | Hoyland et al. |
| 4,537,129 A | 8/1985 | Heinemann et al. |
| 4,538,616 A | 9/1985 | Rogoff |
| 4,540,404 A | 9/1985 | Wolvek |
| 4,542,461 A | 9/1985 | Eldridge et al. |
| 4,544,369 A | 10/1985 | Skakoon et al. |
| 4,545,185 A | 10/1985 | Chikatani et al. |
| 4,546,524 A | 10/1985 | Kreft |
| 4,548,209 A | 10/1985 | Wielders et al. |
| 4,552,150 A | 11/1985 | Zacouto et al. |
| 4,553,226 A | 11/1985 | Scherbatskoy |
| 4,556,063 A | 12/1985 | Thompson et al. |
| 4,557,269 A | 12/1985 | Reynolds et al. |
| 4,557,332 A | 12/1985 | Denison et al. |
| 4,559,815 A | 12/1985 | Needham et al. |
| 4,560,979 A | 12/1985 | Rosskopf et al. |
| 4,561,442 A | 12/1985 | Vollmann et al. |
| 4,562,751 A | 1/1986 | Nason et al. |
| 4,563,175 A | 1/1986 | LaFond |
| 4,565,116 A | 1/1986 | Hehl et al. |
| 4,566,456 A | 1/1986 | Koning et al. |
| 4,569,623 A | 2/1986 | Goldmann |
| 4,570,351 A | 2/1986 | Szanto et al. |
| 4,571,161 A | 2/1986 | Leblanc et al. |
| 4,571,995 A | 2/1986 | Timme |
| 4,573,835 A | 3/1986 | Eckardt et al. |
| 4,574,792 A | 3/1986 | Trick |
| 4,576,181 A | 3/1986 | Wallace et al. |
| 4,576,183 A | 3/1986 | Plicchi et al. |
| 4,577,512 A | 3/1986 | Lowenheck et al. |
| 4,581,018 A | 4/1986 | Jassawalla et al. |
| 4,581,915 A | 4/1986 | Haulsee et al. |
| 4,587,840 A | 5/1986 | Dobler et al. |
| 4,589,805 A | 5/1986 | Duffner et al. |
| 4,592,339 A | 6/1986 | Kuzmak et al. |
| 4,592,340 A | 6/1986 | Boyles |
| 4,593,703 A | 6/1986 | Cosman |
| 4,595,228 A | 6/1986 | Chu |
| 4,596,563 A | 6/1986 | Pande |

(56) References Cited

U.S. PATENT DOCUMENTS

| | | |
|---|---|---|
| 4,599,943 A | 7/1986 | Kobler et al. |
| 4,600,855 A | 7/1986 | Strachan et al. |
| 4,602,541 A | 7/1986 | Benzinger et al. |
| 4,604,089 A | 8/1986 | Santangelo et al. |
| 4,605,354 A | 8/1986 | Daly |
| 4,606,419 A | 8/1986 | Perini |
| 4,606,478 A | 8/1986 | Hack et al. |
| 4,610,256 A | 9/1986 | Wallace |
| 4,614,137 A | 9/1986 | Jones |
| 4,617,016 A | 10/1986 | Blomberg et al. |
| 4,618,861 A | 10/1986 | Gettens et al. |
| 4,620,807 A | 11/1986 | Polit |
| 4,621,331 A | 11/1986 | Iwata |
| 4,622,871 A | 11/1986 | Van Sickle et al. |
| 4,626,462 A | 12/1986 | Kober et al. |
| 4,633,304 A | 12/1986 | Nagasaki et al. |
| 4,633,878 A | 1/1987 | Bombardieri et al. |
| 4,635,182 A | 1/1987 | Hintz |
| 4,637,736 A | 1/1987 | Andeen et al. |
| 4,638,665 A | 1/1987 | Benson et al. |
| 4,644,246 A | 2/1987 | Knapen et al. |
| 4,646,553 A | 3/1987 | Tufte et al. |
| 4,648,363 A | 3/1987 | Kronich |
| 4,648,406 A | 3/1987 | Miller |
| 4,658,358 A | 4/1987 | Leach et al. |
| 4,658,760 A | 4/1987 | Zebuhr |
| 4,660,568 A | 4/1987 | Cosman |
| 4,665,511 A | 5/1987 | Rodney et al. |
| 4,665,896 A | 5/1987 | LaForge et al. |
| 4,669,484 A | 6/1987 | Masters |
| 4,672,974 A | 6/1987 | Lee |
| 4,674,457 A | 6/1987 | Berger et al. |
| 4,674,546 A | 6/1987 | Fournier et al. |
| 4,678,408 A | 7/1987 | Nason et al. |
| 4,681,559 A | 7/1987 | Hooven |
| 4,683,850 A | 8/1987 | Bauder et al. |
| 4,685,463 A | 8/1987 | Williams |
| 4,685,469 A | 8/1987 | Keller et al. |
| 4,685,903 A | 8/1987 | Cable et al. |
| 4,686,987 A | 8/1987 | Salo et al. |
| 4,687,530 A | 8/1987 | Berscheid et al. |
| 4,689,979 A | 9/1987 | Otsuka et al. |
| 4,691,694 A | 9/1987 | Boyd et al. |
| 4,691,710 A | 9/1987 | Dickens et al. |
| 4,693,253 A | 9/1987 | Adams |
| 4,695,237 A | 9/1987 | Inaba et al. |
| 4,696,189 A | 9/1987 | Hochreuther et al. |
| 4,697,574 A | 10/1987 | Karcher et al. |
| 4,698,038 A | 10/1987 | Key et al. |
| 4,700,497 A | 10/1987 | Sato et al. |
| 4,700,610 A | 10/1987 | Bauer et al. |
| 4,701,143 A | 10/1987 | Key et al. |
| 4,703,756 A | 11/1987 | Gough et al. |
| 4,705,507 A | 11/1987 | Boyles |
| 4,706,948 A | 11/1987 | Kroecher et al. |
| 4,712,562 A | 12/1987 | Ohayon et al. |
| 4,718,425 A | 1/1988 | Tanaka et al. |
| 4,722,348 A | 2/1988 | Ligtenberg et al. |
| 4,724,806 A | 2/1988 | Hartwig |
| 4,724,830 A | 2/1988 | Fischell |
| 4,725,826 A | 2/1988 | Hunter |
| 4,728,479 A | 3/1988 | Merkovsky |
| 4,729,517 A | 3/1988 | Krokor et al. |
| 4,730,188 A | 3/1988 | Milheiser |
| 4,730,420 A | 3/1988 | Stratmann et al. |
| 4,730,619 A | 3/1988 | Koning et al. |
| 4,731,058 A | 3/1988 | Doan |
| 4,735,205 A | 4/1988 | Chachques et al. |
| 4,738,267 A | 4/1988 | Lazorthes et al. |
| 4,738,268 A | 4/1988 | Kipnis |
| 4,741,345 A | 5/1988 | Matthews et al. |
| 4,741,732 A | 5/1988 | Crankshaw et al. |
| 4,743,129 A | 5/1988 | Keryhuel et al. |
| 4,745,541 A | 5/1988 | Vaniglia et al. |
| 4,746,830 A | 5/1988 | Holland |
| 4,750,495 A | 6/1988 | Moore et al. |
| 4,752,115 A | 6/1988 | Murray, Jr. et al. |
| 4,752,658 A | 6/1988 | Mack |
| 4,757,463 A | 7/1988 | Ballou et al. |
| 4,759,386 A | 7/1988 | Grouw, III |
| 4,763,649 A | 8/1988 | Merrick |
| 4,765,001 A | 8/1988 | Smith |
| 4,767,406 A | 8/1988 | Wadham et al. |
| 4,769,001 A | 9/1988 | Prince |
| 4,772,896 A | 9/1988 | Nakatsu et al. |
| 4,773,401 A | 9/1988 | Citak et al. |
| 4,774,950 A | 10/1988 | Cohen |
| 4,774,955 A | 10/1988 | Jones |
| 4,777,953 A | 10/1988 | Ash et al. |
| 4,779,626 A | 10/1988 | Peel et al. |
| 4,781,192 A | 11/1988 | Demer |
| 4,782,826 A | 11/1988 | Fogarty |
| 4,783,106 A | 11/1988 | Nutter |
| 4,788,847 A | 12/1988 | Sterghos |
| 4,791,318 A | 12/1988 | Lewis et al. |
| 4,794,803 A | 1/1989 | Osterhout et al. |
| 4,796,641 A | 1/1989 | Mills et al. |
| 4,798,211 A | 1/1989 | Goor et al. |
| 4,798,227 A | 1/1989 | Goodwin |
| 4,799,491 A | 1/1989 | Eckerle |
| 4,799,625 A | 1/1989 | Weaver, Jr. et al. |
| 4,802,488 A | 2/1989 | Eckerle |
| 4,803,987 A | 2/1989 | Calfee et al. |
| 4,804,368 A | 2/1989 | Skakoon et al. |
| 4,807,321 A | 2/1989 | Grasselli et al. |
| 4,808,167 A | 2/1989 | Mann et al. |
| 4,812,823 A | 3/1989 | Dickerson |
| 4,819,656 A | 4/1989 | Spector |
| 4,820,265 A | 4/1989 | DeSatnick et al. |
| 4,820,953 A | 4/1989 | Saubolle et al. |
| 4,821,167 A | 4/1989 | Wiebe |
| 4,821,723 A | 4/1989 | Baker, Jr. et al. |
| 4,823,779 A | 4/1989 | Daly et al. |
| 4,830,006 A | 5/1989 | Haluska et al. |
| 4,832,034 A | 5/1989 | Pizziconi et al. |
| 4,833,384 A | 5/1989 | Munro et al. |
| 4,834,731 A | 5/1989 | Nowak et al. |
| 4,838,857 A | 6/1989 | Strowe et al. |
| 4,840,068 A | 6/1989 | Mayhew, Jr. |
| 4,840,350 A | 6/1989 | Cook et al. |
| 4,844,002 A | 7/1989 | Yasui et al. |
| 4,846,153 A | 7/1989 | Berci |
| 4,846,191 A | 7/1989 | Brockway et al. |
| 4,846,664 A | 7/1989 | Hehl |
| 4,854,328 A | 8/1989 | Pollack |
| 4,863,470 A | 9/1989 | Carter |
| 4,865,587 A | 9/1989 | Walling |
| 4,867,160 A | 9/1989 | Schaldach |
| 4,867,498 A | 9/1989 | Delphia et al. |
| 4,867,618 A | 9/1989 | Brohammer |
| 4,869,252 A | 9/1989 | Gilli |
| 4,870,258 A | 9/1989 | Mochizuki et al. |
| 4,871,351 A | 10/1989 | Feingold |
| 4,872,483 A | 10/1989 | Shah |
| 4,872,869 A | 10/1989 | Johns |
| 4,873,677 A | 10/1989 | Sakamoto et al. |
| 4,875,483 A | 10/1989 | Vollmann et al. |
| 4,880,004 A | 11/1989 | Baker, Jr. et al. |
| 4,882,678 A | 11/1989 | Hollis et al. |
| 4,886,392 A | 12/1989 | Iio et al. |
| 4,895,151 A | 1/1990 | Grevis et al. |
| 4,896,594 A | 1/1990 | Baur et al. |
| 4,898,158 A | 2/1990 | Daly et al. |
| 4,898,578 A | 2/1990 | Rubalcaba, Jr. |
| 4,899,751 A | 2/1990 | Cohen |
| 4,899,752 A | 2/1990 | Cohen |
| 4,902,277 A | 2/1990 | Mathies et al. |
| 4,903,701 A | 2/1990 | Moore et al. |
| 4,909,678 A | 3/1990 | Kakimoto et al. |
| 4,913,147 A | 4/1990 | Fahlstrom et al. |
| 4,919,143 A | 4/1990 | Ayers |
| 4,924,872 A | 5/1990 | Frank |
| 4,926,903 A | 5/1990 | Kawai et al. |
| 4,932,406 A | 6/1990 | Berkovits |

(56) References Cited

U.S. PATENT DOCUMENTS

| | | |
|---|---|---|
| 4,934,369 A | 6/1990 | Maxwell |
| 4,936,304 A | 6/1990 | Kresh et al. |
| 4,940,037 A | 7/1990 | Eckert et al. |
| 4,941,718 A | 7/1990 | Alexander, III et al. |
| 4,942,004 A | 7/1990 | Catanzaro |
| 4,944,050 A | 7/1990 | Shames et al. |
| 4,944,298 A | 7/1990 | Sholder |
| 4,944,307 A | 7/1990 | Hon et al. |
| 4,945,761 A | 8/1990 | Lessi et al. |
| 4,949,724 A | 8/1990 | Mahutte et al. |
| 4,952,205 A | 8/1990 | Mauerer et al. |
| 4,952,928 A | 8/1990 | Carroll et al. |
| 4,953,563 A | 9/1990 | Kaiser et al. |
| 4,954,677 A | 9/1990 | Alberter et al. |
| 4,958,630 A | 9/1990 | Rosenbluth et al. |
| 4,958,645 A | 9/1990 | Cadell et al. |
| 4,960,424 A | 10/1990 | Grooters |
| 4,960,966 A | 10/1990 | Evans et al. |
| 4,967,585 A | 11/1990 | Grimaldo |
| 4,967,761 A | 11/1990 | Nathanielsz |
| 4,970,823 A | 11/1990 | Chen et al. |
| 4,971,251 A | 11/1990 | Dobrick et al. |
| 4,977,896 A | 12/1990 | Robinson et al. |
| 4,978,335 A | 12/1990 | Arthur, III |
| 4,978,338 A | 12/1990 | Melsky et al. |
| 4,979,730 A | 12/1990 | Holbrook et al. |
| 4,980,671 A | 12/1990 | McCurdy |
| 4,981,141 A | 1/1991 | Segalowitz |
| 4,981,173 A | 1/1991 | Perkins et al. |
| 4,981,426 A | 1/1991 | Aoki et al. |
| 4,987,897 A | 1/1991 | Funke et al. |
| 4,988,337 A | 1/1991 | Ito et al. |
| 4,992,794 A | 2/1991 | Brouwers et al. |
| 4,997,556 A | 3/1991 | Yano et al. |
| 5,001,528 A | 3/1991 | Bahraman |
| 5,003,807 A | 4/1991 | Terrell et al. |
| 5,003,975 A | 4/1991 | Hafelfinger et al. |
| 5,003,976 A | 4/1991 | Alt et al. |
| 5,004,472 A | 4/1991 | Wallace |
| 5,004,873 A | 4/1991 | Schnut |
| 5,005,574 A | 4/1991 | Fearnot et al. |
| 5,005,586 A | 4/1991 | Lahr |
| 5,006,844 A | 4/1991 | Ohta et al. |
| 5,007,401 A | 4/1991 | Grohn et al. |
| 5,007,430 A | 4/1991 | Dardik |
| 5,007,919 A | 4/1991 | Silva et al. |
| 5,009,662 A | 4/1991 | Wallace et al. |
| 5,010,893 A | 4/1991 | Sholder |
| 5,012,286 A | 4/1991 | Kawano et al. |
| 5,012,411 A * | 4/1991 | Policastro et al. ............ 600/485 |
| 5,012,810 A | 5/1991 | Strand et al. |
| 5,013,292 A | 5/1991 | Lemay et al. |
| 5,014,040 A | 5/1991 | Weaver et al. |
| 5,019,032 A | 5/1991 | Robertson |
| 5,019,041 A | 5/1991 | Robinson et al. |
| 5,020,845 A | 6/1991 | Falcoff et al. |
| 5,021,046 A | 6/1991 | Wallace |
| 5,022,395 A | 6/1991 | Russie |
| 5,024,965 A | 6/1991 | Chang et al. |
| 5,026,180 A | 6/1991 | Tajima et al. |
| 5,026,360 A | 6/1991 | Johnsen et al. |
| 5,028,918 A | 7/1991 | Giles et al. |
| 5,032,822 A | 7/1991 | Sweet |
| 5,036,869 A | 8/1991 | Inahara |
| 5,038,800 A | 8/1991 | Oba |
| 5,041,086 A | 8/1991 | Koenig et al. |
| 5,041,826 A | 8/1991 | Milheiser |
| 5,042,503 A | 8/1991 | Torok et al. |
| 5,044,770 A | 9/1991 | Haghkar |
| 5,046,661 A | 9/1991 | Kimura et al. |
| 5,048,060 A | 9/1991 | Arai et al. |
| 5,050,922 A | 9/1991 | Falcoff |
| 5,052,910 A | 10/1991 | Hehl et al. |
| 5,053,008 A | 10/1991 | Bajaj |
| 5,057,078 A | 10/1991 | Foote et al. |
| 5,058,583 A | 10/1991 | Geddes et al. |
| 5,061,239 A | 10/1991 | Shiels |
| 5,062,052 A | 10/1991 | Sparer et al. |
| 5,062,053 A | 10/1991 | Shirai et al. |
| 5,062,559 A | 11/1991 | Falcoff |
| 5,064,974 A | 11/1991 | Vigneau et al. |
| 5,067,960 A | 11/1991 | Grandjean et al. |
| 5,068,779 A | 11/1991 | Sullivan et al. |
| 5,069,680 A | 12/1991 | Grandjean et al. |
| 5,077,102 A | 12/1991 | Chong |
| 5,077,870 A | 1/1992 | Melbye et al. |
| 5,078,139 A | 1/1992 | Strand et al. |
| 5,082,006 A | 1/1992 | Jonasson |
| 5,083,563 A | 1/1992 | Collins |
| 5,084,699 A | 1/1992 | DeMichele |
| 5,085,224 A | 2/1992 | Galen et al. |
| 5,085,258 A | 2/1992 | Fink, Jr. et al. |
| 5,089,673 A | 2/1992 | Strzodka et al. |
| 5,089,979 A | 2/1992 | McEachern et al. |
| 5,095,309 A | 3/1992 | Troyk et al. |
| 5,096,271 A | 3/1992 | Portman |
| 5,097,831 A | 3/1992 | Lekholm |
| 5,098,384 A | 3/1992 | Abrams |
| 5,103,832 A | 4/1992 | Jackson |
| 5,105,810 A | 4/1992 | Collins et al. |
| 5,107,850 A | 4/1992 | Olive |
| 5,112,344 A | 5/1992 | Petros et al. |
| 5,113,859 A | 5/1992 | Funke et al. |
| 5,113,869 A | 5/1992 | Nappholz et al. |
| 5,115,676 A | 5/1992 | Lee |
| 5,117,825 A | 6/1992 | Grevious |
| 5,121,777 A | 6/1992 | Leininger et al. |
| 5,127,451 A | 7/1992 | Fink, Jr. et al. |
| 5,129,394 A | 7/1992 | Mehra |
| 5,129,806 A | 7/1992 | Hehl |
| 5,131,145 A | 7/1992 | Badoureaux et al. |
| 5,131,388 A | 7/1992 | Pless et al. |
| 5,133,358 A | 7/1992 | Gustafson et al. |
| 5,135,488 A | 8/1992 | Foote et al. |
| 5,139,484 A | 8/1992 | Hazon et al. |
| 5,144,949 A | 9/1992 | Olson |
| 5,148,580 A | 9/1992 | Dyckow et al. |
| 5,148,695 A | 9/1992 | Ellis |
| 5,152,770 A | 10/1992 | Bengmark et al. |
| 5,152,776 A | 10/1992 | Pinchuk |
| 5,154,170 A | 10/1992 | Bennett et al. |
| 5,154,171 A | 10/1992 | Chirife et al. |
| 5,154,693 A | 10/1992 | East et al. |
| 5,156,972 A | 10/1992 | Issachar et al. |
| 5,158,078 A | 10/1992 | Bennett et al. |
| 5,163,429 A | 11/1992 | Cohen |
| 5,167,615 A | 12/1992 | East et al. |
| 5,168,757 A | 12/1992 | Rabenau et al. |
| 5,168,982 A | 12/1992 | Hakanen et al. |
| 5,171,299 A | 12/1992 | Heitzmann et al. |
| 5,173,873 A | 12/1992 | Wu et al. |
| 5,174,286 A | 12/1992 | Chirife et al. |
| 5,174,291 A | 12/1992 | Schoonen et al. |
| 5,176,502 A | 1/1993 | Sanderson et al. |
| 5,178,197 A | 1/1993 | Healy |
| 5,181,423 A | 1/1993 | Philipps et al. |
| 5,181,517 A | 1/1993 | Hickey |
| 5,184,132 A | 2/1993 | Baird |
| 5,184,614 A | 2/1993 | Collins et al. |
| 5,184,619 A | 2/1993 | Austin |
| 5,185,535 A | 2/1993 | Farb et al. |
| 5,186,224 A | 2/1993 | Schirmacher |
| 5,188,106 A | 2/1993 | Nappholz et al. |
| 5,188,604 A | 2/1993 | Orth |
| 5,192,314 A | 3/1993 | Daskalakis |
| 5,195,362 A | 3/1993 | Eason |
| 5,197,322 A | 3/1993 | Indravudh |
| 5,199,427 A | 4/1993 | Strickland |
| 5,199,428 A | 4/1993 | Obel et al. |
| 5,201,753 A | 4/1993 | Lampropoulos et al. |
| 5,204,670 A | 4/1993 | Stinton |
| 5,207,429 A | 5/1993 | Walmsley et al. |
| 5,209,223 A | 5/1993 | McGorry et al. |
| 5,209,732 A | 5/1993 | Lampropoulos et al. |

(56) References Cited

U.S. PATENT DOCUMENTS

| | | |
|---|---|---|
| 5,211,129 A | 5/1993 | Taylor et al. |
| 5,211,161 A | 5/1993 | Stef et al. |
| 5,212,476 A | 5/1993 | Maloney |
| 5,213,331 A | 5/1993 | Avanzini |
| 5,215,523 A | 6/1993 | Williams et al. |
| 5,218,343 A | 6/1993 | Stobbe et al. |
| 5,218,957 A | 6/1993 | Strickland |
| 5,226,429 A | 7/1993 | Kuzmak |
| 5,226,604 A | 7/1993 | Seiffert et al. |
| 5,230,694 A | 7/1993 | Rosenblum |
| 5,233,985 A | 8/1993 | Hudrlik |
| 5,235,326 A | 8/1993 | Beigel et al. |
| 5,244,269 A | 9/1993 | Harriehausen et al. |
| 5,244,461 A | 9/1993 | Derlien et al. |
| 5,246,008 A | 9/1993 | Mueller et al. |
| 5,249,858 A | 10/1993 | Nusser |
| 5,250,020 A | 10/1993 | Bley |
| 5,254,096 A | 10/1993 | Rondelet et al. |
| 5,256,157 A | 10/1993 | Samiotes et al. |
| 5,263,244 A | 11/1993 | Centa et al. |
| 5,263,981 A | 11/1993 | Polyak et al. |
| 5,267,940 A | 12/1993 | Moulder |
| 5,267,942 A | 12/1993 | Saperston |
| 5,269,891 A | 12/1993 | Colin et al. |
| 5,271,395 A | 12/1993 | Wahlstrand et al. |
| 5,274,859 A | 1/1994 | Redman et al. |
| 5,280,789 A | 1/1994 | Potts |
| 5,282,839 A | 2/1994 | Roline et al. |
| 5,282,840 A | 2/1994 | Hudrlik |
| 5,291,894 A | 3/1994 | Nagy et al. |
| 5,292,219 A | 3/1994 | Merin et al. |
| 5,295,967 A | 3/1994 | Rondelet et al. |
| 5,298,022 A | 3/1994 | Bernardi |
| 5,298,884 A | 3/1994 | Gilmore et al. |
| 5,300,093 A | 4/1994 | Koestner et al. |
| 5,300,120 A | 4/1994 | Knapp et al. |
| 5,304,112 A | 4/1994 | Mrklas et al. |
| 5,305,923 A | 4/1994 | Kirschner et al. |
| 5,312,443 A | 5/1994 | Adams et al. |
| 5,312,452 A | 5/1994 | Salo |
| 5,312,453 A | 5/1994 | Shelton et al. |
| 5,313,953 A | 5/1994 | Yomtov et al. |
| 5,314,451 A | 5/1994 | Mulier |
| 5,314,457 A | 5/1994 | Jeutter et al. |
| 5,324,315 A | 6/1994 | Grevious |
| 5,325,834 A | 7/1994 | Ballheimer et al. |
| 5,326,249 A | 7/1994 | Weissfloch et al. |
| 5,328,460 A | 7/1994 | Lord et al. |
| 5,330,511 A | 7/1994 | Boute et al. |
| 5,337,750 A | 8/1994 | Walloch |
| 5,341,430 A | 8/1994 | Aulia et al. |
| 5,342,401 A | 8/1994 | Spano et al. |
| 5,342,406 A | 8/1994 | Thompson |
| 5,344,388 A | 9/1994 | Maxwell et al. |
| 5,347,476 A | 9/1994 | McBean, Sr. |
| 5,348,210 A | 9/1994 | Linzell et al. |
| 5,348,536 A | 9/1994 | Young et al. |
| 5,350,413 A | 9/1994 | Miller et al. |
| 5,352,180 A | 10/1994 | Candelon et al. |
| 5,353,622 A | 10/1994 | Theener |
| 5,353,800 A | 10/1994 | Pohndorf et al. |
| 5,354,200 A | 10/1994 | Klein et al. |
| 5,354,316 A | 10/1994 | Keimel |
| 5,354,319 A | 10/1994 | Wyborny et al. |
| 5,360,407 A | 11/1994 | Leonard et al. |
| 5,365,462 A | 11/1994 | McBean, Sr. |
| 5,365,619 A | 11/1994 | Solomon |
| 5,365,985 A | 11/1994 | Todd et al. |
| 5,368,040 A | 11/1994 | Carney |
| 5,370,665 A | 12/1994 | Hudrlik |
| 5,373,852 A | 12/1994 | Harrison et al. |
| 5,375,073 A | 12/1994 | McBean |
| 5,377,128 A | 12/1994 | McBean |
| 5,378,231 A | 1/1995 | Johnson et al. |
| 5,382,232 A | 1/1995 | Hague et al. |
| 5,383,915 A | 1/1995 | Adams |
| 5,388,578 A | 2/1995 | Yomtov et al. |
| 5,388,586 A | 2/1995 | Lee et al. |
| 5,388,831 A | 2/1995 | Quadri et al. |
| 5,394,909 A | 3/1995 | Mitchell et al. |
| 5,402,944 A | 4/1995 | Pape et al. |
| 5,406,957 A | 4/1995 | Tansey |
| 5,409,009 A | 4/1995 | Olson |
| 5,411,031 A | 5/1995 | Yomtov |
| 5,411,551 A | 5/1995 | Winston et al. |
| 5,411,552 A | 5/1995 | Andersen et al. |
| 5,416,372 A | 5/1995 | Ljungstroem et al. |
| 5,417,226 A | 5/1995 | Juma |
| 5,417,717 A | 5/1995 | Salo et al. |
| 5,425,362 A | 6/1995 | Siker et al. |
| 5,431,171 A | 7/1995 | Harrison et al. |
| 5,431,694 A | 7/1995 | Snaper et al. |
| 5,433,694 A | 7/1995 | Lim et al. |
| 5,437,605 A | 8/1995 | Helmy et al. |
| 5,443,215 A | 8/1995 | Fackler |
| 5,447,519 A | 9/1995 | Peterson |
| 5,449,368 A | 9/1995 | Kuzmak |
| 5,456,690 A | 10/1995 | Duong-Van |
| 5,461,390 A | 10/1995 | Hoshen |
| 5,464,435 A | 11/1995 | Neumann |
| 5,467,627 A | 11/1995 | Smith et al. |
| 5,474,226 A | 12/1995 | Joseph |
| 5,479,818 A | 1/1996 | Walter et al. |
| 5,482,049 A | 1/1996 | Addiss et al. |
| 5,487,760 A | 1/1996 | Villafana |
| 5,493,738 A | 2/1996 | Sanderson et al. |
| 5,494,036 A | 2/1996 | Uber, III et al. |
| 5,494,193 A | 2/1996 | Kirschner et al. |
| 5,504,474 A | 4/1996 | Libman et al. |
| 5,505,916 A | 4/1996 | Berry, Jr. |
| 5,507,412 A | 4/1996 | Ebert et al. |
| 5,507,737 A | 4/1996 | Palmskog et al. |
| 5,507,785 A | 4/1996 | Deno |
| 5,509,888 A | 4/1996 | Miller |
| 5,509,891 A | 4/1996 | DeRidder |
| 5,513,945 A | 5/1996 | Hartmann et al. |
| 5,514,103 A | 5/1996 | Srisathapat et al. |
| 5,518,504 A | 5/1996 | Polyak |
| 5,520,606 A | 5/1996 | Schoolman et al. |
| 5,523,740 A | 6/1996 | Burgmann et al. |
| 5,534,018 A | 7/1996 | Wahlstrand et al. |
| 5,535,752 A | 7/1996 | Halperin et al. |
| 5,538,005 A | 7/1996 | Harrison et al. |
| 5,541,857 A | 7/1996 | Walter et al. |
| 5,545,140 A | 8/1996 | Conero et al. |
| 5,545,151 A | 8/1996 | O'Connor et al. |
| 5,545,186 A | 8/1996 | Olson et al. |
| 5,545,214 A | 8/1996 | Stevens |
| 5,547,470 A | 8/1996 | Johnson et al. |
| 5,551,427 A | 9/1996 | Altman |
| 5,551,439 A | 9/1996 | Hickey |
| 5,554,185 A | 9/1996 | Block et al. |
| 5,558,644 A | 9/1996 | Boyd et al. |
| 5,564,434 A | 10/1996 | Halperin et al. |
| 5,575,770 A | 11/1996 | Melsky et al. |
| 5,584,803 A | 12/1996 | Stevens et al. |
| 5,586,629 A | 12/1996 | Shoberg et al. |
| 5,593,430 A | 1/1997 | Renger |
| 5,594,665 A | 1/1997 | Walter et al. |
| 5,596,986 A | 1/1997 | Goldfarb |
| 5,597,284 A | 1/1997 | Weltlich et al. |
| 5,610,083 A | 3/1997 | Chan et al. |
| 5,611,768 A | 3/1997 | Tutrone, Jr. |
| 5,612,497 A | 3/1997 | Walter et al. |
| 5,615,671 A | 4/1997 | Schoonen et al. |
| 5,619,991 A | 4/1997 | Sloane |
| 5,625,946 A | 5/1997 | Wildeson et al. |
| 5,626,623 A | 5/1997 | Kieval et al. |
| 5,626,630 A | 5/1997 | Markowitz et al. |
| 5,630,836 A | 5/1997 | Prem et al. |
| 5,634,255 A | 6/1997 | Bishop et al. |
| 5,637,083 A | 6/1997 | Bertrand et al. |
| 5,643,207 A | 7/1997 | Rise |
| 5,645,116 A | 7/1997 | McDonald |

(56) References Cited

U.S. PATENT DOCUMENTS

| | | |
|---|---|---|
| 5,650,766 A | 7/1997 | Burgmann et al. |
| 5,673,585 A | 10/1997 | Bishop et al. |
| 5,676,690 A | 10/1997 | Noren et al. |
| 5,681,285 A | 10/1997 | Ford et al. |
| 5,686,831 A | 11/1997 | Vandervalk et al. |
| 5,687,734 A | 11/1997 | Dempsey et al. |
| 5,693,076 A | 12/1997 | Kaemmerer |
| 5,702,368 A | 12/1997 | Stevens et al. |
| 5,702,427 A | 12/1997 | Ecker et al. |
| 5,702,431 A | 12/1997 | Wang et al. |
| 5,704,352 A | 1/1998 | Tremblay et al. |
| 5,715,786 A | 2/1998 | Seiberth et al. |
| 5,715,837 A | 2/1998 | Chen |
| 5,720,436 A | 2/1998 | Buschor et al. |
| 5,730,101 A | 3/1998 | Aupperle et al. |
| 5,732,710 A | 3/1998 | Rabinovich et al. |
| 5,733,313 A | 3/1998 | Barreras, Sr. et al. |
| 5,738,652 A | 4/1998 | Boyd et al. |
| 5,742,233 A | 4/1998 | Hoffman et al. |
| 5,743,267 A | 4/1998 | Nikolic et al. |
| 5,749,369 A | 5/1998 | Rabinovich et al. |
| 5,749,909 A | 5/1998 | Schroeppel et al. |
| 5,755,687 A | 5/1998 | Donlon |
| 5,755,748 A | 5/1998 | Borza et al. |
| 5,765,568 A | 6/1998 | Sweezer, Jr. et al. |
| 5,769,812 A | 6/1998 | Stevens et al. |
| 5,771,903 A | 6/1998 | Jakobsson |
| 5,782,774 A | 7/1998 | Shmulewitz |
| 5,787,520 A | 8/1998 | Dunbar |
| 5,791,344 A | 8/1998 | Schulman et al. |
| 5,792,094 A | 8/1998 | Stevens et al. |
| 5,792,179 A | 8/1998 | Sideris |
| 5,795,325 A | 8/1998 | Valley et al. |
| 5,796,827 A | 8/1998 | Coppersmith et al. |
| 5,800,375 A | 9/1998 | Sweezer et al. |
| 5,807,265 A | 9/1998 | Itoigawa et al. |
| 5,807,336 A | 9/1998 | Russo et al. |
| 5,810,015 A | 9/1998 | Flaherty |
| 5,810,757 A | 9/1998 | Sweezer, Jr. et al. |
| 5,814,016 A | 9/1998 | Valley et al. |
| 5,817,093 A | 10/1998 | Williamson, IV et al. |
| 5,833,603 A | 11/1998 | Kovacs et al. |
| 5,836,300 A | 11/1998 | Mault |
| 5,836,886 A | 11/1998 | Itoigawa et al. |
| 5,836,982 A * | 11/1998 | Muhlenberg et al. ............ 607/9 |
| 5,840,081 A | 11/1998 | Andersen et al. |
| 5,849,225 A | 12/1998 | Ebina et al. |
| 5,855,597 A | 1/1999 | Jayaraman et al. |
| 5,855,601 A | 1/1999 | Bessler et al. |
| 5,860,938 A | 1/1999 | Lafontaine et al. |
| 5,861,018 A | 1/1999 | Feierbach |
| 5,863,366 A | 1/1999 | Snow |
| 5,868,702 A | 2/1999 | Stevens et al. |
| 5,873,837 A | 2/1999 | Lieber et al. |
| 5,875,953 A | 3/1999 | Shioya et al. |
| 5,879,499 A | 3/1999 | Corvi |
| 5,881,919 A | 3/1999 | Womac et al. |
| 5,885,238 A | 3/1999 | Stevens et al. |
| 5,887,475 A | 3/1999 | Muldner |
| 5,899,927 A | 5/1999 | Ecker et al. |
| 5,908,392 A * | 6/1999 | Wilson et al. ............ 600/509 |
| 5,916,179 A | 6/1999 | Sharrock |
| 5,916,237 A | 6/1999 | Schu |
| 5,935,078 A | 8/1999 | Feierbach |
| 5,938,669 A * | 8/1999 | Klaiber et al. ............ 606/157 |
| 5,951,487 A | 9/1999 | Brehmeier-Flick et al. |
| 5,957,861 A | 9/1999 | Combs et al. |
| 5,967,986 A | 10/1999 | Cimochowski et al. |
| 5,971,934 A | 10/1999 | Scherer et al. |
| 5,974,873 A | 11/1999 | Nelson et al. |
| 5,978,985 A | 11/1999 | Thurman |
| 5,995,874 A | 11/1999 | Borza |
| 6,015,386 A | 1/2000 | Kensey et al. |
| 6,015,387 A | 1/2000 | Schwartz et al. |
| 6,019,729 A | 2/2000 | Itoigawa et al. |
| 6,024,704 A * | 2/2000 | Meador et al. ............ 600/486 |
| 6,030,413 A | 2/2000 | Lazarus |
| 6,035,461 A | 3/2000 | Nguyen |
| 6,047,214 A * | 4/2000 | Mueller et al. ............ 607/61 |
| 6,053,873 A | 4/2000 | Govari et al. |
| 6,056,723 A | 5/2000 | Donlon |
| 6,058,330 A | 5/2000 | Borza et al. |
| 6,059,757 A | 5/2000 | Macoviak et al. |
| 6,067,474 A | 5/2000 | Schulman et al. |
| 6,067,991 A | 5/2000 | Forsell et al. |
| 6,076,016 A | 6/2000 | Feierbach |
| 6,083,174 A | 7/2000 | Brehmeier-Flick et al. |
| 6,090,096 A | 7/2000 | St. Goar et al. |
| 6,102,678 A | 8/2000 | Peclat et al. |
| 6,102,856 A | 8/2000 | Groff et al. |
| 6,102,922 A | 8/2000 | Jakobsson et al. |
| 6,106,477 A | 8/2000 | Miesel et al. |
| 6,106,551 A | 8/2000 | Crossett et al. |
| 6,110,145 A | 8/2000 | Macoviak |
| 6,113,553 A | 9/2000 | Chubbuck |
| 6,131,664 A | 10/2000 | Sonnier |
| 6,135,945 A | 10/2000 | Sultan |
| 6,159,156 A | 12/2000 | Van Bockel et al. |
| 6,162,180 A | 12/2000 | Miesel et al. |
| 6,162,245 A | 12/2000 | Jayaraman |
| 6,168,614 B1 | 1/2001 | Andersen et al. |
| 6,234,745 B1 | 5/2001 | Pugh et al. |
| 6,240,316 B1 | 5/2001 | Richmond et al. |
| 6,240,318 B1 | 5/2001 | Phillips |
| 6,245,102 B1 | 6/2001 | Jayaraman |
| 6,248,080 B1 | 6/2001 | Miesel et al. |
| 6,251,093 B1 | 6/2001 | Valley et al. |
| 6,269,819 B1 | 8/2001 | Oz et al. |
| 6,277,078 B1 | 8/2001 | Porat et al. |
| 6,292,697 B1 | 9/2001 | Roberts |
| 6,309,350 B1 | 10/2001 | VanTassel et al. |
| 6,315,769 B1 | 11/2001 | Peer et al. |
| 6,319,208 B1 | 11/2001 | Abita et al. |
| 6,328,699 B1 | 12/2001 | Eigler et al. |
| 6,338,735 B1 | 1/2002 | Stevens |
| 6,357,438 B1 | 3/2002 | Hansen |
| 6,360,122 B1 | 3/2002 | Fischell et al. |
| 6,360,822 B1 | 3/2002 | Robertson et al. |
| 6,366,817 B1 | 4/2002 | Kung |
| 6,379,308 B1 | 4/2002 | Brockway et al. |
| 6,379,380 B1 | 4/2002 | Satz |
| 6,398,752 B1 | 6/2002 | Sweezer, Jr. et al. |
| 6,409,674 B1 | 6/2002 | Brockway et al. |
| 6,423,031 B1 | 7/2002 | Donlon |
| 6,430,444 B1 | 8/2002 | Borza et al. |
| 6,431,175 B1 | 8/2002 | Penner et al. |
| 6,432,040 B1 | 8/2002 | Meah |
| 6,443,887 B1 | 9/2002 | Derus et al. |
| 6,443,893 B1 | 9/2002 | Schnakenberg et al. |
| 6,450,173 B1 | 9/2002 | Forsell et al. |
| 6,450,946 B1 | 9/2002 | Forsell et al. |
| 6,453,907 B1 | 9/2002 | Forsell et al. |
| 6,454,698 B1 | 9/2002 | Forsell et al. |
| 6,454,699 B1 | 9/2002 | Forsell et al. |
| 6,454,700 B1 | 9/2002 | Forsell et al. |
| 6,454,701 B1 | 9/2002 | Forsell et al. |
| 6,461,292 B1 | 10/2002 | Forsell et al. |
| 6,461,293 B1 | 10/2002 | Forsell et al. |
| 6,463,329 B1 | 10/2002 | Goedeke |
| 6,463,935 B1 | 10/2002 | Forsell et al. |
| 6,464,628 B1 | 10/2002 | Forsell et al. |
| 6,470,212 B1 | 10/2002 | Weijand et al. |
| 6,470,892 B1 | 10/2002 | Forsell et al. |
| 6,471,635 B1 | 10/2002 | Forsell et al. |
| 6,475,136 B1 | 11/2002 | Forsell et al. |
| 6,475,170 B1 | 11/2002 | Doron et al. |
| 6,482,145 B1 | 11/2002 | Forsell |
| 6,482,171 B1 | 11/2002 | Corvi et al. |
| 6,482,177 B1 | 11/2002 | Leinders |
| 6,486,588 B2 | 11/2002 | Doron et al. |
| 6,503,189 B1 | 1/2003 | Forsell et al. |
| 6,504,286 B1 | 1/2003 | Porat et al. |
| 6,531,739 B2 | 3/2003 | Cable et al. |
| 6,533,719 B2 | 3/2003 | Kuyava et al. |

(56) References Cited

U.S. PATENT DOCUMENTS

| | | |
|---|---|---|
| 6,533,733 B1 | 3/2003 | Ericson et al. |
| 6,542,350 B1 | 4/2003 | Rogers |
| 6,558,321 B1 | 5/2003 | Burd et al. |
| 6,558,994 B2 | 5/2003 | Cha et al. |
| 6,573,563 B2 | 6/2003 | Lee et al. |
| 6,582,462 B1 | 6/2003 | Andersen et al. |
| 6,599,250 B2 | 7/2003 | Webb et al. |
| 6,605,112 B1 | 8/2003 | Moll et al. |
| 6,629,534 B1 | 10/2003 | Dell et al. |
| 6,640,137 B2 | 10/2003 | MacDonald |
| 6,641,610 B2 | 11/2003 | Wolf et al. |
| 6,645,143 B2 | 11/2003 | VanTassel et al. |
| 6,673,109 B2 | 1/2004 | Cox |
| 6,678,561 B2 | 1/2004 | Forsell et al. |
| 6,682,480 B1 | 1/2004 | Habib et al. |
| 6,682,503 B1 | 1/2004 | Fariss et al. |
| 6,682,559 B2 | 1/2004 | Myers et al. |
| 6,695,866 B1 | 2/2004 | Kuehn et al. |
| 6,709,385 B2 | 3/2004 | Forsell et al. |
| 6,718,200 B2 | 4/2004 | Marmaropoulos et al. |
| 6,719,787 B2 | 4/2004 | Cox |
| 6,719,788 B2 | 4/2004 | Cox |
| 6,719,789 B2 | 4/2004 | Cox |
| 6,731,976 B2 | 5/2004 | Penn et al. |
| 6,733,525 B2 | 5/2004 | Pease et al. |
| 6,736,846 B2 | 5/2004 | Cox |
| 6,752,813 B2 | 6/2004 | Goldfarb et al. |
| 6,796,942 B1 | 9/2004 | Kreiner et al. |
| 6,822,343 B2 | 11/2004 | Estevez |
| 6,851,628 B1 | 2/2005 | Garrison et al. |
| 6,855,115 B2 | 2/2005 | Fonseca et al. |
| 6,889,772 B2 | 5/2005 | Buytaert et al. |
| 6,890,300 B2 | 5/2005 | Lloyd et al. |
| 6,896,651 B2 | 5/2005 | Gross et al. |
| 6,896,690 B1 | 5/2005 | Lambrecht et al. |
| 6,913,600 B2 | 7/2005 | Valley et al. |
| 6,915,165 B2 | 7/2005 | Forsell et al. |
| 6,926,246 B2 | 8/2005 | Ginggen et al. |
| 6,929,653 B2 | 8/2005 | Strecter |
| 6,932,792 B1 | 8/2005 | St. Goar et al. |
| 6,951,229 B2 | 10/2005 | Garrison et al. |
| 6,951,571 B1 | 10/2005 | Srivastava |
| 6,953,429 B2 | 10/2005 | Forsell et al. |
| 6,961,619 B2 | 11/2005 | Casey |
| 6,970,742 B2 | 11/2005 | Mann et al. |
| 6,979,350 B2 | 12/2005 | Moll et al. |
| 6,985,078 B2 | 1/2006 | Suzuki et al. |
| 6,989,027 B2 | 1/2006 | Allen et al. |
| 7,011,095 B2 | 3/2006 | Wolf et al. |
| 7,011,624 B2 | 3/2006 | Forsell et al. |
| 7,017,583 B2 | 3/2006 | Forsell et al. |
| 7,018,406 B2 | 3/2006 | Seguin et al. |
| 7,021,402 B2 | 4/2006 | Beato et al. |
| 7,025,727 B2 | 4/2006 | Brockway et al. |
| 7,044,920 B2 | 5/2006 | Letort et al. |
| 7,060,080 B2 | 6/2006 | Bachmann et al. |
| 7,081,683 B2 | 7/2006 | Ariav et al. |
| 7,109,933 B2 | 9/2006 | Ito et al. |
| 7,131,447 B2 | 11/2006 | Sterman et al. |
| 7,131,945 B2 | 11/2006 | Fink et al. |
| 7,134,580 B2 | 11/2006 | Garrison et al. |
| 7,144,400 B2 | 12/2006 | Byrum et al. |
| 7,147,640 B2 | 12/2006 | Huebner et al. |
| 7,153,262 B2 | 12/2006 | Stivoric et al. |
| 7,187,978 B2 | 3/2007 | Malek et al. |
| 7,225,032 B2 | 5/2007 | Schmeling et al. |
| 7,257,438 B2 | 8/2007 | Kinast |
| 7,285,090 B2 | 10/2007 | Stivoric et al. |
| 2001/0011543 A1 | 8/2001 | Forsell |
| 2001/0041823 A1 | 11/2001 | Snyder et al. |
| 2002/0049394 A1 | 4/2002 | Roy et al. |
| 2002/0120200 A1 | 8/2002 | Brockway et al. |
| 2002/0138009 A1 | 9/2002 | Brockway et al. |
| 2002/0177782 A1 | 11/2002 | Penner |
| 2002/0193668 A1 * | 12/2002 | Munneke et al. ............ 600/300 |
| 2003/0009201 A1 | 1/2003 | Forsell |
| 2003/0030893 A1 | 2/2003 | Cornelius et al. |
| 2003/0032857 A1 | 2/2003 | Forsell |
| 2003/0037591 A1 | 2/2003 | Ashton et al. |
| 2003/0045775 A1 | 3/2003 | Forsell |
| 2003/0066536 A1 | 4/2003 | Forsell |
| 2003/0088148 A1 | 5/2003 | Forsell |
| 2003/0092962 A1 | 5/2003 | Forsell |
| 2003/0093117 A1 | 5/2003 | Saadat |
| 2003/0100929 A1 | 5/2003 | Forsell |
| 2003/0105385 A1 | 6/2003 | Forsell |
| 2003/0109771 A1 | 6/2003 | Forsell |
| 2003/0114729 A1 | 6/2003 | Forsell |
| 2003/0125605 A1 | 7/2003 | Forsell |
| 2003/0125768 A1 | 7/2003 | Peter |
| 2003/0135089 A1 | 7/2003 | Forsell |
| 2003/0135090 A1 | 7/2003 | Forsell |
| 2003/0136417 A1 | 7/2003 | Fonseca et al. |
| 2003/0144648 A1 | 7/2003 | Forsell |
| 2003/0163079 A1 | 8/2003 | Burnett |
| 2003/0216666 A1 | 11/2003 | Ericson et al. |
| 2004/0054352 A1 | 3/2004 | Adams et al. |
| 2004/0113790 A1 | 6/2004 | Hamel et al. |
| 2004/0133092 A1 | 7/2004 | Kain |
| 2004/0147969 A1 | 7/2004 | Mann et al. |
| 2004/0172087 A1 | 9/2004 | Forsell |
| 2004/0186396 A1 | 9/2004 | Roy et al. |
| 2004/0225462 A1 * | 11/2004 | Renken et al. ............... 702/94 |
| 2004/0254537 A1 | 12/2004 | Conlon et al. |
| 2005/0015014 A1 | 1/2005 | Fonseca et al. |
| 2005/0025979 A1 | 2/2005 | Sandt et al. |
| 2005/0027175 A1 | 2/2005 | Yang |
| 2005/0032511 A1 * | 2/2005 | Malone et al. ............... 455/420 |
| 2005/0038328 A1 | 2/2005 | Stoehrer et al. |
| 2005/0061079 A1 | 3/2005 | Schulman |
| 2005/0102026 A1 | 5/2005 | Turner et al. |
| 2005/0159789 A1 | 7/2005 | Brockway et al. |
| 2005/0165317 A1 | 7/2005 | Turner et al. |
| 2005/0182330 A1 | 8/2005 | Brockway et al. |
| 2005/0187482 A1 | 8/2005 | O'Brien et al. |
| 2005/0187488 A1 | 8/2005 | Wolf |
| 2005/0192642 A1 | 9/2005 | Forsell |
| 2005/0240155 A1 | 10/2005 | Conlon |
| 2005/0240156 A1 | 10/2005 | Conlon |
| 2005/0250979 A1 | 11/2005 | Coe |
| 2005/0267406 A1 | 12/2005 | Hassler |
| 2005/0267500 A1 | 12/2005 | Hassler et al. |
| 2005/0272968 A1 | 12/2005 | Byrum et al. |
| 2005/0277960 A1 | 12/2005 | Hassler et al. |
| 2005/0277974 A1 | 12/2005 | Hassler et al. |
| 2005/0288604 A1 | 12/2005 | Eigler et al. |
| 2005/0288720 A1 | 12/2005 | Ross et al. |
| 2005/0288721 A1 | 12/2005 | Girouard et al. |
| 2005/0288739 A1 | 12/2005 | Hassler et al. |
| 2005/0288740 A1 | 12/2005 | Hassler et al. |
| 2005/0288741 A1 | 12/2005 | Hassler et al. |
| 2005/0288742 A1 | 12/2005 | Giordano et al. |
| 2006/0002035 A1 | 1/2006 | Gao et al. |
| 2006/0010090 A1 | 1/2006 | Brockway et al. |
| 2006/0020224 A1 | 1/2006 | Geiger |
| 2006/0020305 A1 | 1/2006 | Desai et al. |
| 2006/0035446 A1 | 2/2006 | Chang et al. |
| 2006/0047205 A1 | 3/2006 | Ludomirsky et al. |
| 2006/0049714 A1 | 3/2006 | Liu et al. |
| 2006/0058627 A1 | 3/2006 | Flaherty et al. |
| 2006/0064134 A1 | 3/2006 | Mazar et al. |
| 2006/0085051 A1 | 4/2006 | Fritsch |
| 2006/0089571 A1 | 4/2006 | Gertner |
| 2006/0094966 A1 | 5/2006 | Brockway et al. |
| 2006/0100531 A1 | 5/2006 | Moser |
| 2006/0113187 A1 | 6/2006 | Deng et al. |
| 2006/0122285 A1 | 6/2006 | Falloon et al. |
| 2006/0122863 A1 | 6/2006 | Gottesman et al. |
| 2006/0142635 A1 | 6/2006 | Forsell |
| 2006/0149124 A1 | 7/2006 | Forsell |
| 2006/0149324 A1 | 7/2006 | Mann et al. |
| 2006/0149327 A1 | 7/2006 | Hedberg et al. |
| 2006/0157701 A1 | 7/2006 | Bauer et al. |
| 2006/0161186 A1 | 7/2006 | Hassler et al. |

(56) References Cited

U.S. PATENT DOCUMENTS

| | | | |
|---|---|---|---|
| 2006/0173238 A1 | 8/2006 | Starkebaum | |
| 2006/0178617 A1 | 8/2006 | Adams et al. | |
| 2006/0178695 A1 | 8/2006 | Decant et al. | |
| 2006/0183967 A1 | 8/2006 | Lechner | |
| 2006/0184206 A1 | 8/2006 | Baker et al. | |
| 2006/0189887 A1 | 8/2006 | Hassler et al. | |
| 2006/0189888 A1 | 8/2006 | Hassler et al. | |
| 2006/0189889 A1 | 8/2006 | Gertner | |
| 2006/0199997 A1 | 9/2006 | Hassler et al. | |
| 2006/0211912 A1 | 9/2006 | Dlugos et al. | |
| 2006/0211913 A1 | 9/2006 | Dlugos et al. | |
| 2006/0211914 A1 | 9/2006 | Hassler et al. | |
| 2006/0217668 A1 | 9/2006 | Schulze et al. | |
| 2006/0217673 A1 | 9/2006 | Schulze et al. | |
| 2006/0235310 A1 | 10/2006 | O'Brien et al. | |
| 2006/0235439 A1 | 10/2006 | Molitor et al. | |
| 2006/0235448 A1 | 10/2006 | Roslin et al. | |
| 2006/0244914 A1 | 11/2006 | Cech et al. | |
| 2006/0247682 A1 | 11/2006 | Gerber et al. | |
| 2006/0247719 A1 | 11/2006 | Maschino et al. | |
| 2006/0247721 A1 | 11/2006 | Machino | |
| 2006/0247722 A1 | 11/2006 | Maschino et al. | |
| 2006/0247723 A1 | 11/2006 | Gerber et al. | |
| 2006/0247724 A1 | 11/2006 | Gerber et al. | |
| 2006/0247725 A1 | 11/2006 | Gerber et al. | |
| 2006/0252982 A1 | 11/2006 | Hassler et al. | |
| 2006/0293625 A1 | 12/2006 | Hunt et al. | |
| 2006/0293626 A1 | 12/2006 | Byrum et al. | |
| 2006/0293627 A1 | 12/2006 | Byrum et al. | |
| 2007/0010790 A1 | 1/2007 | Byrum et al. | |
| 2007/0027356 A1 | 2/2007 | Ortiz | |
| 2007/0027493 A1 | 2/2007 | Ben-Haim et al. | |
| 2007/0067206 A1 | 3/2007 | Haggerty et al. | |
| 2007/0070906 A1 | 3/2007 | Thakur | |
| 2007/0072452 A1 | 3/2007 | Inagaki et al. | |
| 2007/0081304 A1 | 4/2007 | Takeguchi | |
| 2007/0156013 A1* | 7/2007 | Birk | 600/37 |
| 2007/0161958 A1 | 7/2007 | Glenn | |
| 2007/0167672 A1 | 7/2007 | Dlugos et al. | |
| 2007/0173881 A1 | 7/2007 | Birk et al. | |
| 2007/0179583 A1 | 8/2007 | Goetzinger et al. | |
| 2007/0208313 A1 | 9/2007 | Conlon et al. | |
| 2007/0225781 A1 | 9/2007 | Saadat et al. | |
| 2007/0255335 A1* | 11/2007 | Herbert et al. | 607/40 |
| 2008/0009680 A1 | 1/2008 | Hassler | |

FOREIGN PATENT DOCUMENTS

| | | |
|---|---|---|
| CA | 1275135 | 10/1990 |
| CA | 1277885 | 12/1990 |
| CA | 1317482 | 5/1993 |
| CA | 2082015 | 5/1993 |
| CA | 1327191 | 2/1994 |
| CA | 2119101 | 9/1994 |
| CA | 2305998 | 4/1999 |
| CN | 1059035 | 2/1992 |
| CN | 1119469 | 3/1996 |
| CN | 1241003 | 1/2000 |
| EA | 4581 | 6/2004 |
| EP | 125387 B1 | 11/1984 |
| EP | 417171 | 3/1991 |
| EP | 508141 | 10/1992 |
| EP | 568730 | 11/1993 |
| EP | 605302 | 7/1994 |
| EP | 660482 | 6/1995 |
| EP | 714017 | 5/1996 |
| EP | 769340 | 4/1997 |
| EP | 846475 | 6/1998 |
| EP | 848780 | 6/1998 |
| EP | 876808 | 11/1998 |
| EP | 888079 | 1/1999 |
| EP | 914059 | 5/1999 |
| EP | 981293 | 3/2000 |
| EP | 997680 | 5/2000 |
| EP | 1003021 | 5/2000 |
| EP | 1022983 | 8/2000 |
| EP | 1050265 | 11/2000 |
| EP | 1 115329 | 7/2001 |
| EP | 1119314 | 8/2001 |
| EP | 1128871 | 9/2001 |
| EP | 1202674 | 5/2002 |
| EP | 1213991 | 6/2002 |
| EP | 1253877 | 11/2002 |
| EP | 1253879 | 11/2002 |
| EP | 1253880 | 11/2002 |
| EP | 1253881 | 11/2002 |
| EP | 1253883 | 11/2002 |
| EP | 1253888 | 11/2002 |
| EP | 1255511 | 11/2002 |
| EP | 1255513 | 11/2002 |
| EP | 1255514 | 11/2002 |
| EP | 1263355 | 12/2002 |
| EP | 1263357 | 12/2002 |
| EP | 1284691 | 2/2003 |
| EP | 1374758 | 1/2004 |
| EP | 1488735 | 12/2004 |
| EP | 1500411 | 1/2005 |
| EP | 1510306 | 3/2005 |
| EP | 1518514 | 3/2005 |
| EP | 1545303 | 6/2005 |
| EP | 1547549 | 6/2005 |
| EP | 1563814 | 8/2005 |
| EP | 1568338 | 8/2005 |
| EP | 1582175 | 10/2005 |
| EP | 1582176 | 10/2005 |
| EP | 1584303 | 10/2005 |
| EP | 1586283 | 10/2005 |
| EP | 1591086 | 11/2005 |
| EP | 1593359 | 11/2005 |
| EP | 1598030 | 11/2005 |
| EP | 1609440 | 12/2005 |
| EP | 1674033 | 6/2006 |
| EP | 1736123 | 12/2006 |
| EP | 1799119 | 6/2007 |
| EP | 1832252 A2 | 9/2007 |
| GB | 2355937 | 5/2001 |
| JP | 2001-243698 A | 9/2001 |
| JP | 2004-528104 A | 9/2004 |
| JP | 2004-290548 A | 10/2004 |
| JP | 2007-275583 A | 10/2007 |
| WO | WO-8911244 | 11/1989 |
| WO | WO-8911701 | 11/1989 |
| WO | WO-9004368 | 5/1990 |
| WO | WO-9511057 | 4/1995 |
| WO | WO-9715351 | 5/1997 |
| WO | WO-9733513 | 9/1997 |
| WO | WO-9833554 | 8/1998 |
| WO | WO-9835610 | 8/1998 |
| WO | WO-9901063 | 1/1999 |
| WO | WO-9918850 | 4/1999 |
| WO | WO-0004945 | 2/2000 |
| WO | WO-0033738 | 6/2000 |
| WO | WO-0072899 | 12/2000 |
| WO | WO-014487 | 1/2001 |
| WO | WO-0112075 | 2/2001 |
| WO | WO-0112076 | 2/2001 |
| WO | WO-0112077 | 2/2001 |
| WO | WO-0112078 | 2/2001 |
| WO | WO-0121066 | 3/2001 |
| WO | WO-0136014 | 5/2001 |
| WO | WO-0145485 | 6/2001 |
| WO | WO-0145486 | 6/2001 |
| WO | WO-0147431 | 7/2001 |
| WO | WO-0147432 | 7/2001 |
| WO | WO-0147433 | 7/2001 |
| WO | WO-0147434 | 7/2001 |
| WO | WO-0147435 | 7/2001 |
| WO | WO-0147440 | 7/2001 |
| WO | WO-0147575 | 7/2001 |
| WO | WO-0148451 | 7/2001 |
| WO | WO-0149245 | 7/2001 |
| WO | WO-0150832 | 7/2001 |
| WO | WO-0150833 | 7/2001 |

(56) References Cited

FOREIGN PATENT DOCUMENTS

| | | |
|---|---|---|
| WO | WO-0154626 | 8/2001 |
| WO | WO-0158388 | 8/2001 |
| WO | WO-0158390 | 8/2001 |
| WO | WO-0158391 | 8/2001 |
| WO | WO-0158393 | 8/2001 |
| WO | WO-0160453 | 8/2001 |
| WO | WO-0181890 | 11/2001 |
| WO | WO-0200118 | 1/2002 |
| WO | WO-0215769 | 2/2002 |
| WO | WO-0226161 | 4/2002 |
| WO | WO-02053228 | 7/2002 |
| WO | WO-02055126 | 7/2002 |
| WO | WO-02058551 | 8/2002 |
| WO | WO-02065894 | 8/2002 |
| WO | WO-02076289 | 10/2002 |
| WO | WO-02082984 | 10/2002 |
| WO | WO-02089655 | 11/2002 |
| WO | WO-02090894 | 11/2002 |
| WO | WO-02100481 | 12/2002 |
| WO | WO-03002192 | 1/2003 |
| WO | WO-03002193 | 1/2003 |
| WO | WO-03020182 | 3/2003 |
| WO | WO-03061467 | 7/2003 |
| WO | WO-03061504 | 7/2003 |
| WO | WO-03096889 | 11/2003 |
| WO | WO-2004014456 | 2/2004 |
| WO | WO-2004019773 | 3/2004 |
| WO | WO-2004058101 | 7/2004 |
| WO | WO-2004066879 | 8/2004 |
| WO | WO-2004110263 | 12/2004 |
| WO | WO-2005000206 | 1/2005 |
| WO | WO-2005007075 | 1/2005 |
| WO | WO-2005107583 | 11/2005 |
| WO | WO-2006001851 | 1/2006 |
| WO | WO-2006035446 | 4/2006 |
| WO | WO-2006113187 | 10/2006 |
| WO | WO-2006122285 | 11/2006 |
| WO | WO 2006133735 A1 * | 12/2006 |
| WO | WO-2007067206 | 6/2007 |
| WO | WO-2007070906 | 6/2007 |
| WO | WO-2007072452 | 6/2007 |
| WO | WO-2007081304 | 7/2007 |
| WO | WO-2007104356 | 9/2007 |

OTHER PUBLICATIONS

"Rad Hard Aerospace Components Products", Honeywell product and service information from website http://www.honeywell.com/sites/portal?smap=aerospace&page=Radiation-Hardened-Electronics3&theme=T6&catID=C815147E4-8786-29FE-49EB-C21C8790AA99&id=H0166BA51-5344-E57E-5C37-C6333EA43F61&sel=1; 1 page.

"Radiation Hardened Electronics and Radiation Technology", Honeywell product and service information from website http://www.honeywell.com/sites/portal?smap=aerospace&page=Radiation-Hardened-Electronics&theme=T4; 2 pages.

Kirchner, G., "Honeywell and Synopsys: Concept-to-Parts Solutions for Next Generation Rad-Hard ASICs", in online magazine Compiler, http://www.synopsys.com/news/pubs/compiler/artlead_redasic-apr05.html, Apr. 2005, 5 pages.

P.A. Neukomm and H. Kundig, "Passive Wireless Actuator Control and Sensor Signal Transmission," Sensors and Actuators, A21-A23 (1990) 258-262.

Partial European Search Report, Application No. 09250214.5, Mailed Jul. 6, 2009, 7 pages.

Japanese Office Action for Application No. 2009-015101, issued Apr. 9, 2013. 3 pages.

* cited by examiner

GASTRIC RESTRICTION DEVICE DATA HANDLING DEVICES AND METHODS

FIELD OF THE INVENTION

The present invention relates to devices and methods for handling data related to implantable restriction devices.

BACKGROUND OF THE INVENTION

Obesity is becoming a growing concern, particularly in the United States, as the number of obese people continues to increase and more is learned about the negative health effects of obesity. Morbid obesity, in which a person is 100 pounds or more over ideal body weight, in particular poses significant risks for severe health problems. Accordingly, a great deal of attention is being focused on treating obese patients. One method of treating morbid obesity has been to place a restriction device, such as an elongated band, about the upper portion of the stomach. Gastric bands have typically comprised a fluid-filled elastomeric balloon with fixed endpoints that encircles the stomach just inferior to the esophageal-gastric junction to form a small gastric pouch above the band and a reduced stoma opening in the stomach. When fluid is infused into the balloon, the band expands against the stomach creating a food intake restriction or stoma in the stomach. To decrease this restriction, fluid is removed from the band. The effect of the band is to reduce the available stomach volume and thus the amount of food that can be consumed before becoming "full."

Food restriction devices have also comprised mechanically adjusted bands that similarly encircle the upper portion of the stomach. These bands include any number of resilient materials or gearing devices, as well as drive members, for adjusting the bands. Additionally, gastric bands have been developed that include both hydraulic and mechanical drive elements. An example of such an adjustable gastric band is disclosed in U.S. Pat. No. 6,067,991, entitled "Mechanical Food Intake Restriction Device" which issued on May 30, 2000, and is incorporated herein by reference. It is also known to restrict the available food volume in the stomach cavity by implanting an inflatable elastomeric balloon within the stomach cavity itself. The balloon is filled with a fluid to expand against the stomach walls and, thereby, decrease the available food volume within the stomach.

With each of the above-described food restriction devices, safe, effective treatment requires that the device be regularly monitored and adjusted to vary the degree of restriction applied to the stomach. With banding devices, the gastric pouch above the band will substantially increase in size following the initial implantation. Accordingly, the stoma opening in the stomach must initially be made large enough to enable the patient to receive adequate nutrition while the stomach adapts to the banding device. As the gastric pouch increases in size, the band may be adjusted to vary the stoma size. In addition, it is desirable to vary the stoma size in order to accommodate changes in the patient's body or treatment regime, or in a more urgent case, to relieve an obstruction or severe esophageal dilatation. Traditionally, adjusting a hydraulic gastric band required a scheduled clinician visit during which a Huber needle and syringe were used to penetrate the patient's skin and add or remove fluid from the balloon via an injection port. More recently, implantable pumps have been developed which enable non-invasive adjustments of the band. An external programmer communicates with the implanted pump using telemetry to control the pump. During a scheduled visit, a physician places a hand-held portion of the programmer near the gastric implant and transmits power and command signals to the implant. The implant in turn adjusts the fluid levels in the band and transmits a response command to the programmer.

During these gastric band adjustments, it has been difficult to determine how the adjustment is proceeding, and whether the adjustment will have the intended effect. In an attempt to determine the efficacy of an adjustment, some physicians have utilized fluoroscopy with a Barium swallow as the adjustment is being performed. However, fluoroscopy is both expensive and undesirable due to the radiation doses incurred by both the physician and patient. Other physicians have instructed the patient to drink a glass of water during or after the adjustment to determine whether the water can pass through the adjusted stoma. This method, however, only assures that the patient is not obstructing, and does not provide any information about the efficacy of the adjustment. Oftentimes, a physician may simply adopt a "try as you go" method based upon their prior experience, and the results of an adjustment may not be discovered until hours or days later, when the patient experiences a complete obstruction to the stomach cavity, or the band induces erosion of the stomach tissue due to excessive interface pressures against the band.

Additionally, it can be advantageous to acquire data indicating the pressure in a gastric band before, during, and/or after pressure adjustment for adjustment, diagnostic, monitoring, or other purposes. It can be further advantageous to store such pressure data and/or communicate it to an external location. However, data storage space can be limited, and power to communicate data can be resource-intensive.

Accordingly, methods and devices are provided for use with a gastric restriction device, and in particular for handling data gathered in relation to a gastric restriction device.

SUMMARY OF THE INVENTION

The present invention generally provides devices and methods for handling data related to implantable restriction devices. In one embodiment, a restriction system for forming a restriction in a patient is provided that includes an implantable restriction device that can form a restriction in a patient and an implantable sensing device in communication with the implantable restriction device. The implantable sensing device can sense a parameter related to the implantable restriction device and communicate a selected portion of data to an external device considering a variation of data from a nominal parameter value related to the implantable restriction device. The parameter can include at least one of, for example, pulse count, pulse width, and amplitude. In some embodiments, the selected portion of data is compressed prior to communication of the selected portion of data to the external device.

The sensing device can be implemented in a variety of ways. For example, the sensing device can communicate data to the external device when the external device telemetrically provides at least some power to the sensing device. As another example, the sensing device can discard data that substantially equals a nominal value. For yet another example, the sensing device can communicate a selected portion of data based on whether the data includes a value within a defined range of values. As still another example, the sensing device can compare data with a nominal value. For another example, the sensing device can store the selected portion of data prior to communication of the selected portion of data to the external device.

In another embodiment, a restriction system for forming a restriction in a patient includes an implantable restriction device that can form a restriction in a patient, an implantable pressure sensing device in communication with the implantable restriction device that can sense a pressure within the implantable restriction device, and a processor (which can be included in the implantable pressure sensing device) that can determine whether to store any of the sensed pressure data prior to communicating any of the sensed pressure data to an external reading device. The processor, in some embodiments, can have a download of stored data to the external reading device triggered when the external reading device is moved in proximity of the implantable pressure sensing device. In some embodiments, the system can also include an external storage mechanism that can store sensed pressure data, communicate stored pressure data to an external device, and, optionally, be removably attached to the patient.

In other aspects, a method of forming a restriction in a patient is provided. The method includes using an implantable pressure sensing device to obtain pressure data related to a pressure within an implantable restriction device that can form a restriction in a patient, storing at least a portion of obtained pressure data at the implantable pressure sensing device, and triggering a download of stored pressure data when an external device is moved in proximity of the implantable pressure sensing device. The obtained pressure data stored at the implantable pressure sensing device can include pressure values that exceed a nominal pressure within the implantable restriction device. In some embodiments, the method can also include compressing at least a portion of obtained pressure data prior to storing the at least a portion of the obtained pressure data at the implantable pressure sensing device. The compression can be performed using at least one compression technique, such as storing difference values, using a quantization table, using run-length coding, and using Huffman coding.

In another embodiment, a method of forming a restriction in a patient includes obtaining pressure data related to a pressure within an implantable restriction device that can form a restriction in a patient. In some embodiments, obtaining pressure data includes reducing a rate of pressure data gathering during a determined period. The method further includes determining a portion of the pressure data to retain prior to communicating pressure data to an external reading device. Determining a portion of the pressure data to retain can include determining if any of the obtained pressure data includes a value within a defined range of pressure values, determining to retain any of the obtained pressure data that exceeds a nominal pressure within the implantable restriction device, and/or processing the obtained pressure data using a pressure sensing device (e.g., a processor) coupled to the implantable restriction device and configured to obtain the pressure data. An alert for communication to the external reading device can be generated if any of the obtained pressure data includes a value that exceeds a threshold pressure value. In some embodiments, the method also includes storing only the portion of the pressure data determined to be retained prior to communicating pressure data to the external reading device. In still other embodiments, the method also includes compressing the portion of the pressure data determined to be retained prior to storing the portion of the pressure data determined to be retained.

In yet another embodiment, a method of forming a restriction in a patient includes using an implantable pressure sensing device to obtain pressure data related to a pressure within an implantable restriction device that can form a restriction in a patient, storing the obtained pressure data at the implantable pressure sensing device, and compressing the obtained pressure data prior to storing the obtained pressure data. The obtained pressure data can be compressed using at least one compression technique, such as storing difference values, using a quantization table, using run-length coding, and using Huffman coding. The method can also include communicating at least a portion of the compressed and stored pressure data from the pressure sensing device to an external device.

BRIEF DESCRIPTION OF THE DRAWINGS

The invention will be more fully understood from the following detailed description taken in conjunction with the accompanying drawings, in which.

DETAILED DESCRIPTION OF THE INVENTION

Certain exemplary embodiments will now be described to provide an overall understanding of the principles of the structure, function, manufacture, and use of the devices and methods disclosed herein. One or more examples of these embodiments are illustrated in the accompanying drawings. Those skilled in the art will understand that the devices and methods specifically described herein and illustrated in the accompanying drawings are non-limiting exemplary embodiments and that the scope of the present invention is defined solely by the claims. The features illustrated or described in connection with one exemplary embodiment may be combined with the features of other embodiments. Such modifications and variations are intended to be included within the scope of the present invention.

The present invention generally provides devices and methods for handling data related to implantable restriction devices. In general, the devices and methods allow collection, analysis, storage, and transmission of measurements related to any parameter related to implantable restriction devices, such as pressure, pulse count, pulse width, and amplitude. While the methods and devices discussed herein can relate to any sensed data parameter, in an exemplary embodiment, the measurements relate to pressure. Pressure measurements can help accurately evaluate the performance of and determine any advisable pressure adjustments of an implantable restriction device, but not all collected pressure data may be helpful in making such evaluations and determinations. Furthermore, handling pressure measurement data can drain power resources of an implantable restriction system and can use costly, physically bulky, and electronically large data storage space. Pressure measurement data can be compressed before storing it, thereby using less storage space, time, power, and/or bandwidth for communication than for the corresponding, uncompressed data. Pressure measurement data can also be compressed prior to communication. The data can be compressed and directly transmitted, or the compressed data stored in memory can be recalled and communicated wirelessly when interrogated. Additionally, not all pressure data need be recorded or retained. Not recording or retaining all pressure data, such as data substantially equaling a resting or nominal pressure of the implantable restriction device indicative of little to no pressure variation and data indicative of isolated, non-recurring events, can save storage space for potentially more analytically valuable pressure measurement data and reduce the amount of physical and/or electronic storage space used for pressure measurements. Any pressure measurement data that is recorded can be transmitted to an external device using power telemetrically provided or inductively coupled by the external device, thereby reducing or eliminating power supply resources local to the storage location of recorded data.

Figure 1A:
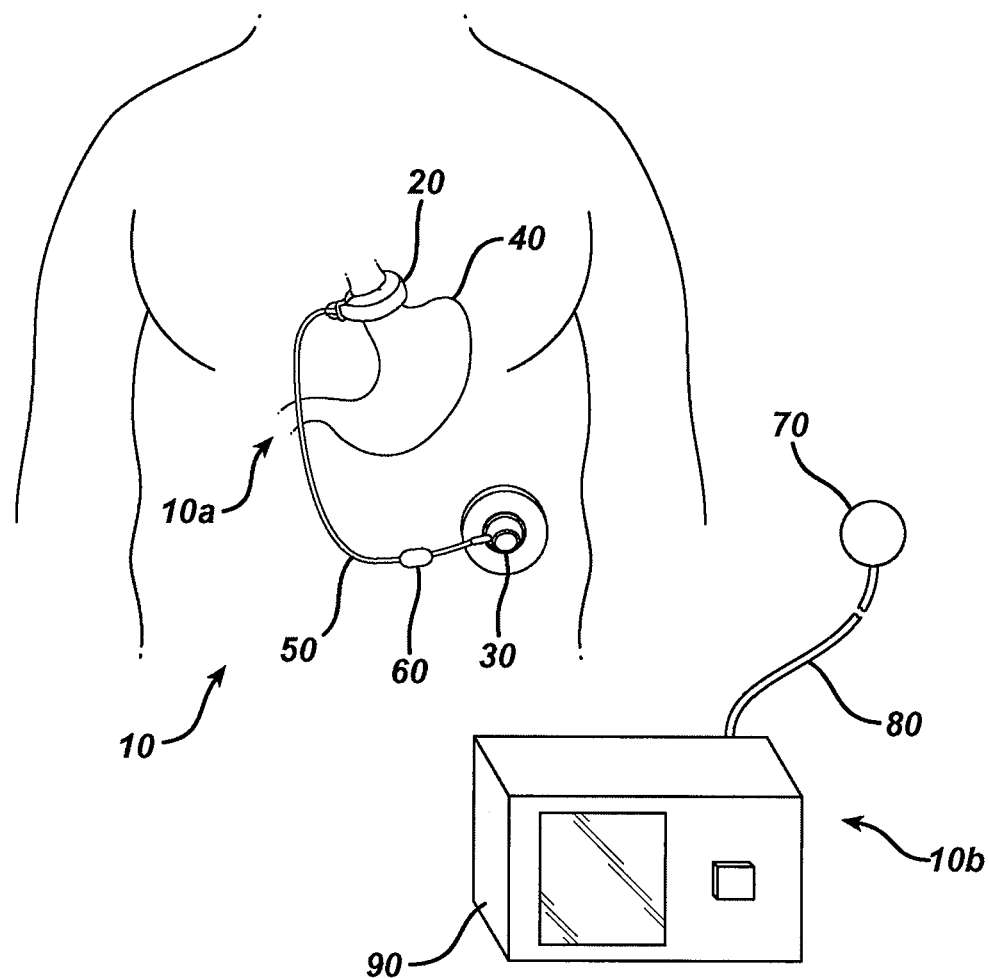
FIG. 1A is a schematic diagram of an embodiment of a food intake restriction system.
Figure 1B:
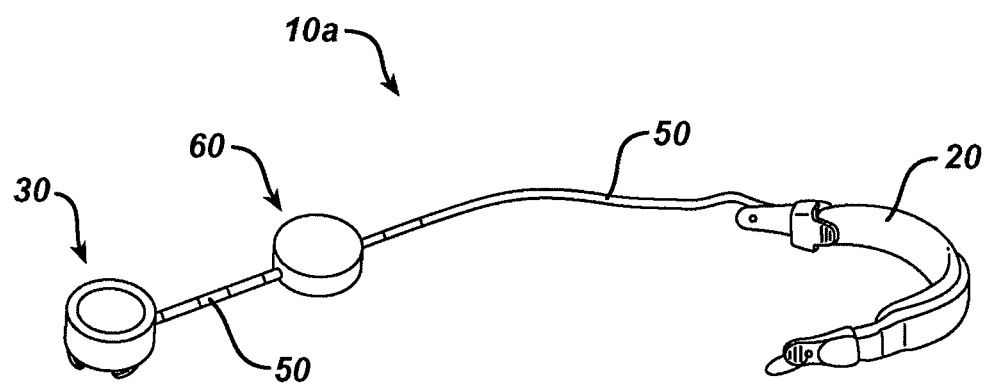
FIG. 1B is a perspective view of an embodiment of an implantable portion of the food intake restriction system of FIG. 1A.

While the present invention can be used with a variety of restriction systems known in the art, FIG. 1A illustrates one exemplary embodiment of a food intake restriction system 10 in use in a patient. As shown, the system 10 generally includes an implantable portion 10a and an external portion 10b. FIG. 1B illustrates the implantable portion 10a outside of a patient. As shown, the implantable portion 10a includes an adjustable gastric band 20 that is configured to be positioned around the upper portion of a patient's stomach 40, and an injection port housing 30 that is fluidly coupled to the adjustable gastric band 20, e.g., via a catheter 50. The injection port 30 is adapted to allow fluid to be introduced into and removed from the gastric band 20 to thereby adjust the size of the band 20 and thus the pressure applied to the stomach 40. The injection port 30 can thus be implanted at a location within the body that is accessible through tissue. Typically, injection ports are positioned in the lateral subcostal region of the patient's abdomen under the skin and layers of fatty tissue. Surgeons also typically implant injection ports on the sternum of the patient.

The internal portion 10a can also include a sensing or measuring device that is in fluid communication with the closed fluid circuit in the implantable portion 10a. In one embodiment, the sensing device is a pressure sensing device configured to measure the fluid pressure of the closed fluid circuit. While the pressure measuring device can have various configurations and it can be positioned anywhere along the internal portion 10a, including within the injection port 30 and as described further below, in the illustrated embodiment the pressure measuring device is in the form of a pressure sensor that is disposed within a sensor housing 60 positioned adjacent to the injection port 30. The catheter 50 can include a first portion that is coupled between the gastric band 20 and the pressure sensor housing 60, and a second portion that is coupled between the pressure sensor housing 60 and the injection port 30. While it is understood that the sensing device can be configured to obtain data relating to one or more relevant parameters, generally it will be described herein in a context of a pressure sensing device.

In addition to sensing pressure of fluid within the internal portion 10a as described herein, pressure of fluid within the esophagus and/or the stomach 40 can also be sensed using any suitable device, such as an endoscopic manometer. By way of non-limiting example, such fluid pressure measurements can be compared against measured pressure of fluid within the internal portion 10a before, during, and/or after adjustment of pressure within the internal portion 10a. Other suitable uses for measured pressure within the esophagus and/or the stomach 40 will be appreciated by those skilled in the art.

As further shown in FIG. 1A, the external portion 10b generally includes a data reading device 70 that is configured to be positioned on the skin surface above the sensor housing 60 (which can be implanted beneath thick tissue, e.g., over 10 cm thick) to non-invasively communicate with the sensor housing 60 and thereby obtain data (e.g., pressure) measurements. The data reading device 70 can optionally be electrically coupled (wirelessly or wired, as in this embodiment via an electrical cable assembly 80) to a control box 90 that can display the pressure measurements and/or other data obtained from the data reading device 70. While shown in this example as located local to the patient, the control box 90 can be at a location local to or remote from the patient, as explained further below.

Figure 2A:
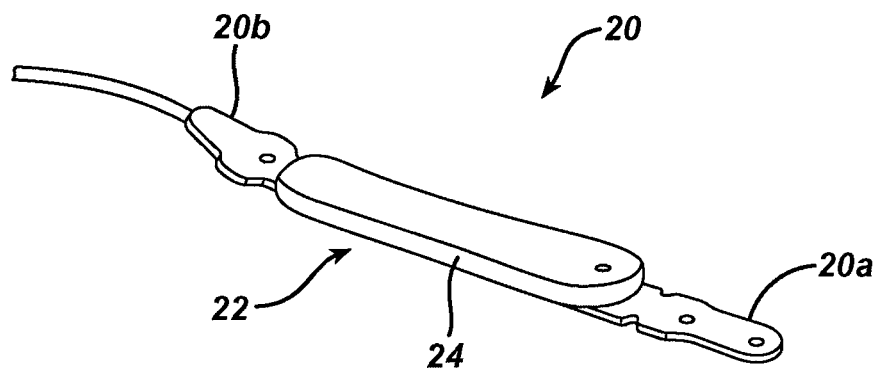
FIG. 2A is a perspective view of the food intake restriction device of FIG. 1A.

FIG. 2A shows the gastric band 20 in more detail. While the gastric band 20 can have a variety of configurations, and various gastric bands currently known in the art can be used with the present invention, in the illustrated embodiment the gastric band 20 has a generally elongate shape with a support structure 22 having first and second opposite ends 20a, 20b that can be formed in a loop such that the ends are secured to each other. Various mating techniques can be used to secure the ends 20a, 20b to one another. In the illustrated embodiment, the ends 20a, 20b are in the form of straps that mate together, with one laying on top of the other. In another embodiment, illustrated, for example, in FIGS. 1B and 2B, a support structure at one end of the gastric band 20 can include an opening through which the other end of the gastric band 20 can feed through to secure the ends to one another. The gastric band 20 can also include a variable volume member, such as an inflatable balloon 24, that is disposed or formed on one side of the support structure 22 and that is configured to be positioned adjacent to tissue. The balloon 24 can expand or contract against the outer wall of the stomach to form an adjustable stoma for controllably restricting food intake into the stomach.

A person skilled in the art will appreciate that the gastric band can have a variety of other configurations. Moreover, the various methods and devices disclosed herein have equal applicability to other types of implantable bands. For example, bands are used for the treatment of fecal incontinence, as described in U.S. Pat. No. 6,461,292 which is hereby incorporated by reference. Bands can also be used to treat urinary incontinence, as described in U.S. Publication No. 2003/0105385 which is hereby incorporated by reference. Bands can also be used to treat heartburn and/or acid reflux, as disclosed in U.S. Pat. No. 6,470,892 which is hereby incorporated by reference. Bands can also be used to treat impotence, as described in U.S. Publication No. 2003/0114729 which is hereby incorporated by reference.

Figure 2B:
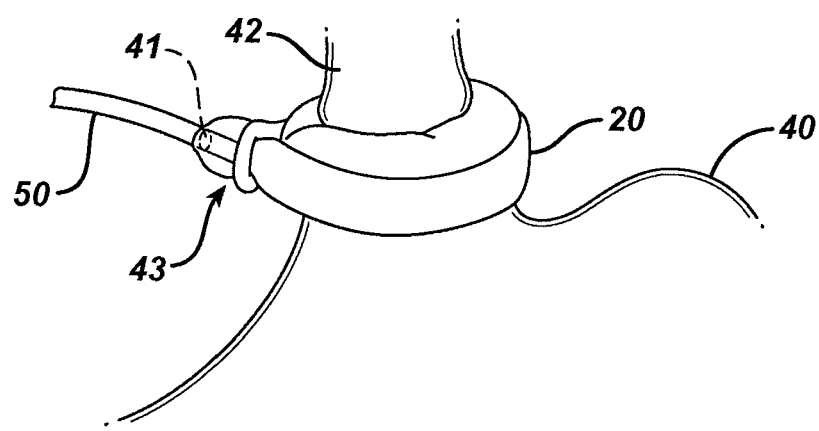
FIG. 2B is a schematic diagram of the food intake restriction device of FIG. 2A applied about the gastro-esophageal junction of a patient.

FIG. 2B shows the adjustable gastric band 20 applied about the gastro-esophageal junction of a patient. As shown, the band 20 at least substantially encloses the upper portion of the stomach 40 near the junction with the patient's esophagus 42. After the band 20 is implanted, preferably in the deflated configuration wherein the band 20 contains little or no fluid, the band 20 can be inflated, e.g., using saline, to decrease the size of the stoma opening. A person skilled in the art will appreciate that various techniques, including mechanical and electrical techniques, can be used to adjust the band 20. FIG. 2B also shows an alternate location of a pressure sensor 41, disposed in a buckle 43 of the band 20.

Figure 3:
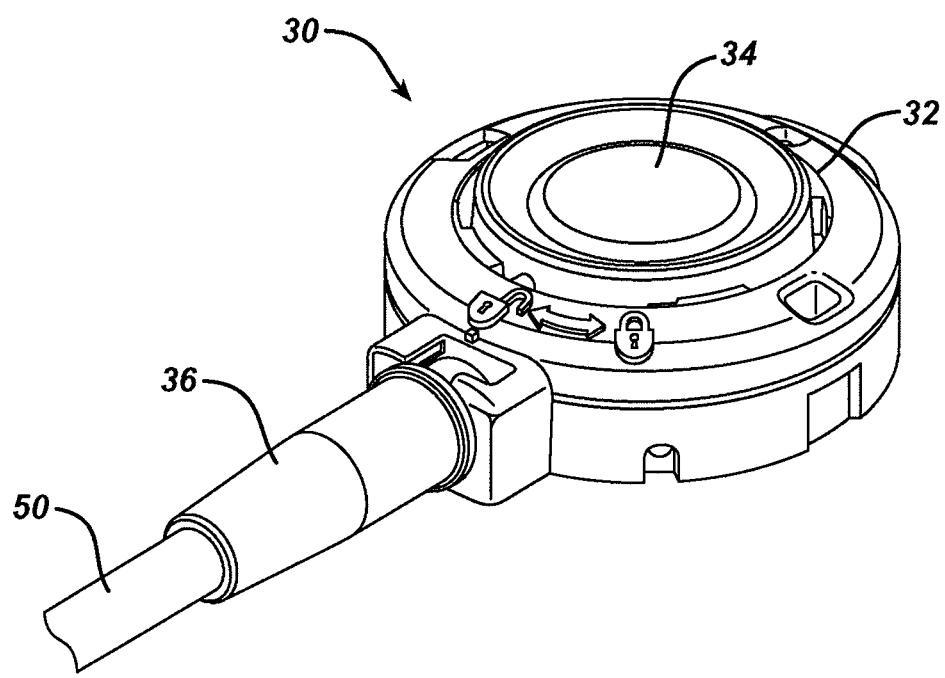
FIG. 3 is a perspective view of an embodiment of the injection port housing of FIG. 1A.

The fluid injection port 30 can also have a variety of configurations. In the embodiment shown in FIG. 3, the injection port 30 has a generally cylindrical housing with a distal or bottom surface and a perimeter wall extending proximally from the bottom surface and defining a proximal opening 32. The proximal opening 32 can include a needle-penetrable septum 34 extending there across and providing access to a fluid reservoir (not visible in FIG. 3) formed within the housing. The septum 34 is preferably placed in a proximal enough position such that the depth of the reservoir is sufficient enough to expose the open tip of a needle, such as a Huber needle, so that fluid transfer can take place. The septum 34 is preferably arranged so that it will self seal after being punctured by a needle and the needle is withdrawn. As further shown in FIG. 3, the port 30 can further include a catheter tube connection member 36 that is in fluid communication with the reservoir and that is configured to couple to a catheter (e.g., the catheter 50). A person skilled in the art will appreciate that the housing can be made from any number of materials, including stainless steel, titanium, or polymeric materials, and the septum 34 can likewise be made from any number of materials, including silicone.

The reading device 70 can also have a variety of configurations, and one exemplary pressure reading device is disclosed in more detail in commonly-owned U.S. Publication No. 2006/0189888 and U.S. Publication No. 2006/0199997, which are hereby incorporated by reference. In general, the data reading device 70 can non-invasively measure the pressure of the fluid within the implanted portion 10a even when the pressure sensing device is implanted beneath thick (at least over 10 cm) subcutaneous fat tissue. The physician can hold the reading device 70 against the patient's skin near the location of the sensor housing 60, and/or other pressure sensing device location(s), and observe the pressure reading on a display on the control box 90. The data reading device 70 can also be removably attached to the patient, as discussed further below, such as during a prolonged examination, using straps, adhesives, and other well-known methods. The data reading device 70 can operate through conventional cloth or paper surgical drapes, and can also include a disposal cover (not shown) that may be replaced for each patient.

Figure 4:
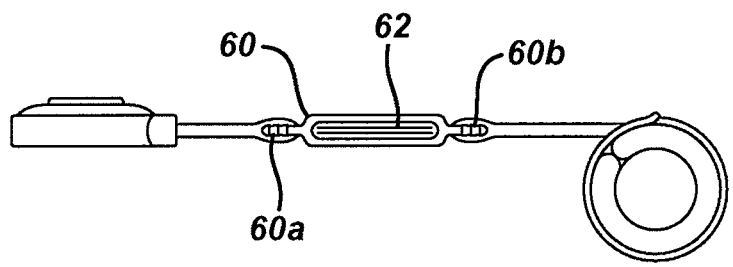
FIG. 4 is a perspective view of an embodiment of the sensor housing of FIG. 1A.

As indicated above, the system 10 can also include a pressure measuring device in communication with the closed fluid circuit and configured to measure pressure (e.g., fluid pressure) which corresponds to the amount of restriction applied by the adjustable gastric band 20 to the patient's stomach 40. Measuring the pressure enables a person (e.g., a physician, a nurse, a patient, etc.) to evaluate the efficacy and functionality of the restriction created by a band adjustment. In the illustrated embodiment, as shown in FIG. 4, the pressure measuring device is in the form of a pressure sensor 62 disposed within the sensor housing 60. The pressure measuring device can, however, be disposed anywhere within the closed hydraulic circuit of the implantable portion, and various exemplary locations and configurations are disclosed in more detail in commonly-owned U.S. Publication No. 2006/0211913 entitled "Non-Invasive Pressure Measurement In a Fluid Adjustable Restrictive Device," filed on Mar. 7, 2006, and hereby incorporated by reference. In general, the illustrated sensor housing 60 includes an inlet 60a and an outlet 60b that are in fluid communication with the fluid in the implantable portion 10a. An already-implanted catheter 50 can be retrofitted with the sensor housing 60, such as by severing the catheter 50 and inserting barbed connectors (or any other connectors, such as clamps, clips, adhesives, welding, etc.) into the severed ends of the catheter 50. The sensor 62 can be disposed within the housing 60 and be configured to respond to fluid pressure changes within the hydraulic circuit and convert the pressure changes into a usable form of data.

Various pressure sensors known in the art can be used as the pressure sensor 62, such as a wireless pressure sensor provided by CardioMEMS, Inc. of Atlanta, Ga., though a suitable MEMS pressure sensor may be obtained from any other source, including but not limited to Integrated Sensing Systems, Inc. (ISSYS) of Ypsilanti, Mich. and Remon Medical Technologies, Inc. of Waltham, Mass. One exemplary MEMS pressure sensor is described in U.S. Pat. No. 6,855,115, the disclosure of which is incorporated by reference herein for illustrative purposes only. It will also be appreciated by a person skilled in the art that suitable pressure sensors can include, but are not limited to, capacitive, piezoresistive, silicon strain gauge, or ultrasonic (acoustic) pressure sensors, as well as various other devices capable of measuring pressure.

Figure 5:
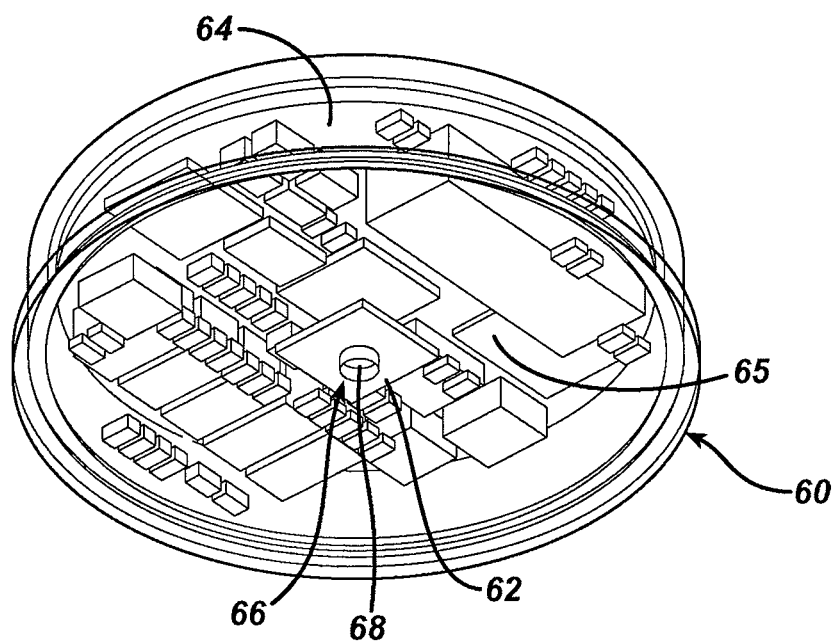
FIG. 5 illustrates an embodiment of the sensor housing of FIG. 1A.

One embodiment of a configuration of the sensor housing 60 having the sensor 62 disposed within it is shown in FIG. 5. The sensor housing 60 in this example includes a motherboard that can serve as a hermetic container to prevent fluid from contacting any elements disposed within the sensor housing 60, except as discussed for the sensor 62. The sensor housing 60 can be made from any biocompatible material appropriate for use in a body, such as a polymer, biocompatible metal, and other similar types of material. Furthermore, the sensor housing 60 can be made from any one or more of transparent (as shown in FIG. 5), opaque, semi-opaque, and radio-opaque materials. A circuit board 64 including, among other elements, a microcontroller 65 (e.g., a processor), can also be disposed within the housing 60 to help process and communicate pressure measurements gathered by the sensor 62, and also possibly other data related to the band 20. As further discussed below, the circuit board 64 can also include a transcutaneous energy transfer (TET)/telemetry coil and a capacitor. Optionally, a temperature sensor can be integrated into the circuit board 64. The microcontroller 65, the TET/telemetry coil, the capacitor, and/or the temperature sensor can be in communication via the circuit board 64 or via any other suitable component(s). The TET/telemetry coil and capacitor can collectively form a tuned tank circuit for receiving power from the external portion 10b, and transmitting pressure measurements to a pressure reading device, e.g., the reading device 70. Moreover, to the extent that a telemetry component associated with the pressure sensor 62 is unable to reach a telemetry device external to the patient without some assistance, such assistance can be provided by any suitable number of relays (not shown) or other devices.

Fluid can enter the sensor housing 60 through an opening 66 located anywhere on the housing's surface (here, its bottom surface) and come into contact with a pressure sensing surface 68 of the sensor 62. The sensor 62 is typically hermetically sealed to the motherboard such that fluid entering the opening 66 cannot infiltrate and affect operation of the sensor 62 except at the pressure sensing surface 68. The sensor 62 can measure the pressure of fluid coming into contact with the pressure sensing surface 68 as fluid flows in and out of the opening 66. For example, the pressure sensing surface 68 can include a diaphragm having a deformable surface such that when fluid flows through the opening 66, the fluid impacts the surface of the diaphragm, causing the surface to mechanically displace. The mechanical displacement of the diaphragm can be converted to an electrical signal by a variable resistance circuit including a pair of variable resistance, silicon strain gauges. One strain gauge can be attached to a center portion of diaphragm to measure the displacement of the diaphragm, while the second, matched strain gauge can be attached near the outer edge of diaphragm. The strain gauges can be attached to the diaphragm with adhesives or can be diffused into the diaphragm structure. As fluid pressure within band 20 fluctuates, the surface of the diaphragm can deform up or down, thereby producing a resistance change in the center strain gauge.

Figure 6:
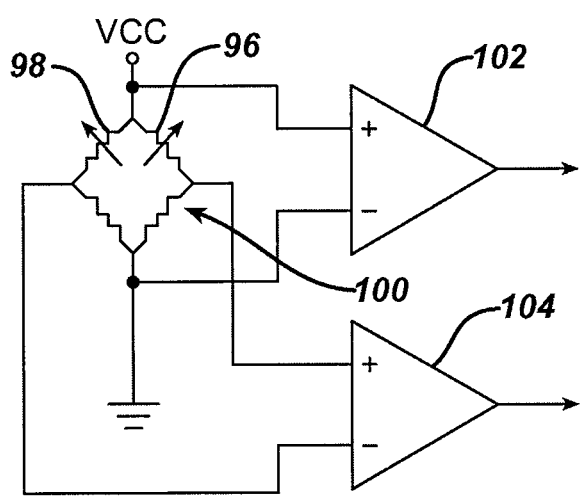
FIG. 6 is a schematic of an embodiment of a variable resistance circuit for the pressure sensor of FIG. 5.

One embodiment of a variable resistance circuit for the sensor 62 is shown in FIG. 6. The circuit includes first and second strain gauges 96, 98 that form the top two resistance elements of a half-compensated, Wheatstone bridge circuit 100. As the first strain gauge 96 reacts to the mechanical displacements of the sensor's diaphragm, the changing resistance of the first gauge 96 changes the potential across the top portion of the bridge circuit 100. The second strain gauge 98 is matched to the first strain gauge 96 and athermalizes the Wheatstone bridge circuit 100. First and second differential amplifiers 102, 104 are connected to the bridge circuit 100 to measure the change in potential within the bridge circuit 100 due to the variable resistance strain gauges 96, 98. In particular, the first differential amplifier 102 measures the voltage across the entire bridge circuit 100, while the second differential amplifier 104 measures the differential voltage across the strain gauge half of bridge circuit 100. The greater the differential between the strain gauge voltages, for a fixed voltage across the bridge, the greater the pressure difference. Output signals from the differential amplifiers 102, 104 can be applied to the microcontroller 65 integrated into the circuit board 64, and the microcontroller 65 can transmit the measured pressure data to a device external to the patient. If desired, a fully compensated Wheatstone bridge circuit can also be used to increase the sensitivity and accuracy of the pressure sensor 62. In a fully compensated bridge circuit, four strain gauges are attached to the surface of diaphragm rather than only two strain gauges.

Figure 7:
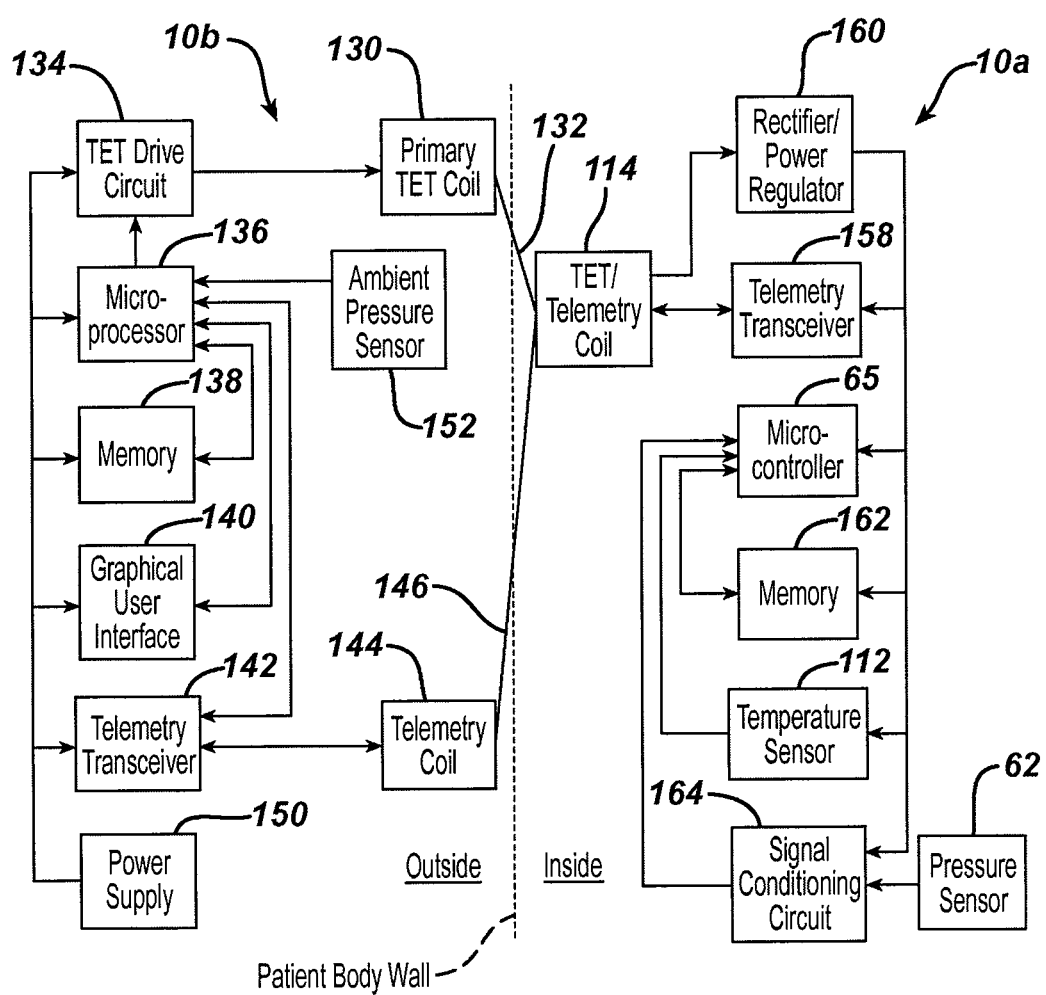
FIG. 7 is a block diagram showing an embodiment of internal and external components of the food intake restriction device of FIG. 1A.

FIG. 7 illustrates one embodiment of components included in the internal and external portions 10a, 10b of the food intake restriction system 10. As shown in FIG. 7, the external portion 10b includes a primary TET coil 130 for transmitting a power signal 132 to the internal portion 10a. A telemetry coil 144 is also included for transmitting data signals to the internal portion 10a. The primary TET coil 130 and the telemetry coil 144 combine to form an antenna, e.g., the reading device 70. The external portion 10b, e.g., the control box 90, includes a TET drive circuit 134 for controlling the application of power to the primary TET coil 130. The TET drive circuit 134 is controlled by a microprocessor 136 having an associated memory 138. A graphical user interface 140 is connected to the microprocessor 136 for inputting patient information and displaying and/or printing data and physician instructions. Through the user interface 140, a user such as the patient or a clinician can transmit an adjustment request to the physician and also enter reasons for the request. Additionally, the user interface 140 can enable the patient to read and respond to instructions from the physician and/or pressure measurement alerts, as discussed further below.

The external portion 10b also includes a primary telemetry transceiver 142 for transmitting interrogation commands to and receiving response data, including sensed pressure data, from the implanted microcontroller 65. The primary transceiver 142 is electrically connected to the microprocessor 136 for inputting and receiving command and data signals. The primary transceiver 142 drives the telemetry coil 144 to resonate at a selected RF communication frequency. The resonating circuit can generate a downlink alternating magnetic field 146 that transmits command data to the microcontroller 65. Alternatively, the transceiver 142 can receive telemetry signals transmitted from a secondary TET/telemetry coil 114 in the internal portion 10a. The received data can be stored in the memory 138 associated with the microprocessor 136. A power supply 150 can supply energy to the control box 90 in order to power element(s) in the internal portion 10a. An ambient pressure sensor 152 is connected to microprocessor 136. The microprocessor 136 can use a signal from the ambient pressure sensor 152 to adjust the received pressure measurements for variations in atmospheric pressure due to, for example, variations in barometric conditions or altitude, in order to increase the accuracy of pressure measurements.

FIG. 7 also illustrates components of the internal portion 10a, which in this embodiment are included in the sensor housing 60 (e.g., on the circuit board 64). As shown in FIG. 7, the secondary TET/telemetry coil 114 receives the power/communication signal 132 from the external antenna. The secondary coil 114 forms a tuned tank circuit that is inductively coupled with either the primary TET coil 130 to power the implant or the primary telemetry coil 144 to receive and transmit data. A telemetry transceiver 158 controls data exchange with the secondary coil 114. Additionally, the internal portion 10a includes a rectifier/power regulator 160, the microcontroller 65, a memory 162 associated with the microcontroller 65, a temperature sensor 112, the pressure sensor 62, and a signal conditioning circuit 164. The implanted components can transmit pressure measurements (with or without adjustments due to temperature, etc.) from the sensor 62 to the control box 90 via the antenna (the primary TET coil 130 and the telemetry coil 144). Pressure measurements can be stored in the memory 138, adjusted for ambient pressure, shown on a display on the control box 90, and/or transmitted, possibly in real time, to a remote monitoring station at a location remote from the patient.

Figure 8:
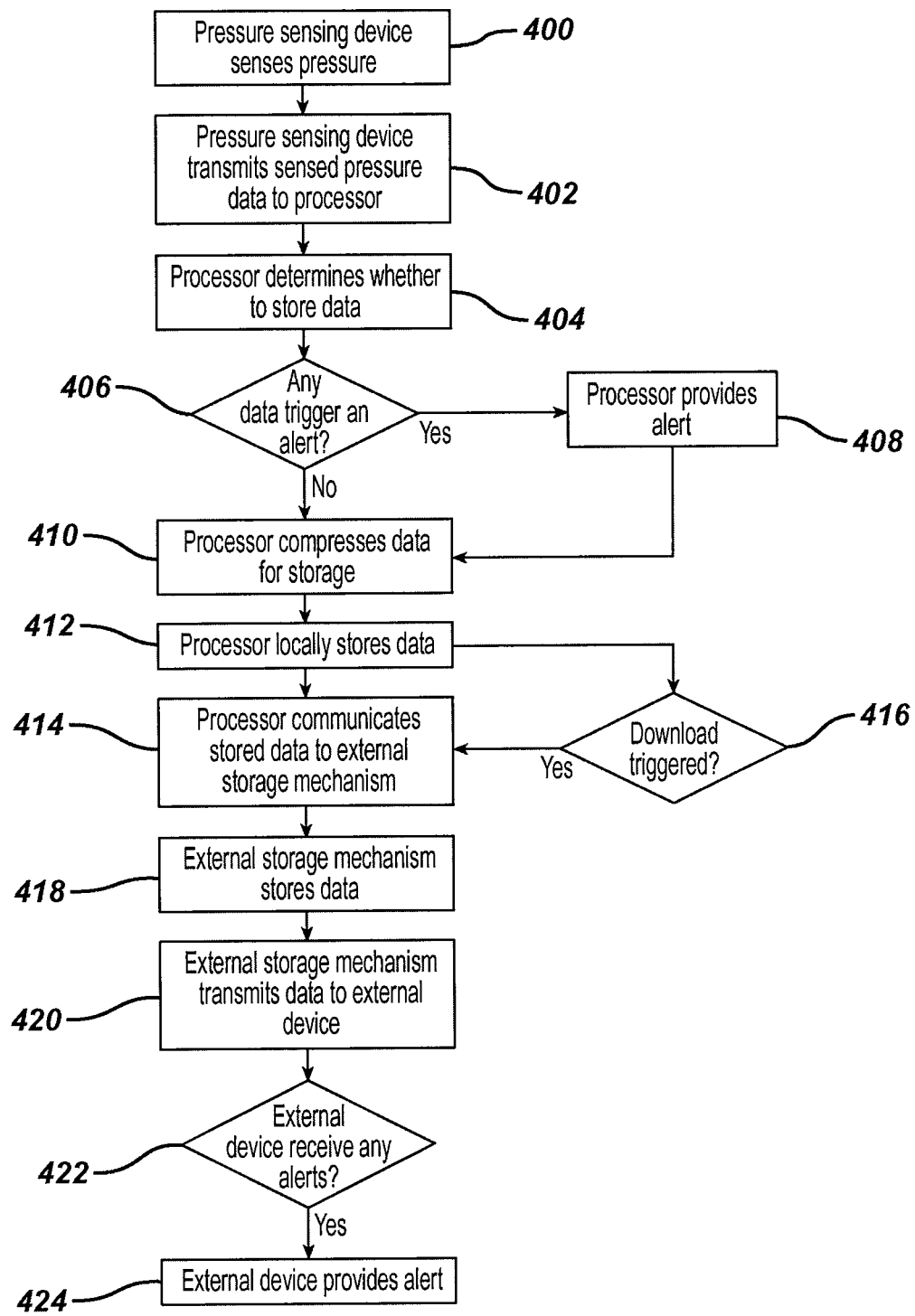
FIG. 8 is a flow diagram showing an embodiment of a data handling protocol for the food intake restriction device of FIG. 1A.

As illustrated in a process shown in FIG. 8, the sensor housing 60 can generally sense pressure within the gastric band 20, locally store the sensed pressure data (e.g., at the memory 162), and communicate at least a portion of the sensed pressure data to an external device such as the control box 90 via the reading device 70. While the pressure sensor 62 can communicate all pressure data it senses to the reading device 70, communicating only a selected portion of the pressure data (e.g., a portion less than the entirety of the sensed pressure data) can use less power, require less physical and/or electronic storage space in the sensor housing 60, and/or reduce costs.

While the process shown in FIG. 8 is discussed with relation to the elements included in FIGS. 1A-7, a person skilled in the art will appreciate that the process can be modified to include more or fewer elements, reorganized or not, and can be performed in the system 10 or in another, similar system having other, similar elements. For example, the microcontroller 65 processes instructions in this embodiment, but any processor configured to process instructions for a system (e.g., a central processing unit, a microprocessor, a digital signal processing unit, application specific integrated circuits (ASICs), a state machine, an analog computer, an optical or photonic computer, logic circuitry, etc.) can be used. Furthermore, the sensor 62 in this illustrated embodiment measures fluid pressure, but any sensed pressure data related to the band 20 can be handled as discussed herein.

In use, the sensor housing 60 can sense 400 a pressure of fluid disposed within the band 20 using the sensor 62. The sensor 62 can transmit measured signals to the signal conditioning circuit 164, which can amplify the signals before the signal conditioning circuit 164 transmits 402 the measured pressure data to the microcontroller 65. Alternatively, in some embodiments, the sensor 62 can directly transmit signals to the microcontroller 65. In this embodiment, the pressure sensor 62 provides pressure data at an update rate of approximately 20 Hz. Such a rate can provide a telemetry/TET mode cycle completion at approximately every 50 ms. For example, the TET/telemetry coil 114 can provide TET for the sensor housing 60 for approximately 45 ms to power the sensor housing 60 and then provide telemetry of pressure data for approximately 5 ms. Of course, any other switching topology can be used. It will also be appreciated that switching between TET and telemetry may be unnecessary. For example, the sensor housing 60 can be active, such that TET is not required. As another example, a second coil (not shown) can be added to the sensor housing 60, with one of the coils in the sensor housing 60 being dedicated to TET and the other to telemetry. Still other alternatives and variations will be apparent to those of ordinary skill in the art.

Having received sensed pressure data, the microcontroller 65 can determine 404 whether to store 412 the data, e.g., in the memory 162. Any type of memory can be used for the memory 162, including but not limited to one or more of volatile (e.g., SRAM, etc.), non-volatile (e.g., flash, hard drive, etc.), or other memory. Determining whether to store the data allows the microcontroller 65 to analyze the data and potentially discard at least a portion of the data before storing it, thereby using less of the storage space available in the memory 162. The microcontroller 65 can, however, be configured to store 412 all sensed pressure data and thus may not make such a determination and instead proceed to evaluating 406 whether any of the data triggers an alert, as further discussed below. (In such a configuration, it may be more power efficient to store raw (unprocessed) data from the pressure sensor 62 and process the raw data via an external reading device.) Furthermore, the memory 162 can be used to store pre-selected information or pre-selected types of information. For example, the memory 162 can store maximum, minimum, and/or baseline, pressure measurements, pressure profiles, pressure trends, fluoroscopic images or video of a patient swallowing, and/or any other information. Other information suitable for storing in the memory 162 will be appreciated by those skilled in the art.

The microcontroller 65 can analyze the data in a variety of ways in determining whether to store it. Typically, the microcontroller 65 analyzes a sequence of pressure data values measured over a period of time rather than analyzing every discrete pressure measurement, thereby allowing analysis of pressure trends over time and saving processing resources by not necessarily having to continually analyze incoming data. The microcontroller 65 can, however, evaluate individual pressure data measurements (and/or a range of data) for invalid data and determine to discard any invalid data. Generally, in determining whether to store data, the microcontroller 65 considers a variation of pressure data from a nominal pressure, or resting pressure, within the band 20. The nominal pressure is typically programmed into the microcontroller 65 by a physician based on historical band performance in the patient or, particularly for recently implanted bands, in a typical patient. If the measured pressure data exceeds the nominal pressure, then the data indicates pressure variation in the system 10 and hence likely includes potentially beneficial information for analytical, diagnostic, and/or other purposes. If the pressure data substantially equals the nominal pressure, then the data is not likely indicative of a potentially significant event for analysis purposes, e.g., a change in band pressure due to patient activity such as eating or drinking. The microcontroller 65 can discard any such substantially nominal data. Discarding data can include not storing the data or storing a representation of the data, e.g., storing a specific set of digits (e.g., "888," "999," "000," etc.) or one or more alphabetic characters. Different representations of data can be used to indicate measurement of a different types of data, e.g., substantially nominal data, data outside a defined pressure range, etc. Although, in some embodiments, the microcontroller 65 can store 412 even nominal pressure data in the memory 162 to maintain a complete historical record of pressure measurements. Furthermore, the microcontroller 65 can store 412 all sensed pressure data it receives in the memory 162 and subsequently determine whether to keep or discard it, e.g., store all data and analyze it every "X" minutes and/or upon signal from an external device.

Figure 9:
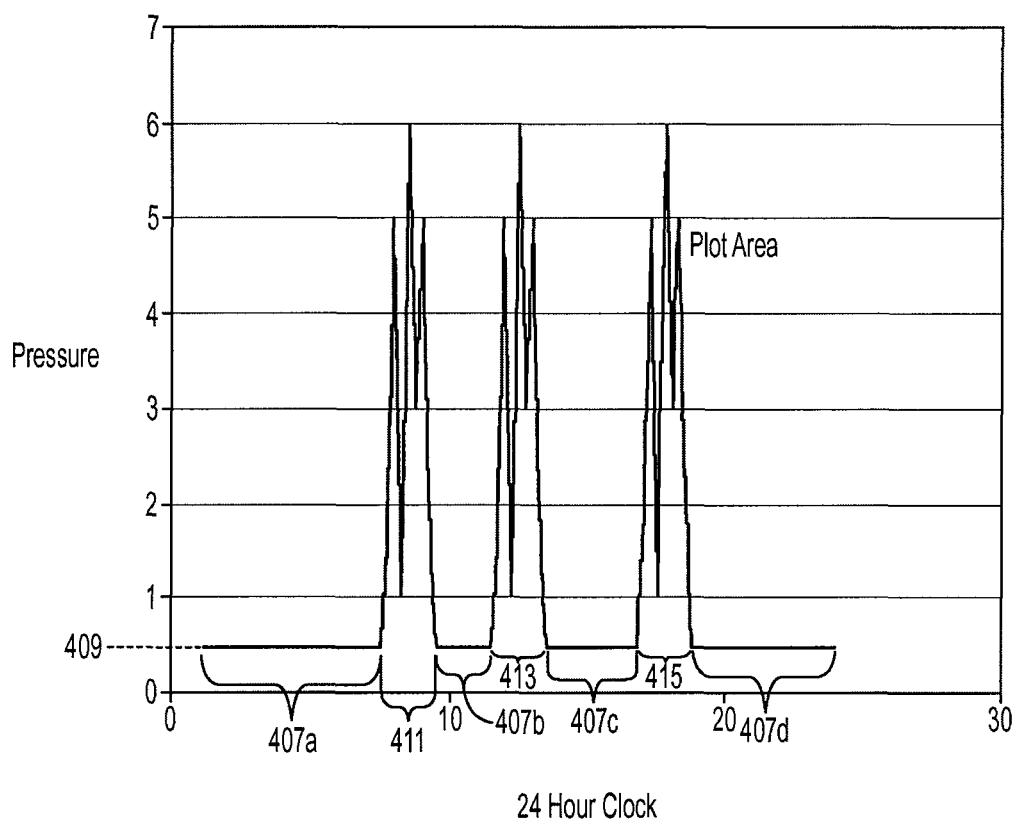
FIG. 9 is a graphical representation of a pressure measurement from the pressure sensor of FIG. 5.
Figure 10:
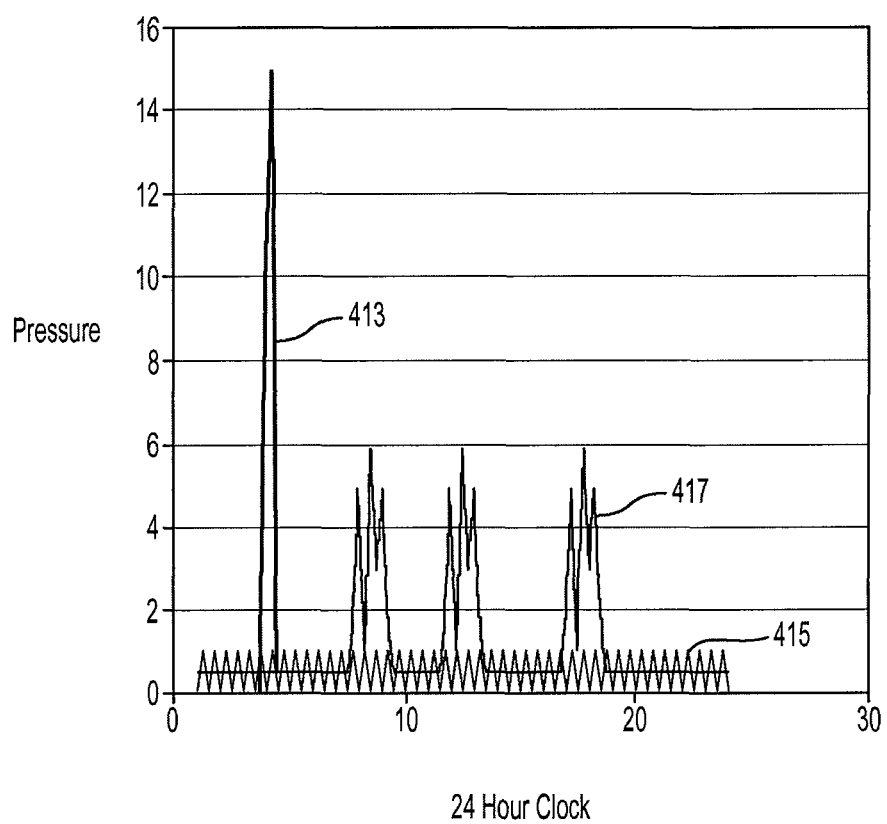
FIG. 10 is a graphical representation of another pressure measurement from the pressure sensor of FIG. 5.

FIGS. 9 and 10 show example sequences of pressure data that the microcontroller 65 can receive from the sensor 62. In each of FIGS. 9 and 10, a plot shows sensed pressure data versus time for a twenty-four hour period. The plot in FIG. 9 includes four periods 407a, 407b, 407c, 407d of substantially nominal pressure at a nominal pressure level 409. The nominal pressure level 409 shown in the plot is an example only; the nominal pressure value can be any value or range of values. Furthermore, the nominal pressure value for a patient can change over time, e.g., as the patient loses weight. The microcontroller 65 can compare the pressure data from this twenty-four hour period with the nominal pressure 409 and determine to discard data from the nominal pressure periods 407a, 407b, 407c, 407d (e.g., never store it in the memory 162 or delete it from the memory 162) and only store 412 the remaining, selected portion of pressure data. In some instances, the microcontroller 65 can determine to discard pressure data that exceeds the nominal pressure 409. For example, the microcontroller 65 can discard pressure data except for data obtained during two of three meals the patient ate during the day, e.g., discard pressure data measured during the four periods 407a, 407b, 407c, 407d and during a breakfast period 411 and store 412 the remaining, selected pressure data, corresponding to lunch and dinner periods 413, 415. Pressure data can be determined to be related to a particular meal based on one or more factors considered by the microcontroller 65, such as a combination of a time of day when the sensor 62 measured the data and a duration of pressure values above the nominal level 409.

The microcontroller 65 can also determine to discard pressure data related to one or more physiologic events, as illustrated in FIG. 10. Non-limiting examples of physiologic events include supra events (e.g., coughing, vomiting, wretching, etc.) and normal events (heartbeats, breathing, talking, etc.). Physiologic events can result in measured pressure data that significantly differs from an expected level in magnitude, duration, occurrence (e.g., an unexpected time of day, such as midnight), and/or frequency from established patterns of patient eating. The microcontroller 65 can determine to retain pressure data by analyzing the data for such a significant difference, such as by determining if any of the obtained pressure data includes a value above a pre-programmed threshold value typically not exceeded except in response to a physiologic event. The microcontroller 65 can also or instead determine if any of the obtained pressure data includes a value within a defined range of pressure values. Depending on the defined range, which can in some embodiments be defined at an upper and/or lower limit by an immediately preceding pressure data value or by pressure values corresponding to a particular time of day, the microcontroller 65 can determine to discard data within the range (e.g., if the range reflects pressure readings of an expected frequency and magnitude caused by a normal event) or to retain data within the range (e.g., if the range includes any positive pressure values up to a threshold value typically not exceeded except by a physiologic event). As an example, the plot in FIG. 10 includes pressure data 413 indicative of a supraphysiologic event, pressure data 415 indicative of a normal event, and actual band pressure data 417. The microcontroller 65 can discard the event data 413 and the normal event data 415 using one or more programmed algorithms as described above.

The microcontroller 65 can also determine 406 whether any data triggers an alert. If the microcontroller 65 determines that any pressure data falls outside a defined range of pressure values and/or is more or less than a threshold value, then the microcontroller 65 can provide 408 an alert to a physician, the patient, and/or to any number of other people because such outlying pressure data can indicate a possible problem such as band leakage, band over-tightening, recurrent wretching, band slippage, erosion, etc. The microcontroller 65 can provide the alert by, for example, communicating a signal to an external device (e.g., the control box 90) indicating the potentially problematic sensed pressure data and triggering notice of the alert. An alert can include any one or more of the following: an e-mail, a phone call, a text message, an audible signal, a mechanical vibration, a light or other visual display, a tactile display, a message displayed on an external device, or any other type of alert. Different alert patterns (e.g., varying audio signals, varying vibration patterns, etc.) can be used to signify different conditions. Two or more alerts can be provided to multiple people under similar conditions, although alerts may not be provided simultaneously to multiple people or be provided to anyone at all. The conditions for and/or the type of an alert can also vary relative to the recipient of the alert. For example, with respect to alerts for physicians or other medical personnel, such alerts may be limited to those provided upon a supra event indicating that some component of the internal portion 10a has structurally failed (e.g., a kink in catheter 50, a leak in the band 20, etc.). With respect to alerts for patients, such alerts may be limited to patient activity such as those provided upon an indication that the patient is eating too much, eating too quickly, or if the patient's bite sizes are too big. A variety of other conditions under which alerts can be directed to a physician, a patient, and/or another person will be understood by those skilled in the art. Other suitable processes for detecting alert triggers, as well as ways in which the alerts can be provided and the timing of providing the alerts (e.g., immediately, on a regular schedule such as every day or every hour, after detection of a certain milestone or pattern of data, etc.), will be appreciated by those skilled in the art.

The microcontroller 65 can optionally compress 410 data prior to storing 412 data in the memory 162. Such compression can reduce the amount of memory space required to store data in the internal portion 10a (and subsequently in the external portion 10b), reduce the number of microcontroller accesses to the memory 162 (thereby saving power), reduce the amount of time and/or power required to communicate data from the sensor housing 60 to an external device, and allow more data to be locally stored prior to communicating the data to an external device. While pressure data is shown in FIG. 8 as being compressed following a determination of a selected portion of data to store in the memory 162, if any, the microcontroller 65 can compress data before making such a determination. For example, as mentioned above, the microcontroller 65 can store 412 pressure data prior to making such a determination (possibly subsequently retrieving the data for analysis). As another example, the microcontroller 65 may not be configured to perform such determining analysis and may store 412 all data for communication to an external device.

The microcontroller 65 can compress data using any one or more lossless and/or lossy compression techniques. Non-limiting examples of lossless compression techniques include recording difference values (instead of absolute values), reducing the sensor's data sampling rate (which can include reducing the sensor's data sampling rate to zero) during a determined period (e.g., a period of quiescent pressure, after a certain period of data-gathering time, etc.), run-length coding, Huffman coding, and other types of lossless compression. Non-limiting examples of lossy compression includes using a quantization table (e.g., sparse quantization) and other types of lossy compression. Storing difference values instead of absolute values can be effective compression if, typically at the beginning of pressure measuring and at regular intervals, the microcontroller 65 stores an absolute value in the memory 162 that can serve as a baseline in reconstructing the originally sensed data. Sensed pressure values are often near the values of their neighbors, so differences from a baseline are often likely to be small, if not zero. The microcontroller 65 can compress difference values for storage using a compression technique, such as encoding difference values into the shortest code symbols in Huffman coding.

Data stored in the memory 162 can be communicated 414 to an external device. In some embodiments, the microcontroller 65 continually communicates 414 data (via the telemetry transceiver 158 and the secondary coil 114), and the data is only received when an appropriate receiving device, such as the antenna (the primary TET coil 130 and the telemetry coil 144), moves into sufficient proximity of it. In some embodiments, a download of data from the memory 162 can be triggered 416 when an external device (e.g., the reading device 70) telemetrically provides power to the sensor housing, e.g., when the external device is moved in proximity of the sensor housing 60. The external device can be mobile (e.g., a wand or hand-held unit that can be waved or otherwise placed in proximity of the sensor housing 60) or stationary (e.g., a bedside, desk-mounted, or car-mounted box that the patient can move near). Telemetrically providing power to the sensor housing 60 can save power in the internal portion 10a because download communication power is supplied by the external portion 10b.

The external device can be configured to store 418 data received from the sensor housing 60. The external device can be further configured communicate 420 the data to another external device, such as a base unit at a location remote from the patient. The external device (typically, the control box 90 or other device having a capability to display or otherwise provide an alert) can detect 422 if the internal portion 10a communicated a signal indicating an alert and provide 424 an alert as appropriate (e.g., displaying a warning notice, sending an e-mail message, etc.).

Figure 11:
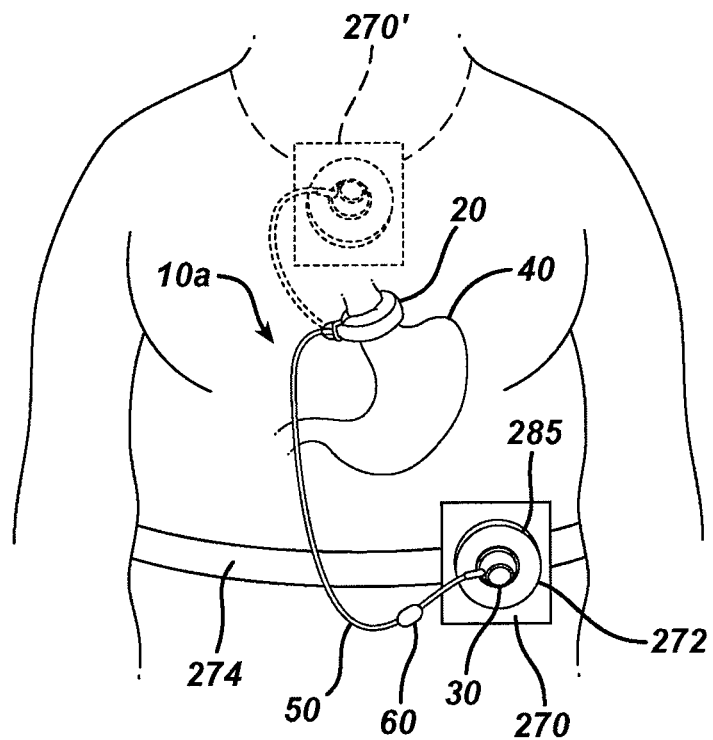
FIG. 11 is a schematic diagram of an embodiment of a data logger for recording pressure measurements related to the food intake restriction device of FIG. 1A.

As mentioned above, a pressure history (e.g., pressure data gathered by the sensor 62) can be uploaded to the control box 90 (and/or other units located local or remote to the patient) to allow a person to physically evaluate and/or the control box 90 to electronically evaluate the patient's treatment and/or performance of elements included in the internal portion 10a over a designated time period. FIG. 11 illustrates an embodiment of an external device, a data logger 270, that can be used as an external storage mechanism to store pressure measurements over a period of time. The data logger 270 can function as a removably attached data reading device 70, mentioned above. In this example, the data logger 270 includes a wearable pack external to the patient worn on a belt 274 and positioned over or within communication range of the region under which the sensor housing 60 is implanted within the patient. Alternatively, the data logger 270 can be worn about the patient's neck, as shown by a device 270', such as when the injection port 30 is implanted on the patient's sternum and the port 30 includes the pressure sensing device. In another embodiment, the data logger 270 is also implanted within the patient.

As shown in FIG. 11, the data logger 270 includes a TET coil 285 and a telemetry coil 272 which can be worn by the patient so as to lie adjacent to the internal portion 10a. The TET coil 285 can provide power to the implant, while the telemetry coil 272 can interrogate the implant and can receive data signals, including pressure measurements, through the secondary telemetry coil 114 in the implanted portion 10a. In another embodiment, the TET coil 285 and the telemetry coil 272 can be consolidated into a single coil and alternate between TET and telemetry functions at any suitable rate for any suitable durations.

The pressure within the band 20 can be repeatedly sensed and transmitted to the data logger 270 at an update rate sufficient to measure peristaltic pulses against the band 20. Typically, this update rate is in the range of 10-20 pressure measurements per second, but any update range can be used. The data logger 270 is typically worn during waking periods to record pressure variations during the patient's meals and daily routines. At the end of the day, or another set time period, the data logger 270 can be removed and recorded pressure data downloaded to the external memory 138. The pressure history can be uploaded from the memory 138 to a remote unit over one or more communication links during a subsequent communication session. Alternatively, pressure data can be directly uploaded from the data logger 270 to a remote unit using one or more communication links. A communication link can include any single or combination of two or more data transmission media including web-based systems utilizing high-speed cable or dial-up connections, public telephone lines, wireless RF networks, Bluetooth, ultrawideband (UWB), satellite, T1 lines or any other type of communication media suitable for transmitting data between remote locations. The data logger 270 can be configured to dock into another device, e.g., a docking station, that is configured to receive data communication from the data logger 270 and transmit the received data to a remote unit.

Figure 12:
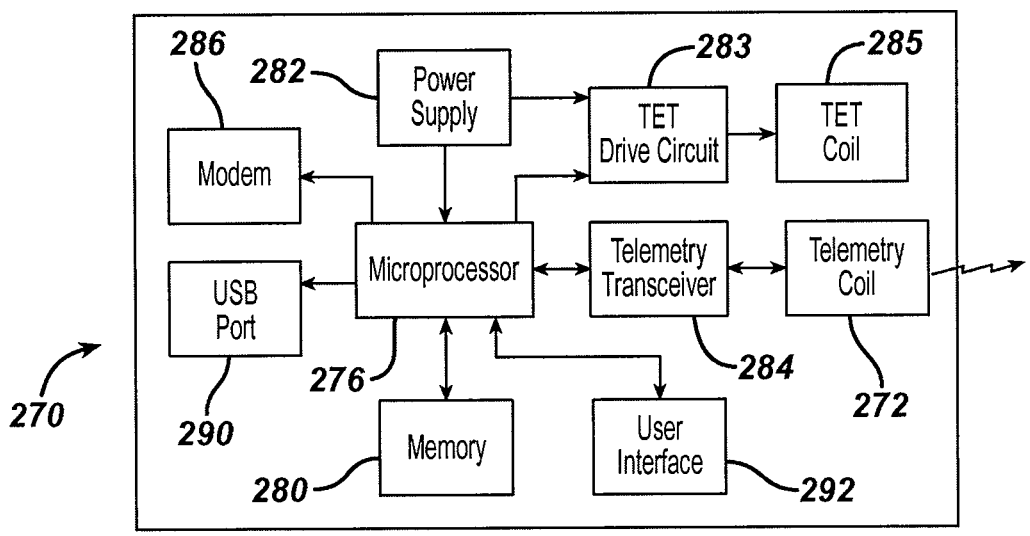
FIG. 12 is a block diagram showing an embodiment of components of the data logger of FIG. 11.

FIG. 12 shows the data logger 270 in greater detail. As shown in FIG. 12, the data logger 270 includes a microprocessor 276 for controlling telemetry communications with the internal portion 10a. The microprocessor 276 is connected to a memory 280 for, at least, storing pressure measurements from the internal portion 10a. In this embodiment, the memory 280 includes forty MB of Non-Volatile EEPROM or FLASH memory and is configured to store about one hundred hours of time stamped pressure data, but any other type of storage can be used, and the memory 280 can store any amount of and any type of data. By way of non-limiting example, any other type of volatile memory or any type of non-volatile memory can be used, including but not limited to flash memory, hard drive memory, etc. While the data logger 270 in this example is operational, pressure can be read and stored in the memory 280 at a designated data rate controlled by the microprocessor 276.

The microprocessor 276 can be energized by a power supply 282. In one embodiment, the power supply 282 includes a rechargeable cell (not shown), such as a rechargeable battery. In some embodiments, the rechargeable cell is removable and can be recharged using a recharging unit and replaced with another rechargeable cell while the spent cell is recharging. In other embodiments, the rechargeable cell can be recharged by plugging a recharging adapter into the data logger 270 and a wall unit. In yet another embodiment, the rechargeable cell can be recharged wirelessly by a wireless recharging unit. In still another embodiment, the power supply 282 includes an ultra capacitor, which can also be recharged. Of course, any other type of power supply can be used.

To record pressure, the microprocessor 276 can initially transmit a power signal to the internal portion 10a via a TET drive circuit 283 and the TET coil 285. After transmitting the power signal, the microprocessor 276 can transmit an interrogation signal to the internal portion 10a via a telemetry transceiver 284 and the telemetry coil 272. The interrogation signal can be intercepted by the telemetry coil 114 and transmitted to the microcontroller 65. The microcontroller 65 can send a responsive, optionally-temperature-adjusted pressure reading from the sensor 62 via the transceiver 158 and the secondary telemetry coil 114. The pressure reading can be received through the telemetry coil 272 and directed by the transceiver 284 to the microprocessor 276. The microprocessor 276 can store the pressure measurement and initiate the next interrogation request. If applicable, the microprocessor 276 can also respond to an alert identified by the microcontroller 65, such as with a visual alert (e.g., flashing a light on the data logger 270, displaying a message on a user interface 292, etc.) and/or with an audible alert. The user interface 292 can include any number and types of features, including but not limited to a speaker, an LED, an LCD display, an on/off switch, etc. In some embodiments, the user interface 292 is configured to provide only output to the patient and does not permit the patient to provide input to the data logger 270. The user interface 292 thus includes an LED, which when lit shows that the power supply 282 is sufficiently charged and another, differently colored LED to show when the power supply 282 needs to be recharged, although such power indicators can be shown using any type and any combination of indicators such as one light that illuminates upon low power charge, an audible alert, an email alert, etc. In other embodiments, the user interface 292 can allow the patient to provide input to the data logger 270 and can accordingly include any suitable components and features.

When finished measuring and recording pressure, the data logger 270 can be removed from the patient and/or from the belt 274 and the recorded pressure data downloaded to the control box 90 (and/or to any other external device). The data logger 270 can include a modem 286 for transmitting sensed pressure data directly to a remote base unit using a communication link. For example, the patient can connect the modem 286 to a telephone line (or other communication link), dial the physician's modem (if necessary), and select a "send" button on the user interface 292. Once connected, the microprocessor 276 can transmit stored pressure history through the phone line to a microprocessor included in the remote unit. Alternatively, the data logger 270 can include a USB port 290 for connecting the logger 270 to the control box 90. The logger USB port 290 can be connected to a USB port included on the control box 90 and the "send" switch activated to download pressure data to the memory 138 in the control box 90. After pressure data is downloaded, the logger 270 can be turned off through the user interface 292 or reset and placed back on the patient and/or the belt 274 for continued pressure measurement.

Figure 13:
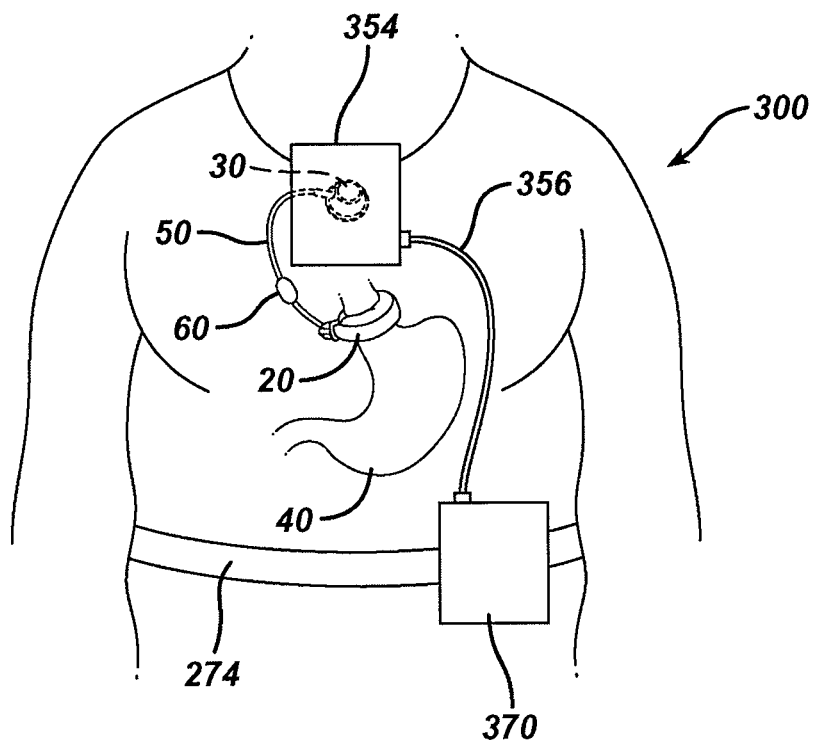
FIG. 13 is a schematic diagram of an embodiment of a data logging system for recording pressure measurements related to the food intake restriction device of FIG. 1A.

An alternate embodiment of a data logging system 300 is shown in FIG. 13. In this example, the data logging system 300 includes a coil head 354 and a data logger 370. The coil head 354 and the data logger 370 are in communication via a detachable cable 356. Any one or more suitable alternative communication links can be used in the place of the cable 356, including but not limited to a wireless transmitter/receiver system. In the illustrated embodiment, the coil head 354 is worn around the neck of the patient and is positioned generally over the injection port 30 and within communication range of the sensor housing 60. The data logger 370 is worn on the belt 274 about the patient's waist. Of course, these respective locations are merely exemplary, and either or both the coil head 354 and the data logger 370 can be positioned elsewhere. By way of non-limiting example, when the injection port 30 is implanted in the patient's abdomen, the coil head 354 can be worn on the belt 274. The coil head 354 and the data logger 370 are represented as simple blocks in FIG. 13 for illustrative purposes only, and either of the coil head 354 or the data logger 370 can be provided in a variety of shapes, sizes, and configurations.

Figure 14:
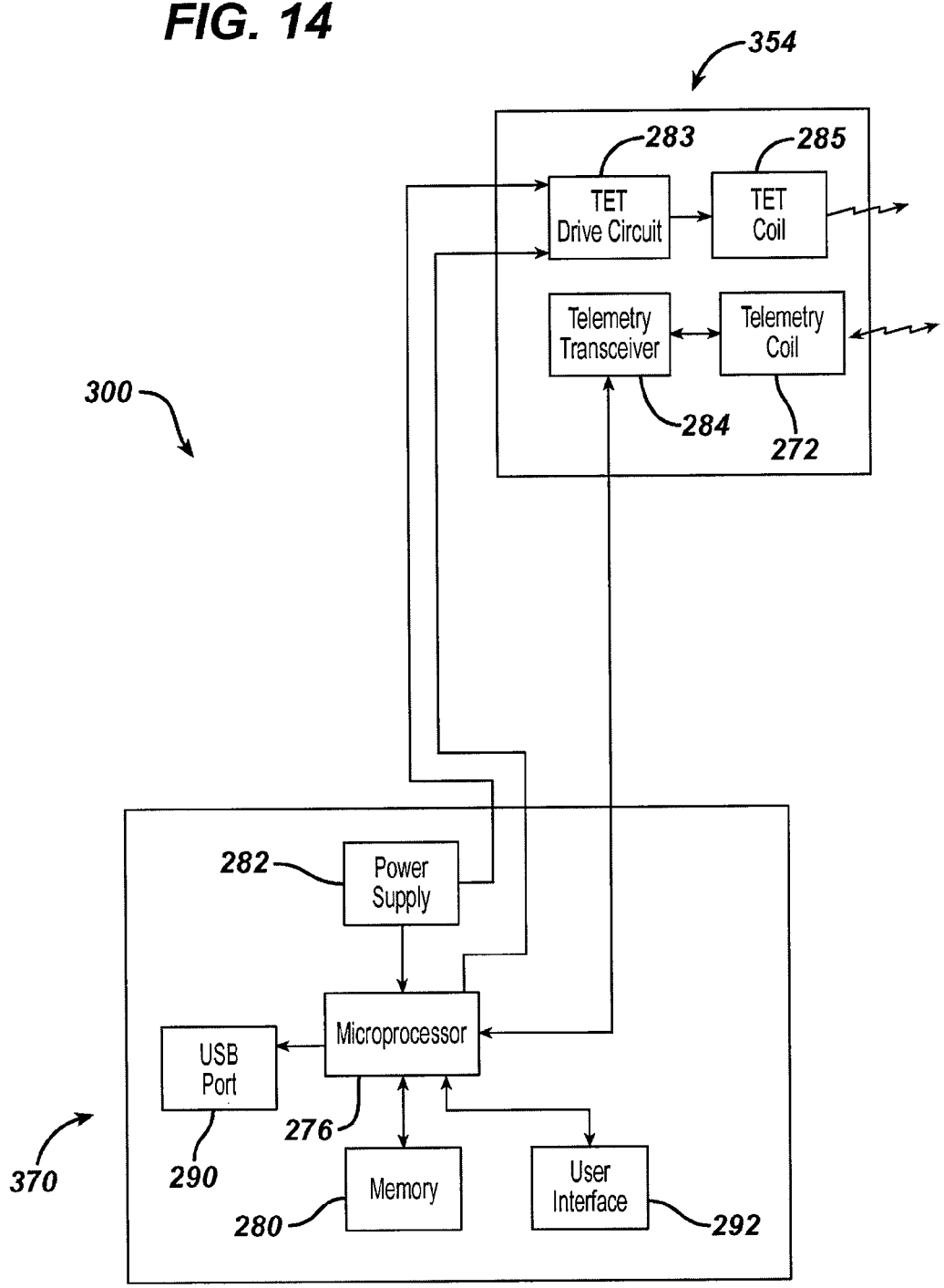
FIG. 14 is a is a block diagram showing an embodiment of components of the data logging system of FIG. 13.

Exemplary components of the data logging system 300 are shown in FIG. 14. As shown, the data logger 370 includes the microprocessor 276, the memory 280, the power supply 282, the USB port 290, and the user interface 292. The coil head 354 includes the TET drive circuit 283, the telemetry transceiver 284, the TET coil 285, and the telemetry coil 272. The TET drive circuit 283 is configured to receive power from the power supply 282 via the cable 356. The TET drive circuit 283 is further configured to receive signals from the microprocessor 276 via the cable 356. The telemetry transceiver 284 is configured to receive signals from the microprocessor 276 and transmit signals to the microprocessor 276, via the cable 356. In another embodiment, the telemetry transceiver 284 is configured to only transmit signals to the microprocessor 276. The above discussion of such components with reference to FIG. 12 can also be applied to the components shown in FIG. 14. In the embodiment illustrated in FIG. 14, the coil head 354 and the data logger 370 can be viewed as a separation of components including the data logger 270 (described above) into two physically separate units. It will be appreciated by a person skilled in the art that any of the components shown in FIG. 14, as well as their relationships, functions, etc., can be varied in any suitable way.

In the present example, the coil head 354 is configured similar to and functions in a manner similar to the antenna (the primary TET coil 130 and the telemetry coil 144) described above. The TET coil 285 of coil head 354 is configured to provide power to the injection port 30. Of course, to the extent that any other devices (e.g., a pump, etc.) are implanted in the patient that are configured to receive power from the TET coil 285, the TET coil 285 can also provide power to such devices. Power provided by the TET coil 285 can be provided to the TET coil 285 by and regulated by the TET drive circuit 285, which can itself receive power from the power supply 282 via the cable 356. Such power provided to the TET drive circuit 283 can be regulated by the microprocessor 276 via the cable 356. In addition, or in the alternative, the microprocessor 276 can regulate the manner in which the TET drive circuit 285 provides power to the TET coil 285. While the present example contemplates the use of RF signaling through the TET coil 285, any other type of powering technique, as well as alternative power communicators, can be used. Other suitable configurations and relationships between these components, as well as alternative ways in which they may operate, will be appreciated by those skilled in the art.

The telemetry coil 272 of the coil head 354 is configured to receive signals from the coil 114, including signals indicative of the pressure within the implanted band system (e.g., pressure of fluid within the injection port 30, within the catheter 50, and/or within the adjustable band 20, pressure obtained using the pressure sensor 62, etc.) and signals indicative of temperature. The telemetry coil 272 can also receive any other type of signal representing any other type of information from any other source. Signals received by the telemetry coil 272 can be communicated to the telemetry transceiver 284, which can communicate such signals to the microprocessor 276 via the cable 356. The telemetry transceiver 284 can perform any appropriate translation or processing of signals received from the telemetry coil 272 before communicating signals to the microprocessor 276. Other suitable configurations and relationships between these components, as well as alternative ways in which they may operate, will be appreciated by those skilled in the art. It will also be appreciated that components may be combined. By way of non-limiting example, the TET coil 285 and the telemetry coil 272 can be consolidated into a single coil and alternate between TET and telemetry functions at any suitable rate for any suitable durations. In addition, while the present example contemplates the use of RF signaling through the telemetry coil 272, it will be appreciated that any other type of communication technique (e.g., ultrasonic, magnetic, RF, light, inductive, etc.) can be used alone or in any combination, as well as alternative communicators other than a coil, can be used. Furthermore, different data handling can be more beneficial to a given communication technique, and given a particular communication technique, appropriate data handling can be selected.

In one exemplary use, the patient wears the coil head 354 and the data logger 370 throughout the day to record pressure measurements in the memory 280. At night, the patient can decouple the data logger 370 from the coil head 354 and couple the data logger 370 with a docking station, e.g., the control box 90. While the data logger 370 and the control box 90 are coupled, the control box 90 can transmit data received from the data logger 370 to a remote unit. To the extent that the power supply 282 includes a rechargeable cell, the control box 90 can recharge the cell while the data logger 370 is coupled with the control box 90. However, a patient need not necessarily decouple the data logger 370 from the coil head 354 in order to couple the data logger 370 with the control box 90. Moreover, pressure measurements can be recorded in the memory 280 during the night in addition to or as an alternative to recording such measurements during the day, and pressure measurements can be recorded twenty-four hours a day. In that way, timing of pressure measurement taking and recordation need not be limited to the daytime only.

As described above, the data logger 370 can receive, store, and communicate data relating to pressure within the restriction system. However, the data logger 370 can receive, store, and/or communicate a variety of other types of data. By way of non-limiting example, the data logger 370 can also receive, process, store, and/or communicate data relating to temperature, EKG measurements, eating frequency of the patient, the size of meals eaten by the patient, the amount of walking done by the patient, etc. It will therefore be appreciated by those skilled in the art that the data logger 370 can be configured to process received data to create additional data for communicating to the control box 90. For example, the data logger 370 can process pressure data obtained via the coil head 354 to create data indicative of the eating frequency of the patient. It will also be appreciated by those skilled in the art that the data logger 370 can include additional components to obtain non-pressure data. For example, the data logger 370 can include a pedometer or accelerometer (not shown) to obtain data relating to the amount of walking done by the patient. Data obtained by such additional components can be stored in the memory 280 and communicated to the control box 90 in a manner similar to pressure data. The data logger 370 can also include components for obtaining data to be factored in with internal pressure measurements to account for effects of various conditions on the pressure. For example, the data logger 370 can include a barometer for measuring atmospheric pressure. In some embodiments, the data logger 370 includes an inclinometer or similar device to determine the angle at which the patient is oriented (e.g., standing, lying down, etc.), which can be factored into pressure data to account for hydrostatic pressure effects caused by a patient's orientation. Alternatively, an inclinometer or other device for obtaining non-pressure data can be physically separate from the data logger 370 (e.g., implanted). Still other types of data, ways in which such data may be obtained, and ways in which such data may be used will be appreciated by those skilled in the art.

It will also be appreciated by those skilled in the art that one or more embodiments described herein can enable health care providers or others to use pressure data as a feedback mechanism to identify, train, and/or prescribe dietary advice to a patient. Such a feedback mechanism can provide data or otherwise be used in multiple ways. For example, pressure feedback can be obtained when a patient swallows a particular food portion, and based on such pressure feedback, the patient can be advised or taught to eat smaller portions, larger portions, or portions equal to the portion tested. Of course, a food portion so prescribed can be tested by evaluating pressure feedback obtained when the patient swallows the prescribed food portion, such that a food portion prescription may be refined through reiteration. As another example, a patient can test desired foods for appropriateness based on pressure feedback together with portion size and/or based on any other parameters. It will also be appreciated by those skilled in the art that continuous pressure data monitoring can be used locally and/or remotely to enable portion size monitoring, food consistency monitoring (e.g., liquids vs. solids), eating frequency, and/or other patient activities.

Figure 15:
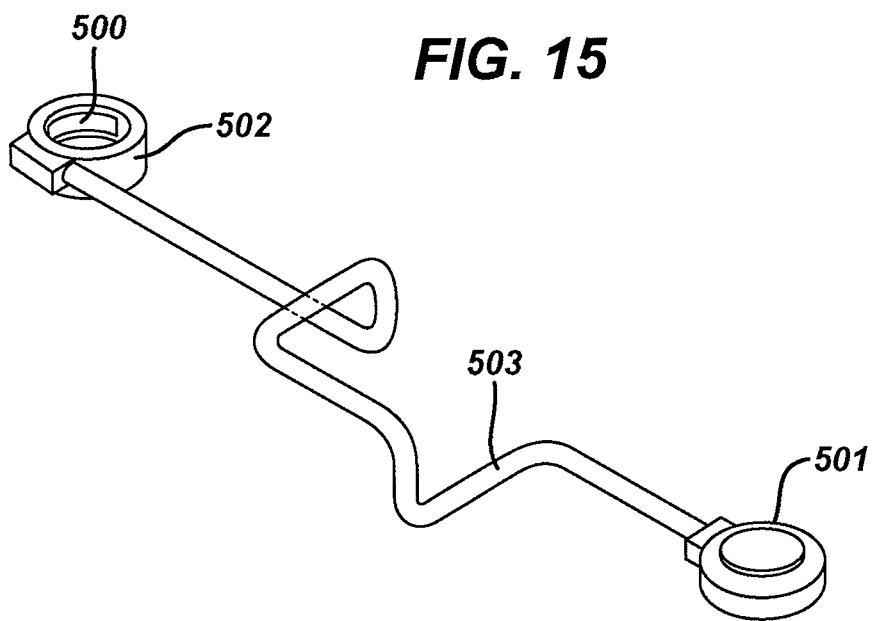
FIG. 15 is a perspective view of an embodiment of a gastric band system with a pressure sensor positioned along a catheter.

While embodiments described above include the use of the pressure sensor 62 within the sensor housing 60 removably joined to the catheter 50, a pressure sensor can be located elsewhere within a patient. For example, the pressure sensor 62 could be included in the port housing 30. In another embodiment, shown in FIG. 15, a pressure sensor 500 can be located within a gastric band 502, such as in an inflatable portion of gastric band 502. To the extent that the gastric band 502 includes a resilient portion and a non-resilient portion, the pressure sensor 500 can be secured to either or neither of the resilient portion or non-resilient portion. In any case, the pressure sensor 500 can sense and communicate fluid pressure within the gastric band 502 before, during, and after fluid is added to or withdrawn from gastric band 502 via an injection port 501 and a catheter 503. The pressure sensor 500 can be used when a pump (not shown) or any other device is used to adjust pressure within the gastric band 502.

Figure 16:
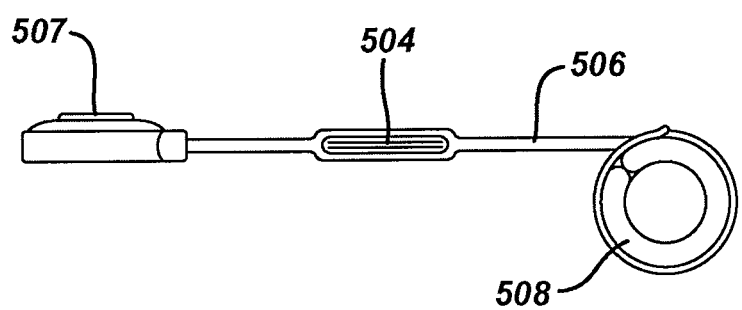
FIG. 16 is a schematic view of an embodiment of a gastric band system with a pressure sensor positioned within a catheter.
Figure 17:
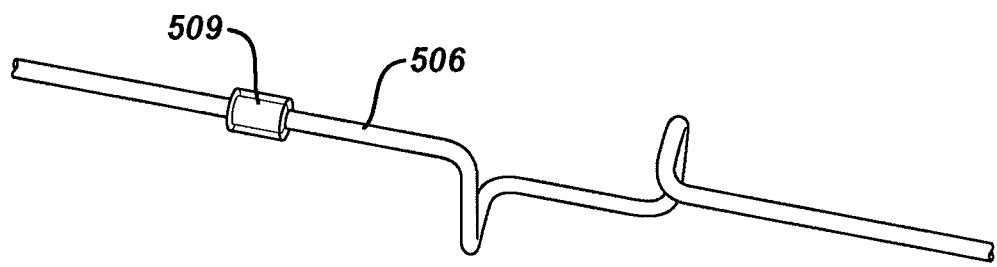
FIG. 17 is a perspective view of another embodiment of a gastric band system with a pressure sensor positioned along a catheter.

Alternatively, as shown in FIG. 16, a pressure sensor 504 can be located within a catheter 506 positioned between a gastric band 508 and a port 507, pump, reservoir, or other device in fluid communication with the catheter 506. As another variation, an example of which is shown in FIG. 17, a pressure sensor 509 can be fixedly secured in-line with a catheter 506, while not residing within catheter 506.

Figure 18:
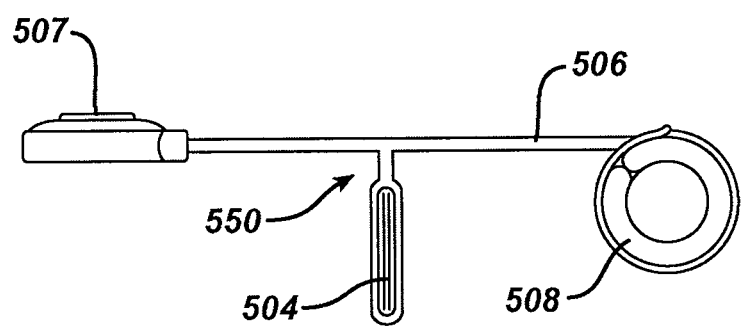
FIG. 18 is a schematic view of an embodiment of a gastric band system with a "T"-shaped pressure sensor and catheter configuration.

Yet another variation is shown in FIG. 18, which illustrates a catheter 506 having a "T"-shaped intersection 550. A pressure sensor 504 is disposed in the arm of the "T"-shaped intersection 550 that is perpendicular to the catheter 506 and is in fluid communication with the catheter 506. In one embodiment, the "T"-shaped intersection 550 is integrally formed with the catheter 506 (as shown). In another embodiment, the "T"-shaped intersection 550 is a separate component joined to the catheter 506 (e.g., using barbed connectors, etc.). Other suitable ways in which the "T"-shaped intersection 550 can be provided will be appreciated by those skilled in the art. Similarly, other ways in which a pressure sensor 504 can be provided within, in-line with, or adjacent to the catheter 506 will be appreciated by those skilled in the art.

In yet another embodiment (not depicted), a pressure sensor can be located at the interface of an injection port and a catheter, and/or at the interface of a gastric band and a catheter. Still other suitable locations for a pressure sensor will be appreciated by those skilled in the art, including but not limited to any location in or adjacent to the fluid path of a gastric band system. In addition, a pressure sensor can be positioned within (e.g., against an inner wall of) a gastric band, a catheter, and a buckle, or alternatively, a portion of such band, catheter, and buckle can include a protrusion extending outwardly therefrom to house at least a portion of the corresponding pressure sensor. Other suitable configurations for housing a pressure sensor within or adjacent to a band, catheter, or buckle will be appreciated by those skilled in the art.

In another embodiment, a plurality of pressure sensors can be used. For example, a gastric band system can include a pressure sensor within a gastric band in addition to a pressure sensor within a catheter that is in fluid communication with the gastric band. Such a plurality of pressure sensors can provide an indication of how well fluid pressure is distributed among components of a gastric band system. Such a plurality of pressure sensors can also provide greater accuracy in pressure readings, reduce the likelihood of catheter obstruction (e.g., pinching) affecting pressure reading, reduce effects of hydrostatic pressure changes from patient movement, and/or provide one or more other results. Any system that includes a plurality of pressure sensors can include a pressure sensor in a port housing and/or a pressure sensor external to the patient (e.g., a pressure sensor in a syringe or in a pressure sensor portion coupled with a syringe), in addition to any of the implanted pressure sensors described above. Furthermore, a device such as an internal or external inclinometer (or a substitute therefor) may be used to determine the angle at which the patient and/or the internal portion is oriented (e.g., standing, lying down, etc.), which may be factored into pressure data sensed by one or more sensors to account for hydrostatic pressure effects caused by a patient's orientation. Such a factor (or any other factor) may be accounted for prior to or in conjunction with the rendering of a pressure reading.

A person skilled in the art will appreciate that the present invention has application in conventional endoscopic and open surgical instrumentation as well application in robotic-assisted surgery.

The devices disclosed herein can be designed to be disposed of after a single use, or they can be designed to be used multiple times. In either case, however, the device can be reconditioned for reuse after at least one use. Reconditioning can include any combination of the steps of disassembly of the device, followed by cleaning or replacement of particular pieces, and subsequent reassembly. In particular, the device can be disassembled, and any number of the particular pieces or parts of the device can be selectively replaced or removed in any combination. Upon cleaning and/or replacement of particular parts, the device can be reassembled for subsequent use either at a reconditioning facility, or by a surgical team immediately prior to a surgical procedure. Those skilled in the art will appreciate that reconditioning of a device can utilize a variety of techniques for disassembly, cleaning/replacement, and reassembly. Use of such techniques, and the resulting reconditioned device, are all within the scope of the present application.

Preferably, the invention described herein will be processed before surgery. First, a new or used instrument is obtained and if necessary cleaned. The instrument can then be sterilized. In one sterilization technique, the instrument is placed in a closed and sealed container, such as a plastic or TYVEK bag. The container and instrument are then placed in a field of radiation that can penetrate the container, such as gamma radiation, x-rays, or high-energy electrons. The radiation kills bacteria on the instrument and in the container. The sterilized instrument can then be stored in the sterile container. The sealed container keeps the instrument sterile until it is opened in the medical facility.

It is preferred that device is sterilized. This can be done by any number of ways known to those skilled in the art including beta or gamma radiation, ethylene oxide, steam.

One skilled in the art will appreciate further features and advantages of the invention based on the above-described embodiments. Accordingly, the invention is not to be limited by what has been particularly shown and described, except as indicated by the appended claims. All publications and references cited herein are expressly incorporated herein by reference in their entirety.

The invention claimed is:

1. A method of forming a restriction in a patient, comprising:

using an implantable pressure sensing device to obtain pressure data over a period of time related to a pressure within an implantable restriction device configured to form a restriction in a patient;

determining a portion of the obtained pressure data which corresponds to a time within the period of time when a meal was consumed by the patient based on at least one of a time of day the pressure data was obtained and a duration of the obtained pressure data being above a nominal pressure level;

storing at least a portion of the obtained pressure data at the implantable pressure sensing device;

in response to a signal from an external device, downloading at least a portion of the stored data to the external device;

telemetrically providing power to the implantable pressure sensing device from the external device by moving the external device in proximity of the implantable pressure sensing device, wherein telemetrically providing power triggers a download of the portion of the stored data to the external device; and discarding pressure data obtained during the period of time that does not correspond to the time within the period of time when the meal was consumed such that the discarded data is not downloaded to the external device.

2. The method of claim 1, further comprising compressing at least a portion of obtained pressure data prior to storing the at least a portion of the obtained pressure data at the implantable pressure sensing device.

3. The method of claim 2, wherein the compressing includes using at least one compression technique selected from the group consisting of: storing difference values, storing values, using a quantization table, using run-length coding, and using Huffman coding.

4. The method of claim 1, wherein the obtained pressure data stored at the implantable pressure sensing device includes pressure values that exceed a nominal pressure within the implantable restriction device.

5. The method of claim 1, wherein the implantable pressure sensing device cannot download the stored pressure data without being supplied the power from the external device.

6. The method of claim 1, wherein the implantable pressure sensing device lacks an implantable power source to supply power for the download of the stored pressure data.

7. The method of claim 1, wherein storing at least a portion of obtained pressure data comprises storing all the obtained pressure data.

8. A method of forming a restriction in a patient, comprising: obtaining pressure data related to a pressure within an implantable restriction device configured to form a restriction in a patient;

determining a portion of the obtained pressure data to retain prior to communicating pressure data to an external reading device, the determining comprising comparing the obtained pressure data with a pre-programmed pressure chosen by a user and indicating a nominal pressure within the implantable restriction device;

storing in an implantable memory the obtained pressure data that exceeds the pre-programmed pressure;

communicating the portion of the obtained pressure data stored in the memory to the external reading device;

determining to retain pressure data obtained during the pre-determined time of day and determining to not retain pressure data obtained outside the pre-determined time of day;

storing in the implantable memory any of the pressure data obtained during the pre-determined time of day; and communicating the stored pressure data obtained during the pre-determined time of day.

9. The method of claim 8, wherein the pre-programmed pressure is a defined range of pressure values, and determining a portion of the pressure data to retain comprises determining if any of the obtained pressure data includes a value within the defined range of pressure values and determining to store the obtained pressure data in the implantable memory based on whether the obtained pressure data falls within the range.

10. The method of claim 8, further comprising generating an alert for communication to the external reading device if any of the obtained pressure data includes a value that exceeds a threshold pressure value.

11. The method of claim 8, wherein storing in the implantable memory only the obtained pressure data that exceeds the pre-programmed pressure comprises storing the portion of the pressure data determined to be retained prior to communicating the portion of the obtained pressure data to the external reading device.

12. The method of claim 11, further comprising compressing the portion of the pressure data determined to be retained prior to storing the portion of the pressure data determined to be retained.

13. The method of claim 8, wherein obtaining pressure data includes reducing a rate of pressure data gathering during a determined period.

14. The method of claim 8, wherein determining a portion of the pressure data to retain includes processing the obtained pressure data using a pressure sensing device coupled to the implantable restriction device and configured to obtain the pressure data.

15. The method of claim 14, wherein processing the obtained pressure data includes using a processor in electronic communication with the pressure sensing device.

16. The method of claim 8, wherein the pre-programmed pressure is based on at least one of a historical performance of the implantable restriction device in the patient and a performance of the implantable restriction device in a typical patient.

17. A method of forming a restriction in a patient, comprising: using an implantable pressure sensing device to obtain pressure data over a period of time related to a pressure within an implantable restriction device configured to form a restriction in a patient;

storing at the implantable pressure sensing device an absolute value of the obtained pressure data at a start of the period of time;

storing at the implantable pressure sensing device difference values of the obtained pressure data relative to the absolute value for a remainder of the period of time after the start;

determining a portion of the obtained pressure data which corresponds to a time within the period of time when a meal was consumed by the patient based on at least one of a time of day the pressure data was obtained and a duration of the obtained pressure data being above a nominal pressure level; and discarding pressure data obtained during the period of time that does not correspond to the time within the period of time when the meal was consumed such that the discarded data is not downloaded to an external device.

18. The method of claim 17, further comprising compressing at least one of the absolute value and the difference values prior to storage of the at least one of the absolute value and the difference values, wherein the compressing includes using at least one compression technique selected from the group consisting of: using quantization table, using run-length coding, and using Huffman coding.

19. The method of claim 17, further comprising communicating the stored absolute value and difference values from the pressure sensing device to the external device.

20. The method of claim 17, further comprising using the implantable pressure sensing device to obtain pressure data over a second, subsequent period of time related to the pressure within the implantable restriction device;

storing at the implantable pressure sensing device an absolute value of the obtained pressure data at a start of the second period of time; and storing difference values of the obtained pressure data for a remainder of the second period of time after the start of the second period of time.

* * * * *